(12) United States Patent
Chan et al.

(10) Patent No.: US 7,541,460 B2
(45) Date of Patent: Jun. 2, 2009

(54) PROCESS FOR PREPARING THE ANTIVIRAL AGENT [1S-(1ALPHA, 3ALPHA, 4BETA)]-2-AMINO-1,9-DIHYDRO-9-[4-HYDROXY-3-(HYDROXYMETHYL)-3-METHYLENECYCLOPENTYL]-6H-PURIN-6-ONE

(75) Inventors: Yeung Yu Chan, Kendall Park, NJ (US); Sushil K. Rijhwani, Robbinsville, NJ (US)

(73) Assignee: Bristol-Myers Squibb Company, Princeton, NJ (US)

( * ) Notice: Subject to any disclaimer, the term of this patent is extended or adjusted under 35 U.S.C. 154(b) by 331 days.

(21) Appl. No.: 11/311,194

(22) Filed: Dec. 19, 2005

(65) Prior Publication Data

US 2006/0106215 A1 May 18, 2006

Related U.S. Application Data

(62) Division of application No. 10/734,012, filed on Dec. 11, 2003, now Pat. No. 7,034,152.

(60) Provisional application No. 60/432,549, filed on Dec. 11, 2002.

(51) Int. Cl.
   *C07D 473/18* (2006.01)
   *C07D 473/40* (2006.01)
   *C07F 7/08* (2006.01)
   *C07F 7/10* (2006.01)
   *C07F 7/18* (2006.01)

(52) U.S. Cl. ..................................... 544/276
(58) Field of Classification Search .................. 544/276
   See application file for complete search history.

(56) References Cited

U.S. PATENT DOCUMENTS

| | | | |
|---|---|---|---|
| 4,471,130 A | 9/1984 | Katsuki et al. | |
| 4,594,439 A | 6/1986 | Katsuki et al. | |
| 4,900,847 A | 2/1990 | Hanson et al. | |
| 5,206,244 A | 4/1993 | Zahler et al. | |
| 2005/0272932 A1* | 12/2005 | Zhou et al. | 544/276 |
| 2006/0106216 A1* | 5/2006 | Pendri et al. | 544/276 |
| 2007/0060599 A1* | 3/2007 | DiMarco et al. | 514/263.37 |

FOREIGN PATENT DOCUMENTS

WO WO 98/09964 3/1998
WO WO 01/64221 9/2001

OTHER PUBLICATIONS

Bonini, C. et al., "A critical outlook and comparison of enantioselective oxidation methodologies of olefins", Tetrahedron, vol. 58, pp. 4981-5021 (2002).
Danishefsky, S.J. et al., "Novel Stereospecific Silyl Group Transfer Reactions: Practical Routes to the Prostaglandins", J. Am. Chem. Soc., vol. 111, pp. 3456-3457 (1989).
Fleming, I., "Silyl-to-Hydroxy Conversion in Organic Synthesis", Chemtracts—Organic Chemistry, vol. 9, pp. 1-64 (1996).
Greene, T.W. et al., Protective Groups in Organic Synthesis, Second Edition, John Wiley & Sons, Inc., publ., pp. 198-201 (1991).
Griffith, D.A. et al., "The Total Synthesis of Allosamidin. Expansions of the Methodology of Azaglycosylation Pursuant to the Total Synthesis of Allosamidin. A Surprising Enantiotopic Sense for a Lipase-Induced Deacetylation", J. Am. Chem. Soc., vol. 118, No. 40, pp. 9526-9538 (1996).
Jones, G.R. et al., "The Oxidation of the Carbon-Silicon Bond", Tetrahedron, vol. 52, No. 22, pp. 7599-7662 (1996).
Khanapure, S.P. et al., "An Efficient Synthesis of 4(*S*)-Hydroxycyclopent-2-enone", J. Org. Chem., vol. 60, No. 23, pp. 7548-7551 (1995).
Li, G. et al., "*N*-Halocarbamate Salts Lead to More Efficient Catalytic Asymmetric Aminohydroxylation", Angew. Chem. Int. Ed. Engl., vol. 35, No. 23/24, pp. 2813-2817 (1996).
Miyaji, K. et al., "Synthesis of Corey Lactone Via Highly Stereoselective Asymmetric Diels-Alder Reaction", Tetrahedron Letters, vol. 32, No. 35, pp. 4557-4560, 1991.
Carceller et al., "Synthesis of cis-bicyco [13.3.0]oct-3-ene-2, 7-dione, a highly functionalized cyclopentanoid intermediate," Tetrahedron Letters, vol. 25, Issue 19, 1984, pp. 2031-2034.
Pearson, A.J. et al., "Conjugate Additions of Carbon Nucleophiles to Cyclopentadienones," Organic Letters, vol. 5, No. 14, 2003, pp. 2547-2459.
Humiliere, D. et al., "A New Enantioselective Synthesis of Highly Functionalized Cyclopentanols," Synlett 1998, pp. 1255-1257.
Bisacchi, G.S. et al., "BMS-200475, a novel carbocyclic 2'-deoxyguanosine analog with potent and selective anti-hepatitis B virus activity in vitro," Bioorganic & Medicinal Chemistry Letters, vol. 7, Issue 2, 21 1997, pp. 127-132.
Ziegler, F.E., et al., "Radical cyclization studies directed toward the synthesis of BMS-200475 'entecavir': the carbocyclic core," Tetrahedron, vol. 59, Issue 45, Nov. 3, 2003, pp. 9013-9018.

* cited by examiner

*Primary Examiner*—Mark L Berch
(74) *Attorney, Agent, or Firm*—Jennifer T. Chin-Chapman; James Epperson

(57) ABSTRACT

Processes are disclosed for preparing the antiviral agent entecavir. A resin adsorption process for the isolation and purification of entecavir is also disclosed. Various intermediates useful in the preparation of entecavir are also disclosed.

2 Claims, No Drawings

PROCESS FOR PREPARING THE ANTIVIRAL AGENT [1S-(1ALPHA, 3ALPHA, 4BETA)]-2-AMINO-1,9-DIHYDRO-9-[4-HYDROXY-3-(HYDROXYMETHYL)-3-METHYLENECYCLOPENTYL]-6H-PURIN-6-ONE

CROSS-REFERENCE TO RELATED APPLICATIONS

This application is a Divisional of U.S. Non-Provisional Application No. U.S. Ser. No. 10/734,012 filed Dec. 11, 2003 now U.S. Pat. No. 7,034,152 and claims the priority benefit of U.S. Provisional Application No. 60/432,549 filed Dec. 11, 2002, the disclosure of which is incorporated herein by reference in its entirety.

BACKGROUND OF THE INVENTION

Entecavir, [1S-(1α,3α,4β)]-2-amino-1,9-dihydro-9-[4-hydroxy-3-(hydroxymethyl)-2-methylenecyclopentyl]-6H-purin-6-one, is currently being evaluated as a drug for use in treating hepatitis B viral infections.

Entecavir and its use as an antiviral agent are described in U.S. Pat. No. 5,206,244 to Zahler et al., assigned to the present assignee. Improved processes of preparing entecavir are described by Bisacchi et al., in WO 98/09964, also to the present assignee.

Colonno, et al. in WO 01/64221 describe compositions containing a low dose of entecavir administered on a daily basis to treat hepatitis B virus infection and/or co-infections.

SUMMARY OF THE INVENTION

This invention is directed to various methods for preparing entecavir as recited in the claims appended hereto. Entecavir (the compound of formula 21) has the structural formula shown below:

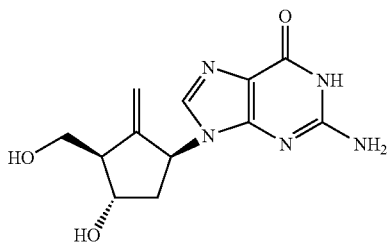

21

This invention is also directed to various intermediates useful in the preparation of entecavir and the methods of preparing such intermediates.

This invention is also directed to a resin adsorption process for isolation and purification of entecavir and intermediates thereof.

DETAILED DESCRIPTION OF THE INVENTION

Abbreviations

For ease of reference, the following abbreviations are used in this application and have the meanings given below:
Ac=acyl;
AP=HPLC area percent;
Bn=benzyl;
BHT=2,6-di-tert-butyl-4-methylphenol;
CHP=cumene hydroperoxide, or α,α-dimethylbenzylhydroperoxide;
DCM=dichloromethane;
de=diastereometric excess;
DBU=1,8-diazabicyclo[5.4.0]undec-7-ene;
DEAD=diethylazodicarboxylate;
DEMA=diethoxymethyl acetate;
DIPT=(−)-diisopropyl tartrate;
DMAP=4-N,N-dimethylaminopyridine;
DMF=N,N-dimethylformamide;
DiPMA=di-isopropyloxymethyl acetate; [(iPr—O)$_2$CHOAc];
DMSO=dimethyl sulfoxide;
ee=enantiomeric excess;
Et=ethyl;
EtOAc=ethyl acetate;
Et$_3$N=triethylamine;
FMSA=fluoromethane sulfonic acid;
HCl=hydrochloric acid
IPA=isopropanol;
K$_2$CO$_3$=potassium carbonate;
KF=potassium fluoride;
KHCO$_3$=potassium bicarbonate;
KHMDS=potassium hexamethyldisilazide or potassium bis(trimethylsilyl)amide;
KOH=potassium hydroxide;
KOtBu=potassium tert-butoxide;
LAH=lithium aluminum hydride;
LiOH=lithium hydroxide;
m-CPBA=meta-chloroperbenzoic acid;
MeOH=methanol
MOP=2-methoxy-2-propoxy-acetal;
MSA=methanesulfonic acid;
MTBE=methyl tert-butyl ether;
NaBH$_4$=sodium borohydride;
Na$_2$CO$_3$=sodium carbonate;
NaHCO$_3$=sodium bicarbonate;
NaH=sodium hydride;
NaOH=sodium hydroxide;
NaOtBu=sodium tert-butoxide;
NMP=N-methyl-2-pyrrolidinone;
TMS=trimethylsilyl;
PPTS=pyridinium 4-toluenesulfonate or pyridinium p-toluenesulfonate;
PTSA=para-toluene sulfonic acid;
Red-Al® or RED-AL®=sodium bis(2-methoxyethoxy)aluminum hydride;
TBAH=n-tetrabutyl ammonium hydroxide;
TBHP=tert-butylhydroperoxide;
TEOF=tri-ethylorthoformate;
TFA=trifluoroacetic acid;
THF=tetrahydrofuran;
Ti(O-iPr)$_4$=titanium (IV) isopropoxide;
TiPOF=trisopropylorthoformate;
TMOF=trimethylorthoformate.

DEFINITIONS

The following terms shall have, for the purposes of this application, including the claims appended hereto, the respective meanings set forth below. It should be understood that when reference herein is made to a general term, such as acid, base, oxidizing agent, etc. one skilled in the field may make appropriate selections for such reagents from those given in the definitions below, as well as from additional reagents recited in the specification that follows, or from those found in literature references in the field.

"Anhydride" refers generally to compounds that will react with water or solvent to form an acid, e.g., including carboxylic acid anhydrides having the formula R—C(=O)—O—C(=O)R', wherein R and R' are selected from alkyl or aryl groups, as defined below, more preferably, wherein R and R' are selected from methyl and ethyl.

"Acid" refers to any compound that contains hydrogen and dissociates in water or solvent to produce positive hydrogen ions, as well as Lewis acids, including but not limited to acids such as hydrochloric acid, sulfuric acid, phosphoric acid, acetic acid, trihaloacetic acid (e.g., TFA), hydrogen bromide, maleic acid, sulfonic acids such as toluenesulfonic acids and camphorsulfonic acids, propionic acids such as (R)-chloropropionic acid, phthalamic acids such as N-[(R)-1-(1-naphthyl)ethyl] phthalamic acid, tartaric acids such as L-tartaric acid and dibenzyl-L-tartaric acid, lactic acids, camphoric acids, aspartic acids, citronellic acids, $BCl_3$, $BBr_3$, and so forth. Thus, the term includes weak acids such as ethanoic acid and hydrogen sulfide; strong organic acids such as methanesulfonic acid, trifluoroacetic acid, etc.; and so forth.

"Activated methyl carbonic acid reagent" means a reagent effective to prepare a methyl carbonate ester from an alcohol. Non-limiting examples include methyl chloroformate, dimethyl pyrocarbonate, and the like.

"Alkyl" as used herein includes linear or branched alkyl groups having from one to twelve carbon atoms, more preferably from one to eight carbon atoms, and most preferably, from one to four carbon atoms, unless otherwise specifically described. The term alkyl may be optionally substituted with up to four (more preferably 0 to 2), substituents selected from the group of non-interfering substituents recited below. The term lower alkyl refers to alkyl groups having from one to four carbon atoms. When a subscript is used with reference to an alkyl or other group, the subscript refers to the number of carbon atoms that the group may contain. For example, the term "$C_{1-4}$alkyl" refers to alkyl groups of 1 to 4 carbon atoms. Alkyl moieties incorporated in other radicals are also linear or branched, unless specifically described otherwise. When the term alkyl is used as a prefix in conjunction with another group, as in alkylaryl, this means the alkyl as defined above is present as a divalent moiety (i.e., alkylene), creating a linkage to the other, named group. Thus, alkylaryl includes benzyl and the like.

"Alkoxy" as used herein includes alkyl groups as defined above, bonded through an oxygen atom, i.e., —O-alkyl.

"Alkali metal salt" refers to salts formed with alkali metals, preferably salts of sodium, lithium or potassium.

"Allyl" refers to the group —$CH_2$—CH=$CH_2$, which may be optionally substituted with one or more (preferably 0 to 1) non-interfering substituents as defined below.

"Anti-oxidant" refers to a chemical compound or complex that is effective to slow or inhibit the rate of an oxidation reaction. Exemplary anti-oxidants may include, without limitation, β-carotene, $ZrO_2$, ascorbic acid, aromatic amines, phenols, quinones including BHT, citric acid, ascorbic acid, vitamin E, benzoic acid, phosphoric acid, and so forth.

"Aryl" includes monocyclic or bicyclic aromatic groups having 6 to 12 carbon atoms in the ring portion, i.e., phenyl and naphthyl, as well as heteroaryl groups, e.g., 4 to 7 membered monocyclic, 7 to 11 membered bicyclic, or 10 to 15 membered tricyclic aromatic ring systems, which have at least one heteroatom and at least one carbon atom-containing ring. Exemplary monocyclic heteroaryl groups include pyrrolyl, pyrazolyl, pyrazolinyl, imidazolyl, oxazolyl, isoxazolyl, thiazolyl, thiadiazolyl, isothiazolyl, furanyl, thienyl, oxadiazolyl, pyridyl, pyrazinyl, pyrimidinyl, pyridazinyl, triazinyl and the like. Exemplary bicyclic heteroaryl groups include indolyl, benzothiazolyl, benzodioxolyl, benzoxazolyl, benzothienyl, quinolinyl, tetrahydroisoquinolinyl, isoquinolinyl, and the like. The term "aryl" may be optionally substituted with up to four (preferably 0 to 2) non-interfering substituents.

"Base" when used herein includes hydroxides or alkoxides, hydrides, or compounds such as ammonia, that accept protons in water or solvent. Thus, exemplary bases include, but are not limited to, alkali metal hydroxides and alkoxides (i.e., MOR, wherein M is an alkali metal such as potassium, lithium, or sodium, and R is hydrogen or alkyl, as defined above, more preferably where R is straight or branched chain $C_{1-5}$ alkyl, thus including, without limitation, potassium hydroxide, potassium tert-butoxide, potassium tert-pentoxide, sodium hydroxide, sodium tert-butoxide, lithium hydroxide, etc.); other hydroxides such as magnesium hydroxide ($Mg(OH)_2$), calcium hydroxide ($Ca(OH)_2$), or barium hydroxide ($Ba(OH)_2$); alkali metal hydrides (i.e., MH, wherein M is as defined above, thus including, without limitation, sodium, potassium, and lithium hydrides); alkylated disilazides, such as, for example, potassium hexamethyldisilazide and lithium hexamethyldisilazide; carbonates such as potassium carbonate ($K_2CO_3$), sodium carbonate ($Na_2CO_3$), potassium bicarbonate ($KHCO_3$), and sodium bicarbonate ($NaHCO_3$); alkyl ammonium hydroxides such as n-tetrabutyl ammonium hydroxide (TBAH); and so forth.

"Benzyl" includes the group —$CH_2$-phenyl, the methyl or phenyl portions of the benzyl may be optionally substituted with non-interfering substituents as defined below, unless otherwise indicated.

"Benzyl halide" refers to a benzyl group having a halide substituent on the alkyl portion of the benzyl group, i.e., Ph—$CH_2$—X, wherein X is halide, and Ph denotes a phenyl ring as defined below.

"Benzyloxy" refers to the group —O-benzyl, wherein the benzyl moiety is as described immediately above.

"Brominated styrene-based resin" refers to one or more styrene-based resins having one or more bromine substituents, and includes without limitation, SP207 Sepabeads, SP700 Sepabeads, Diaion HP20, Diaion SP70, Diaion SP825, Diaion SP850, Diaion HP2MG methacrylate, AMBERLITE XAD4, AMBERLITE XAD7HP, AMBERLITE XAD16, and AMBERLITE XAD1600.

"Chiral amine" or "CA" as used herein refers to an amine or mixture of amines that is optically active including dextrorotatory or laevorotatory forms of amines. Preferably, the chiral amine comprises a pure or substantially pure form of one optical isomer, but optically active mixtures (i.e., mixtures that are not equimolar) are also contemplated. If reference is made herein to a "homochiral amine," it is intended to encompass the broader concept of "chiral amine" as well. For example, these amines include, without limitation, (1R,2R)-(+)-1,2-diphenylethylenediamine, (R)-(−)-1-cyclohexylethylamine, D-threo-2-amino-1-(4-nitrophenyl)-1,3-propanediol, (1S,2S)-(+)-1,2-diaminocyclohexane, dehydroabietylamine, (1R,2R)-1,2-diaminomethylcyclohexane, cinchonidine and cinchonine "Diastereoselective epoxidation" refers to a reaction wherein one diastereomeric epoxide is preferentially formed. The term "diastereoselective epoxidation" thus includes Sharpless epoxidations wherein epoxidation of an allylic alcohol preferentially gives one enantiomer. However, the term "diastereoselective epoxidation" as used herein also more broadly covers the epoxidation of a diastereomeric compound, or the epoxidation of an otherwise non-racemic compound. The term "diastereoselective epoxidation" is intended to include enantioselective oxidation of olefins as described in Bonini and Righi, "*A Critical Outlook And Comparison of Enantioselective Oxidation Methodologies of Olefins*", *Tetrahedron*, Vol. 58 (2002), at pp. 4981-5021, incorporated herein by reference.

"Halide" or "halo" refers to F, Cl, Br, or I, preferably Cl or I.

"Hydride reagent" refers to reagents that are capable of delivering H⁻ ions. Exemplary hydride reagents include, but are not limited to, lithium aluminum hydride (LiAlH$_4$), sodium borohydride (NaBH$_4$), Red-Al® (sodium bis[2-methoxyethoxyaluminum]hydride), zinc borohydride, diisobutylaluminum hydride, sodium borohydride-cerium chloride, lithium triethylborohydride, lithium 9-BBN hydride, 9-BBN pyridine, borane-sulfide complex, 5,5-diphenyl-2-methyl-3,4-propan-1,3,2-oxazaborolidine (Corey Reagent), lithium tri-tert-butoxyaluminum hydride, sodium cyanoborohydride, lithium tri-sec-butyl borohydride (L-Selectride®), diisobutylaluminum chloride, borane-tetrahydrofuran complex, and the like.

"Hydroperoxide" means a compound or complex comprising the hydroperoxide moiety HO$_2$—, such as compounds having the formula (R$^p$OOH), wherein R$^p$ can be hydrogen (e.g., hydrogen peroxide H$_2$O$_2$), or can be an alkyl, substituted alkyl, aryl, alkylaryl, substituted aryl, or substituted alkylaryl or other moiety (including without limitation compounds wherein the methyl moiety of the benzyl group is optionally substituted). Hydroperoxides thus include α,α-dimethylbenzylhydroperoxide, tert-butylhydroperoxide, and the like.

"Hydroxy protecting groups" means those groups that one skilled in the field would recognize as being suitable to protect the —OH substituent on an alkyl or ringed system as described herein and which may be removed under deprotection conditions known to those skilled in the field as set forth, for example, in the latest edition of Greene and Wuts, *Protecting Groups in Organic Synthesis*, incorporated herein. As an illustration, nonlimiting examples of hydroxy protecting groups include ether protecting groups (e.g. benzyl ethers, silyl ethers such as tert-butyldimethylsilyl ether), esters (e.g., benzoate, acetate), and acetals (e.g., MOP).

"Homochiral diester of tartaric acid" as used herein includes single diastereomers of alkyl tartrates including diethyl tartrate and diisopropyl tartrate.

"Metal catalyst" refers to compounds and complexes including metallic elements that are effective as catalysts and encompasses, without limitation. "transition metal catalysts." Metal catalysts include, without limitation, titanium (IV) isopropoxide, palladium salts such as palladium (0) catalyst, e.g., tetrakis(triphenylphosphine)palladium, copper(I)triflate, rhodium(II)acetate, Rh$_6$(CO)$_{16}$, and so forth.

"Non-interfering substituent" refers to a substituent that is bonded to a compound or complex identified herein that does not render the compound or complex inoperable, with regard to the functionality or object to be achieved with the particular compound or complex, and which is compatible with the reaction sequences detailed herein. Such substituents may be selected by one skilled in the field depending on the particular reaction step and function to be achieved. Exemplary non-interfering substituents may include without limitation groups such as alkyl, halogen, cyano, nitro, trifluoromethyl, trifluoromethoxy, —OR, —SR, —C(=O)R, —CO$_2$R, aryl, alkylaryl, C$_{3-7}$cycloalkyl, —NRR'$_2$, —NRC(=O)R', —SO$_{(q)}$R'', —NRSO$_{(q)}$R'', —SO$_{(q)}$R'', —C(=O)NRR', and the like; and alkyl groups substituted with one to four (preferably 1 to 2) of halogen, cyano, nitro, trifluoromethyl, trifluoromethoxy, —OR, —SR, —C(=O)R, —CO$_2$R, aryl, alkylaryl, C$_{3-7}$cycloalkyl, —NRR'$_2$, —NR—C(=O)R', —SO$_{(q)}$R'', —NRSO$_{(q)}$R'', —SO$_{(q)}$R'', —C(=O)NRR', and the like, wherein R and R' are hydrogen, alkyl, benzyl, or aryl, as defined above, R'' is alkyl, benzyl, or aryl, as defined above, and q is 1, 2 or 3.

"Orthoformate derivatives" means reagents effective for the preparation of dioxolanes from vicinal diol moieties, or for the preparation of imidazole rings from vicinal diamines on, for example 5,6-diaminopyrimidine derivatives. Non-limiting examples include triethylorthoformate, trimethylorthoformate, triisopropylorthoformate, diethoxymethyl acetate, and di-isopropyloxymethylacetate.

"Oxidizing agent," or "oxidizing source" refers to any compound or complex that is known in the field for its effects in converting a functional group in a molecule from a lower oxidation state to a higher oxidation state. For example, oxidizing agents may include, without limitation, m-CPBA, hydrogen peroxide, AcOOH in AcOH, potassium peroxymonosulfate, sodium periodate, sodium percarbonate, potassium permanganate, ruthenium oxide, and the like. Oxidizing agents may be used in the presence of one or more additives, such as KF, KHCO$_3$, NEt$_3$, AcONa, and the like. As one skilled in the field will appreciate, additives may be selected depending on the particular oxidizing agents used and the reaction conditions.

"Per-acid" as used herein includes without limitation, magnesium monoperoxyphthalate (MPPA), perbenzoic acids, and peracetic acid.

"Phenyl" may be optionally substituted with up to four (preferably 0 to 2) non-interfering substituents as defined above. When the term phenyl is used as a suffix following another term, as in alkylphenyl, or alkoxy phenyl, this means the phenyl group is connected via a divalent moiety of the other, specifically-named group. Thus, alkylphenyl includes benzyl, phenylethyl, and the like.

"Protecting group" includes without limitation such groups as are set forth, for example, in the latest edition of Greene and Wuts, *Protecting Groups in Organic Synthesis*, incorporated herein by reference.

"Reducing reagent" refers to any compound or complex that is known in the field for its effects in converting a functional group in a molecule from one oxidation state to a lower oxidation state. Exemplary reducing reagents include, without limitation, NaBH$_4$, LAH, lithium borohydride, diisobutylaluminum hydride, sodium bis(2-methoxyethoxyaluminum) hydride, and the like. The term "reducing reagent" will include "hydride reagents" as recited above.

"Strong non-nucleophilic base" means a non-aqueous base that does not act as a nucleophile, such as sodium or potassium bistrimethylsilylamide, lithium diisopropylamide, sodium bistrimethylsilylamide, potassium, lithium, or sodium hydride.

"Tertiary amine base" means a trialkylamine, such as triethylamine, N,N-dimethylethylamine, diisopropylethylamine (Hunig's base) or tetramethylenediamine (TMEDA), or a nitrogen containing heterocycle, such as pyridine.

"Trimethylsilylating reagent" means a reagent effective to prepare a trimethylsilyl ether from an alcohol. Non-limiting examples include chlorotrimethylsilane, trimethylsilyl trifluoromethanesulfonate, and the like.

Additionally, it should be understood in the methods of preparation and claims herein, that the pronoun "a", when used to refer to a reagent, such "a base", "a metal catalyst", "a hydroperxoide" and so forth, is intended to mean "at least one" and thus, include, where suitable, single reagents as well as mixtures of reagents. Thus, for example, a reaction step involving use of "a base", or for example, involving use of "a base selected from one of potassium hydroxide, potassium tert-butoxide, potassium tert-pentoxide, sodium hydroxide, sodium tert-butoxide, lithium hydroxide," encompasses use of potassium hydroxide as a base, or, where appropriate, mixtures of potassium hydroxide plus one or more additional bases set forth in the group from which a selection may be made. One skilled in the field may make appropriate selections given the reactions steps and conditions and result to be achieved.

Methods of Preparation

The compound entecavir and novel intermediates therefor may be prepared by the exemplary processes described in the following reaction Schemes. Exemplary reagents and procedures for these reactions appear hereinafter or are described above. Starting materials are commercially available or can be readily prepared by one of ordinary skill in the art. Solvents, temperatures, pressures, starting materials having the desired groups, and other reaction conditions, may be readily selected as appropriate by one of ordinary skill in the art.

Process A

SCHEME 1

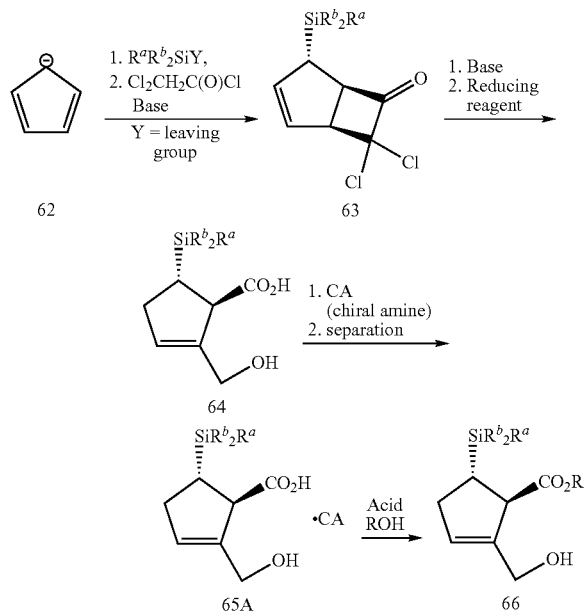

Process A of the invention comprises preparation of the ester of formula 66, a preferred intermediate or starting material for preparing entecavir 21. In the ester of formula 66, R is a $C_1$ to $C_4$ alkyl or benzyl, preferably methyl; $R^a$ is allyl, phenyl, $C_1$ to $C_6$ alkylphenyl or $C_1$ to $C_6$ alkoxyphenyl, more preferably $R^a$ is selected from phenyl, $C_1$ to $C_3$ alkylphenyl, and $C_1$ to $C_3$ alkoxyphenyl; and $R^b$ is $C_1$ to $C_6$ alkyl, preferably methyl. The ester can be prepared by any method that provides the ester in high diastereomeric and enantiomeric purity. A preferred procedure is shown in Scheme 1, wherein sodium cyclopentadienide 62 is treated with a silylating reagent, e.g., $R^a(R^b)_2SiY$, wherein Y is a leaving group, e.g., phenyldimethylchlorosilane wherein $R^a$ is phenyl, $R^b$ is methyl, and Y is Cl. The reaction may be carried out in a solvent such as MTBE and/or THF. The resulting silane moiety serves as a masked hydroxy group that can be unveiled later in the synthetic process. The product of the silylation reaction can then be elaborated using a 2+2 cycloaddition reaction with ketene, e.g., generated from dichloroacetyl chloride and an appropriate base (e.g., $Et_3N$, NaOH, KOH, $NaHCO_3$, $KHCO_3$, $Na_2CO_3$, $K_2CO_3$, TBAH, etc.), to give the cyclobutanone of formula 63. The cyclobutanone can then be opened with a suitable base (e.g., $Et_3N$, NaOH, KOH, $NaHCO_3$, $KHCO_3$, $Na_2CO_3$, $K_2CO_3$, TBAH, etc.), and the resulting intermediate reduced with a suitable reducing agent, e.g., $NaBH_4$, to provide the carboxylic acid of formula 64.

Resolution of the enantiomers of the carboxylic acid 64 can be accomplished by salt formation with chiral amines (CAs) and separation of the resulting diastereomeric salts. A diastereomeric mixture of ammonium salts of the carboxylic acid of formula 64 is preferably prepared using R,R-(−)-2-amino-1-(4-nitrophenyl)-1,3-propanediol. Those of ordinary skill in the art will appreciate that other chiral amines can be used to achieve the resolution of the enantiomers of the carboxylic acid of formula 64. These amines include, for example, (1R,2R)-(+)-1,2-diphenylethylenediamine, (R)-(−)-1-cyclohexylethylamine, D-threo-2-amino-1-(4-nitrophenyl)-1,3-propanediol, (1S,2S)-(+)-1,2-diaminocyclohexane, dehydroabietylamine, (1R,2R)-1,2-diaminomethylcyclohexane, cinchonidine and cinchonine.

Separation of the resulting diastereomeric salts can be accomplished by any separation procedure known to those of ordinary skill in the art, such as chromatography or crystallization. Separation of the diastereomeric salts is preferably effected by crystallization. For example, the diastereomerically enriched ammonium salt of formula 65A (where the chiral amine used is R,R-(−)-2-amino-1-(4-nitrophenyl)-1,3-propanediol) can be isolated by crystallization from EtOH. The ammonium salt of formula 65A isolated by this procedure can have a chemical purity of 98% and 98% de Conversion of the ammonium salt of formula 65A to the ester of formula 66 (R is alkyl) can be accomplished by heating in an acidic solution, e.g., MeOH and an appropriate acid, such as sulfuric acid or p-toluenesulfonic acid, or HCl in methylene chloride. Alternatively, compound 65A can be converted into a free acid which is subjected to esterification with alcohol, e.g., MeOH, in the presence of PTSA, at refluxing conditions, to provide compound 66.

Process B

SCHEME 2

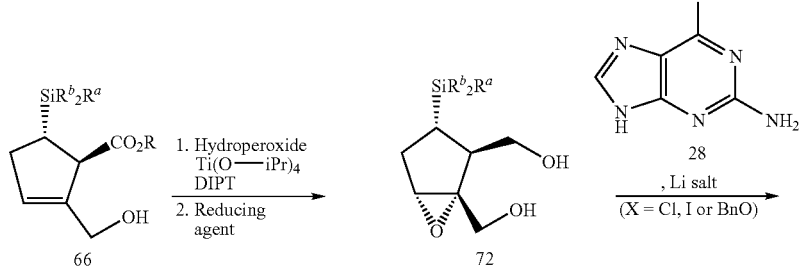

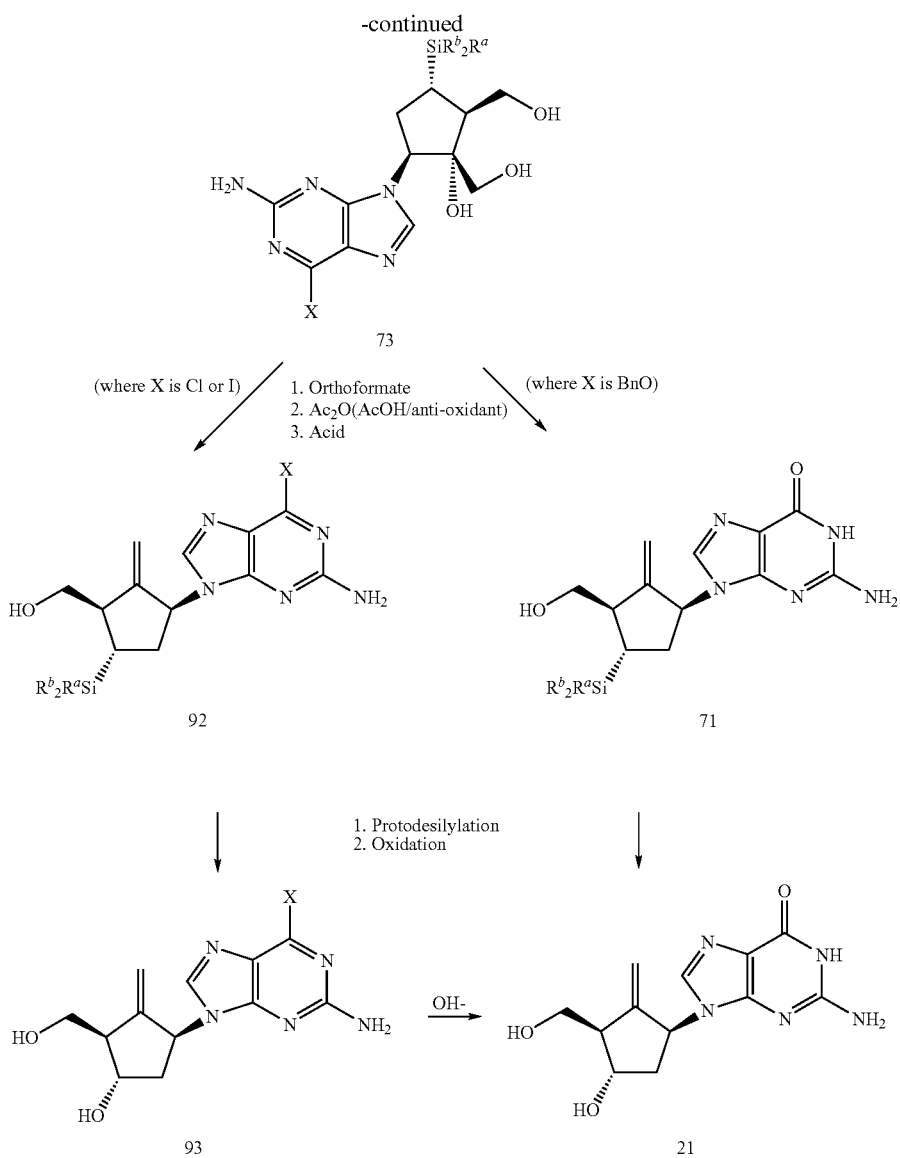

Process B of the invention comprises preparing entecavir 21, via coupling an epoxide of formula 72, with a substituted guanine derivative to prepare a carbocyclic nucleoside, the compound of formula 73, which is then elaborated to the compound 21. One embodiment of Process B is depicted in Scheme 2. In this process, a preferred starting material for the epoxide of formula 72 is an ester of formula 66 (which can be prepared as described in Scheme 1). The compound of formula 66 can be epoxidized and the ester group can be reduced to furnish the cyclopentane epoxide of formula 72 in high diastereomeric purity. For example, the compound of formula 66 can serve as starting material for a diastereoselective epoxidation reaction. In one embodiment, the cyclopentane epoxide of formula 72 is formed after the epoxidation and reduction steps in at least 96% de. The diastereoselective epoxidation can be effected with a per acid or with a per homochiral diester of tartaric acid, a hydroperoxide, and a metal catalyst, such as a transition metal catalyst. Preferably, the homochiral ester is DIPT, the hydroperoxide is TBHP or CHP, and the metal catalyst is titanium (IV) isopropoxide. Preferably, the reaction is carried out in an inert solvent such as dry DCM or toluene. Methods suitable for effecting the catalytic epoxidation reactions are described in U.S. Pat. Nos. 4,471,130; 4,594,439; and 4,900,847, incorporated herein by reference. After workup, the crude product can be carried on in the synthesis without further purification.

The crude product from the epoxidation reaction is treated with a reducing reagent that selectively reduces the ester group to an alcohol, such as, e.g., $NaBH_4$, LAH, lithium borohydride, diisobutylaluminum hydride, sodium bis(2-methoxyethoxyaluminum) hydride, and the like. In one embodiment, the reducing agent used in the reaction is $NaBH_4$ in IPA. The reduction provides the cyclopentane epoxide having the formula 72.

The cyclopentane epoxide of formula 72 can then be heated, for example, to about 80° C. with an alkali metal salt, e.g., a lithium salt, of the purine compound of formula 28, wherein X is Cl, I, or benzyloxy (BnO) in a dipolar aprotic solvent such as DMF to prepare the compound of formula 73. For example, the lithium salt of 2-amino-6-O-benzyloxypurine is prepared by treatment with base such as LiOH or LiH. This coupling reaction to prepare the carbocyclic nucleoside is advantageous in that it provides a high N-9 to N-7 ratio (e.g., N-9:N-7>20:1), allows convenient workup and purification procedures, and provides useful yields of the compound of formula 73. For example, after water workup, the crude product of the coupling reaction of the purine compound of formula 28 wherein X is BnO, and the cyclopentane epoxide of formula 72, can be purified by simple recrystallization from a solution of EtOAc-hexanes to provide the compound of formula 73 in 65% yield.

The compound of formula 73, wherein X is BnO, can then be converted to the compound of formula 71 by converting the vicinal diol moiety to an alkene. Analogously, the compound of formula 73, wherein X is Cl or I, can be converted to compound 92 by converting the vicinal diol moiety to an alkene. In one embodiment, the vicinal diol of the compound of formula 73 is converted to an alkene as in compounds 71 and 92, by a two-step procedure. In the first step, the compound of formula 73 is treated with an orthoformate derivative, such as DEMA, DiPMA, TiPOF, TEOF, or TMOF, in the presence of an acid such as PPTS or TFA. The reaction is preferably carried out in an inert solvent such as DCM, toluene, or tert-butyl methyl ether, at room temperature for a sufficient amount of time to form a product comprising a diastereomeric mixture of dioxolanes. In the second step, the diastereomeric mixture of dioxolanes is heated with acetic anhydride, preferably in the presence of acetic acid and an antioxidant, e.g., BHT, to form the alkene. In embodiments wherein X is BnO, the crude product from the acetic anhydride treatment can then be heated with acid such as aqueous mineral acid or aqueous organic acid, e.g., HCl or MSA, to hydrolyze the 6-benzyloxy group (as well as an 2-N-acetyl group formed in the acetic anhydride treatment) to provide the methylene compound of formula 71, or its salts (e.g., MSA or HCl salts). The intermediates of formulas 71 and 92 can be isolated in the form of a salt by treatment with an acid such as HCl, MSA, (1S)-(+)-10-camphorsulfonic acid, (R)-chloropropionic acid, N-[(R)-1-(1-naphthyl)ethyl] phthalamic acid, L-tartaric acid, dibenzyl-L-tartaric acid, L-lactic acid, (1R,3S)-camphoric acid, L-aspartic acid, (S)-citronellic acid, etc.

Preparation of the final compound 21 from compound 71 can then be accomplished by converting the silane moiety to a hydroxy moiety. This conversion can be achieved via protodesilylation of the silane moiety followed by oxidation with an oxidizing source, such as, for example, hydrogen peroxide. The protodesilylation step can be achieved via reaction with boron trifluoride-acetic acid complex, or a Bronsted acid such as TFA, MSA, FMSA, or tetrafluoroboric acid in an inert solvent, e.g., DCM. Alternatively, protodesilylation can be achieved with a base or acid as described below in Scheme 6. Upon debenzylation (which may, in some embodiments, be achieved in the protodesilyation step (e.g., when MSA or FMSA are used), there is provided the protodesilylated intermediate of formula 91

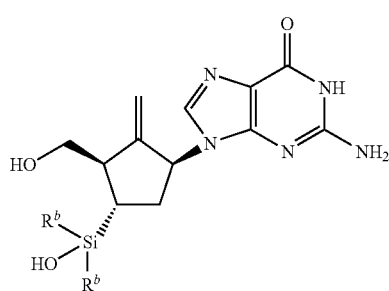

The protodesilylated intermediate 91 can then be oxidized. The oxidizing agent(s) can be selected in view of the reagent used to achieve protodesilyation. For example, when boron trifluoride-acetic acid complex is used, the compound can be oxidized with hydrogen peroxide and $KHCO_3$, to provide the target compound of formula 21, and when a Bronsted acid is used, compound 91 may be oxidized with hydrogen peroxide, $KHCO_3$, and KF. Other acids and oxidizing agents that may be useful may be recited above. Alternatively, conversion of the silyl moiety to a hydroxy group may be achieved as described in Scheme 6, below, and additional methods that may be useful for the transformation of the silyl group to the hydroxy group are described in Fleming, I. (*Chemtracts-Organic Chemistry* 1996, 9, 1-64) and Jones, G. R. et al. (*Tetrahedron*, 1996, 52, 7599-7662), both of which are herein incorporated by reference. The compound of formula 21 can be further purified, for example, by recrystallization from water, and/or via resin purification as described below in Process K.

In alternate embodiments of Process B, the purine 28, coupled with cyclopentane epoxide 72 to give compound 73, is other than 2-amino-6-benzyloxypurine, such as 2-amino-6-chloropurine or 2-amino-6-iodopurine. In this embodiment, compound 73 is upon treatment with the orthoformate, acid, etc., converted to compound 92 , which upon protodesilylation and oxidation is converted to compound 93. In this instance, wherein 2-amino-6-chloropurine or 2-amino-6-iodopurine is used, an additional treatment with aqueous base or acid (preferably aqueous base) may be utilized to convert the halo group of compound 93 into the 6-oxo moiety. For example, aqueous NaOH solution may be used to convert the compound of formula 93 to the compound of formula 21.

Process C

SCHEME 3

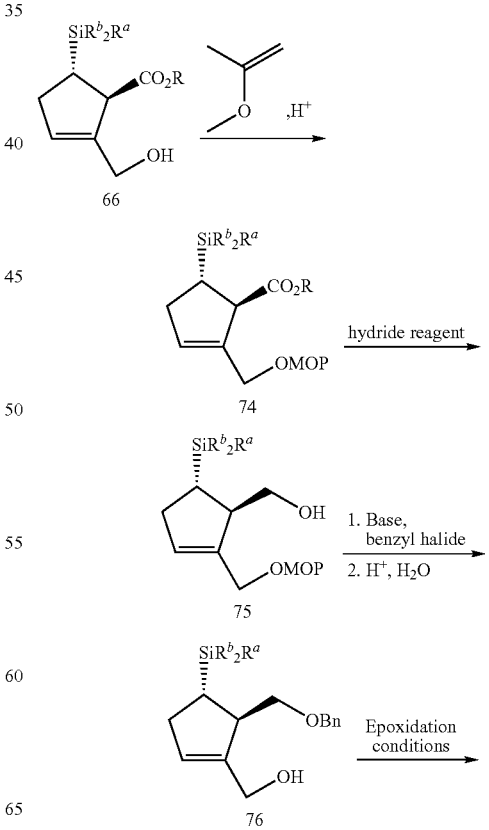

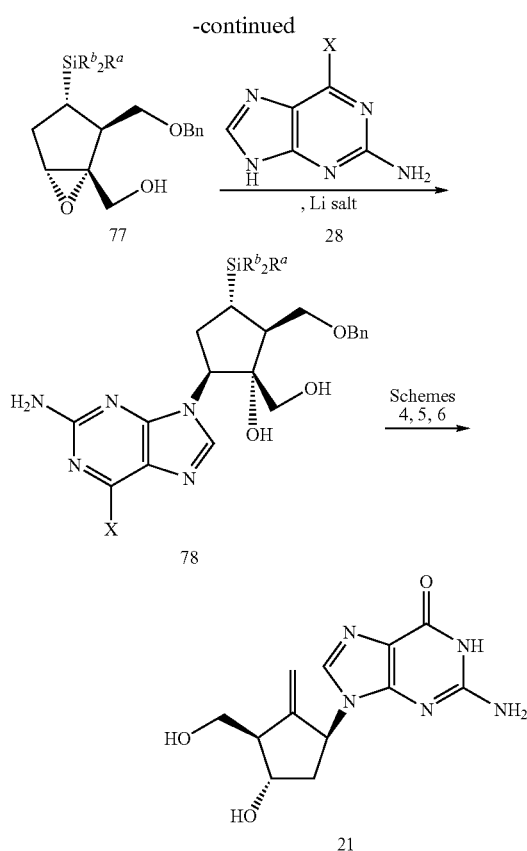

The ester of formula 66 can also be converted to the compound of formula 21 by the methods of Process C. One embodiment of Process C is depicted in Scheme 3. In contrast to Process B, the epoxidation reaction of the cyclopentane in Process C is performed after the ester moiety has been reduced. In Process C, the primary alcohol moiety of the ester of formula 66 (R=alkyl) is protected with a protecting group such as a MOP by treatment with 2-methoxypropene and a catalytic amount of an acid, such as PPTS, in an insert solvent such as toluene, to yield the compound of formula 74. The carboxylic ester moiety of 74 can be reduced with a hydride reagent, preferably Red-Al® or LAH. In one embodiment, the ester moiety of 74 is reduced, preferably after the addition of a suitable base, such as with a tertiary amine base, e.g., Et₃N, in the same reaction vessel to give the compound of formula 75. In another embodiment, the ester moiety of 74 is reduced with a hydride reagent after workup, to give compound 75. The resultant alcohol moiety of the compound of formula 75 is first protected with a protecting group that is resistant to hydrolysis conditions that are then used to remove the MOP group. For example, the alcohol moiety of the compound of formula 74 can be treated with a base (e.g., KOtBu, KHMDS, NaH, phase-transfer catalyst conditions using 50% NaOH), and a benzyl halide, e.g., benzyl bromide or benzyl chloride, preferably in solvent such as toluene or THF, to protect the alcohol moiety as a benzyl ether. The MOP acetal can then be hydrolyzed by addition of aqueous acid, such as 1 N HCl, to give the allylic alcohol of formula 76. Other protecting groups known in the field may be found in the literature, such as Greene and Wuts, cited above in the general definitions herein.

The allylic alcohol of formula 76 serves as starting material for a diastereoselective epoxidation reaction, wherein the product, the cyclopentane epoxide of formula 77, is formed in high diastereomeric purity. For example, the epoxidation can be effected using a homochiral diester of tartaric acid, a hydroperoxide, and a metal catalyst, such as a transition metal catalyst. Alternately, the diastereoselective epoxidation may be performed with a peracid, such as MPPA, as described in Scheme 14 and Example 12. Preferably, diastereoepoxidation is performed with the homochiral ester DIPT, the hydroperoxide TBHP or CHP, and the metal catalyst Ti(O—iPr)₄. Preferably, the reaction is carried out in an inert solvent such as toluene, methylene chloride, etc. In one embodiment, the cyclopentane epoxide of formula 77 is formed in at least 96% de.

The cyclopentane epoxide of formula 77 can then be reacted (e.g., at elevated temperature, e.g., preferably at about 80° C.) with an alkali metal salt of purine compound of formula 28, wherein X is Cl, I or BnO, in a dipolar aprotic solvent such as DMF to prepare the compound of formula 78. Preferably, the purine compound of formula 28 is 2-amino-6-benzyloxypurine. The 2-amino-6-benzyloxypurine is commercially available or can be prepared from 6-chloroguanine and the sodium salt of benzyl alcohol (e.g., upon treatment with NaOH in benzyl alcohol, toluene, and MeOH, or upon treatment with the sodium salt of benzyl alcohol, benzyl alcohol, in EtOH/water.). The alkali metal salt can be generated in situ by reaction of 2-amino-6-O-benzyloxypurine with, for example, LiH or LiOH. The crude compound of formula 78, wherein X is benzyloxy, can be isolated and purified. For example, the crude compound 78 can be isolated upon addition of IPA and water, then purified by recrystallization with solvents or solvent mixtures known in the field.

The compound of formula 78 can then be converted to the compound of formula 21 using various reaction sequences analogous to those used to convert the compound of formula 73 to the compound of formula 21 in Process B, which are further described in Schemes 4, 5 and 6, below.

Process C(a)

SCHEME 4

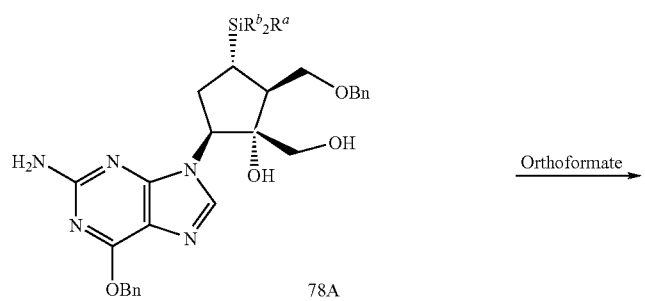

-continued
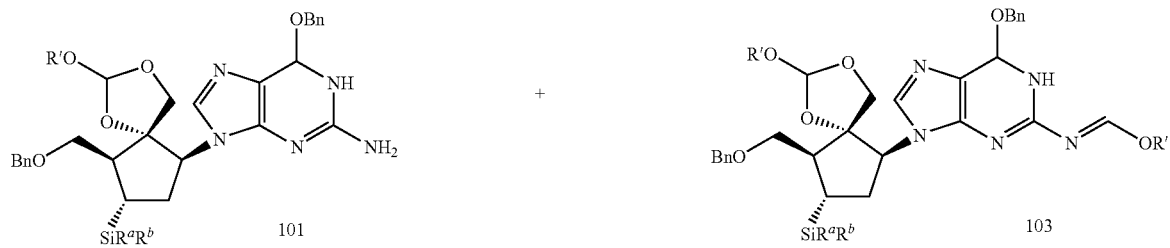
R' = C$_{1-4}$alkyl, C(=O)C$_{1-4}$alkyl
Ac$_2$O(HOAc/anti-oxidant) ↓
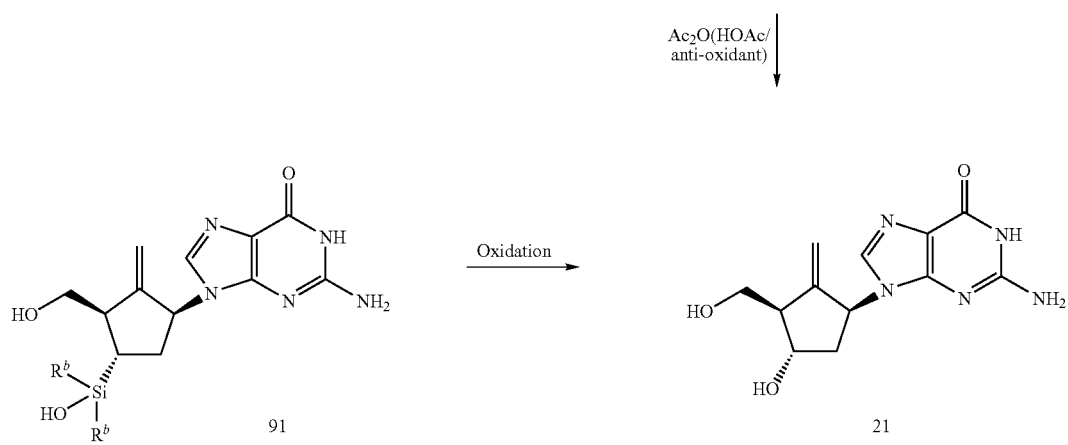
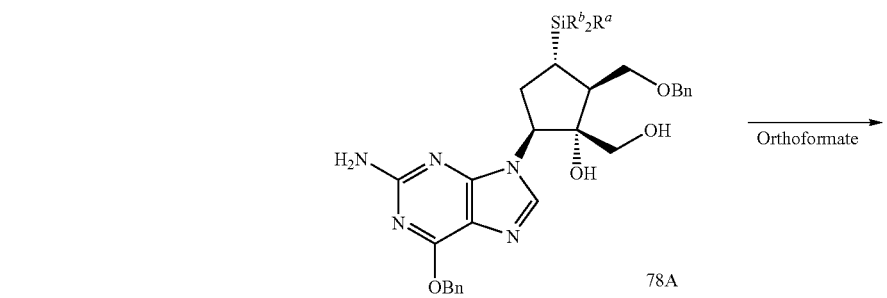
Orthoformate →
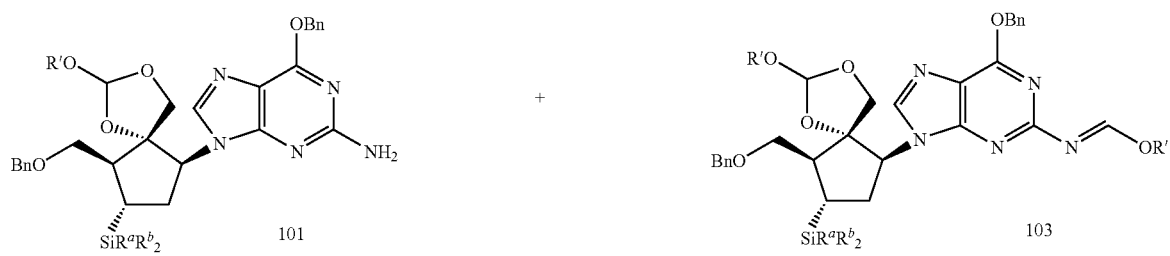
R' = C$_{1-4}$alkyl, C(=O)C$_{1-4}$alkyl
Ac$_2$O(HOAc/anti-oxidant) ↓

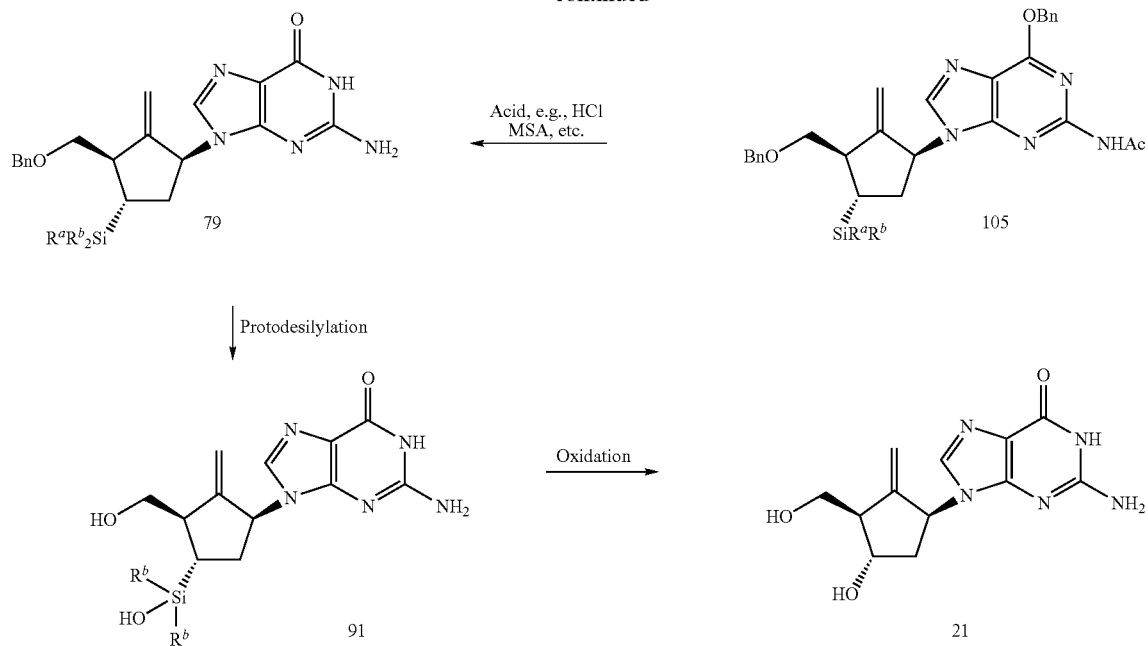

Scheme 4 describes a process for converting compound 78A (compound 78 wherein X is OBn), to the compound of formula 21. Compound 78A can be treated with an orthoformate derivative, such as DEMA, DiPMA, TMOF, TiPOF, TEOF, etc., preferably in an inert solvent such as toluene, DCM, MTBE etc., as described in Scheme 2, in the presence of a catalytic amount of an acid such as TFA or PTSA, or an acid catalyst such as PPTS, etc., to form a product comprising a diastereomeric mixture of dioxolanes, e.g., compounds 101 and 103. The diastereomeric mixture of dioxolanes 101 and 103 can be heated with acetic anhydride preferably in the presence of acetic acid and an anti-oxidant, such as BHT, to form alkene having the formula 105. The crude product 105 can then be heated with acid, such as with aqueous HCl or MSA, in an appropriate solvent such as MeOH and water, to hydrolyze the 6-benzyloxy and N-acetyl groups and provide the methylene compound of formula 79. The intermediate 79 can be isolated in the form of a salt by treatment with an acid such as HCl, MSA, (1S)-(+)-10-camphorsulfonic acid, (R)-chloropropionic acid, N-[(R)-1-(1-naphthyl) ethyl] phthalamic acid, L-tartaric acid, dibenzyl-L-tartaric acid, L-lactic acid, (1R, 3S)-camphoric acid, L-aspartic acid, (S)-citronellic acid, etc. In one embodiment, intermediate 79 or salts thereof are further purified by recrystallization, e.g., intermediate 79 salts thereof are treated with NaOH in an organic solvent and crystallized before proceeding to the next step.

Preparation of the final compound of formula 21 from compound 79, or salts thereof, can then be accomplished by converting the silane moiety to a hydroxy moiety. This conversion can be achieved via protodesilylation of the silane moiety with reagent(s) selected to provide the intermediate compound 91, followed by oxidation. Protodesilylation may be achieved with boron trifluoride-acetic acid complex or a Bronsted acid in insert solvent, e.g., MSA in methylene chloride. Oxidation may be carried out as described in Scheme 2, using oxidizing agents and additives appropriately selected, i.e., depending on the reagent used for protodesilylation and the oxidizing agent, e.g., in the case of a Bronsted acid, hydrogen peroxide in the presence of $KHCO_3$ and KF may be used, to provide compound 21. Compound 21 can be further purified, for example, by recrystallization from water, and/or via resin purification as described below in Process K.

Process C(b)

SCHEME 5

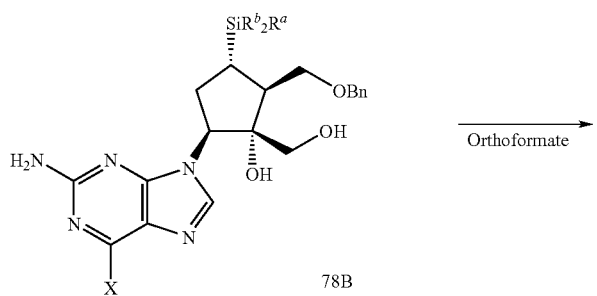

-continued
R' = C$_{1-4}$alkyl, C(=O)C$_{1-4}$alkyl
Ac$_2$O(HOAc/anti-oxidant) ↓
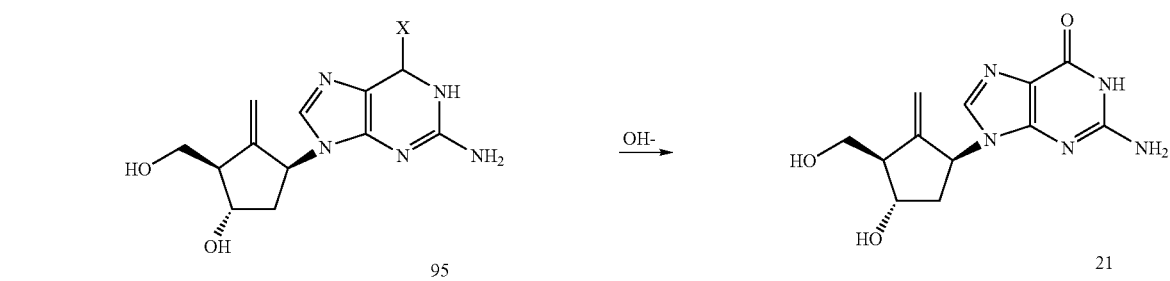
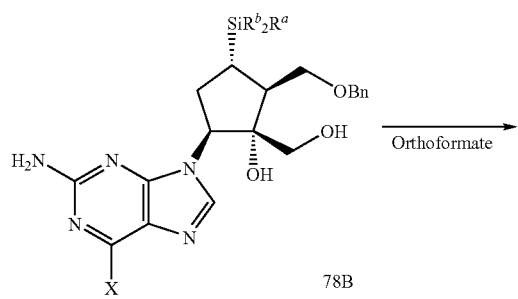
R' = C$_{1-4}$alkyl, C(=O)C$_{1-4}$alkyl
Ac$_2$O(HOAc/anti-oxidant) ↓
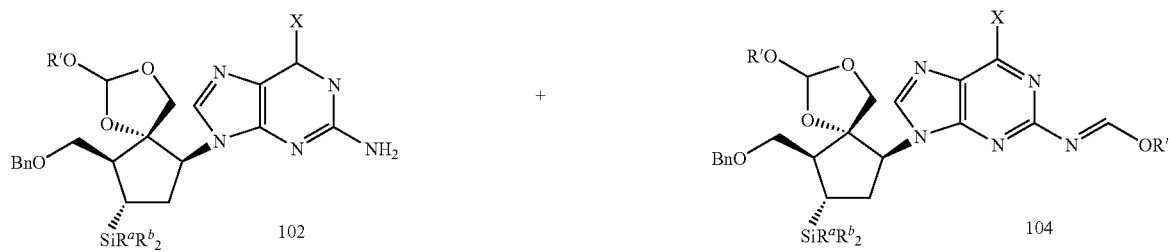

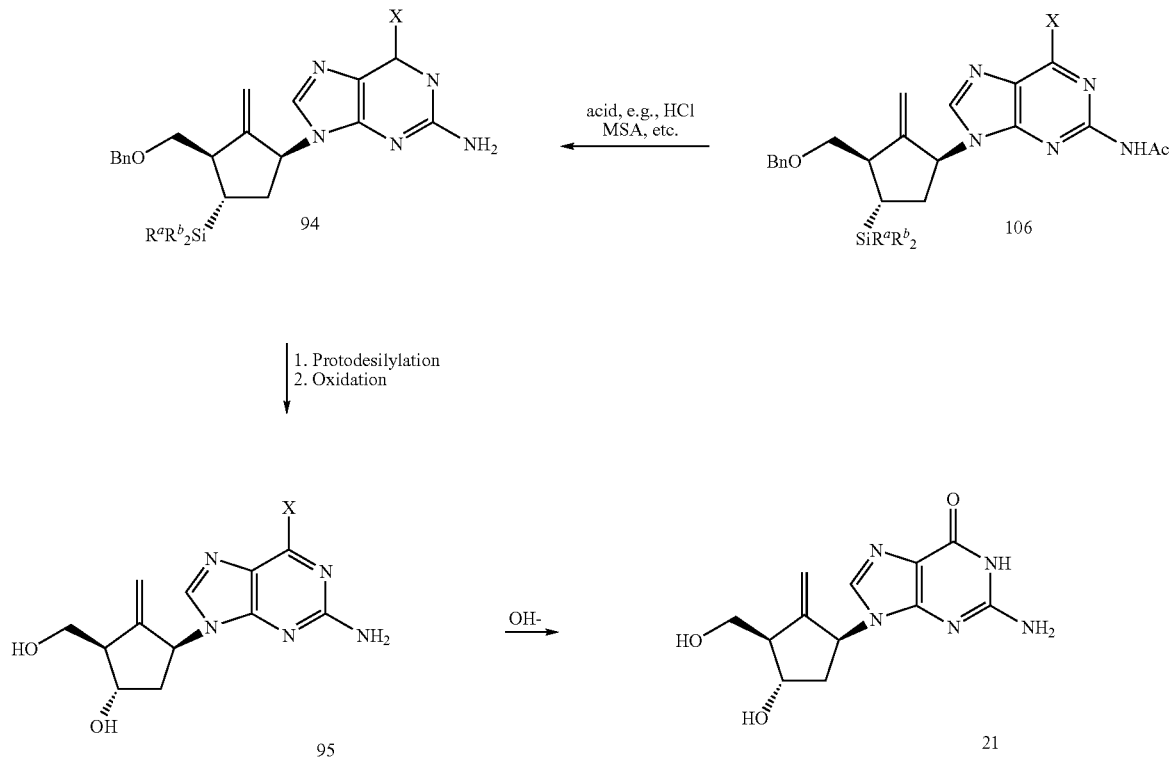

Scheme 5 describes an alternate process for making compound 21, wherein the purine 28 of Scheme 3 is 2-amino-6-chloropurine or 2-amino-6-iodopurine, such that coupling with cyclopentane epoxide 77, yields compound 78B (compound 78 wherein X is Cl or I). As in Scheme 4, compound 78B can be treated with an orthoformate derivative to form a product comprising a diastereomeric mixture of dioxolanes 102 and 104, which can be heated with acetic anhydride, preferably in the presence of acetic acid and an anti-oxidant, e.g., BHT, to form alkene 106. The product 106 can then be heated with acid, such as HCl or MSA, as described in Scheme 4, to hydrolyze the acyl group and provide compound 94, or salts thereof, which retain the 6-position X group. Protodesilylation, debenzylation, and oxidation as described in Scheme 4, provides the intermediate compound 95. Compounds 94 and 95 can be isolated in the form of their salts by treatment with acid(s) as previously described for compound 79. Compound 95 can then be treated with aqueous base or acid (preferably, an aqueous base) to convert the halo group of compound 95 into the 6-oxo moiety of compound 21. As may be appreciated, with Process C(b) an additional step may be used for the conversion of compound 78 to 21, as compared with Process C(a).

Process C(c)

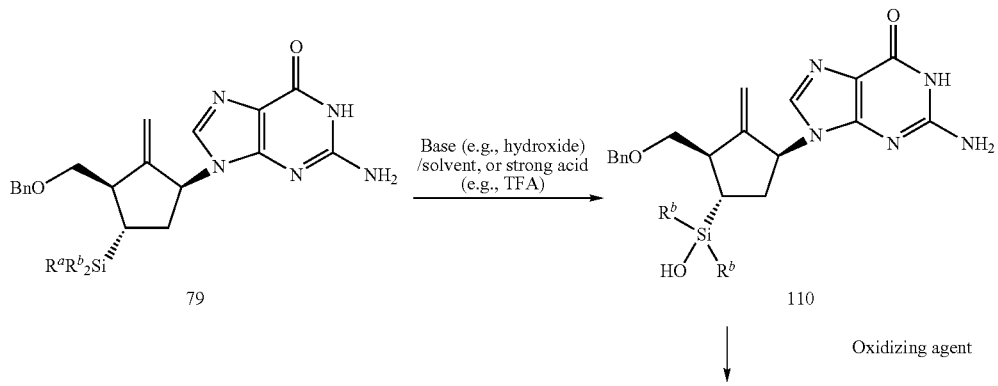

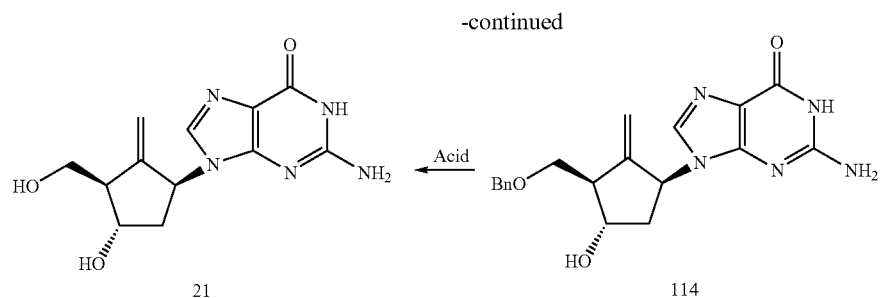

Scheme 6 shows an alternate process for preparing compound 21 from compound of formula 79, which is shown in Scheme 4. As compared with Scheme 4, in this scheme a different base or acid is used to achieve the protodesilylation, followed by oxidation and debenzylation to convert compound 79 to compound 21. Compound 79 is treated with a base such as a hydroxide, e.g., NaOH or KOH, or alkoxide such as KOtBu, in a polar aprotic solvent such as DMF, DMSO, or NMP, or with a strong acid such as TFA, and heated at a time and temperature sufficient to achieve the conversion to intermediate 110. Compound 110 can then be oxidized with hydrogen peroxide in the presence of $KHCO_3$ and KF in a solvent such as MeOH, to provide intermediate 114. Intermediate 114 can be debenzylated upon treatment with a Lewis acid such as $BCl_3$, $BBr_3$, etc., or a Bronsted acid such as MSA, TFMSA, etc., in solvent such as DCM, and the reaction mixture can be neutralized with base such as NaOH, to provide compound 21. Compound 21 can be further purified by recrystallization from water and/or resin purification as described below.

Process D

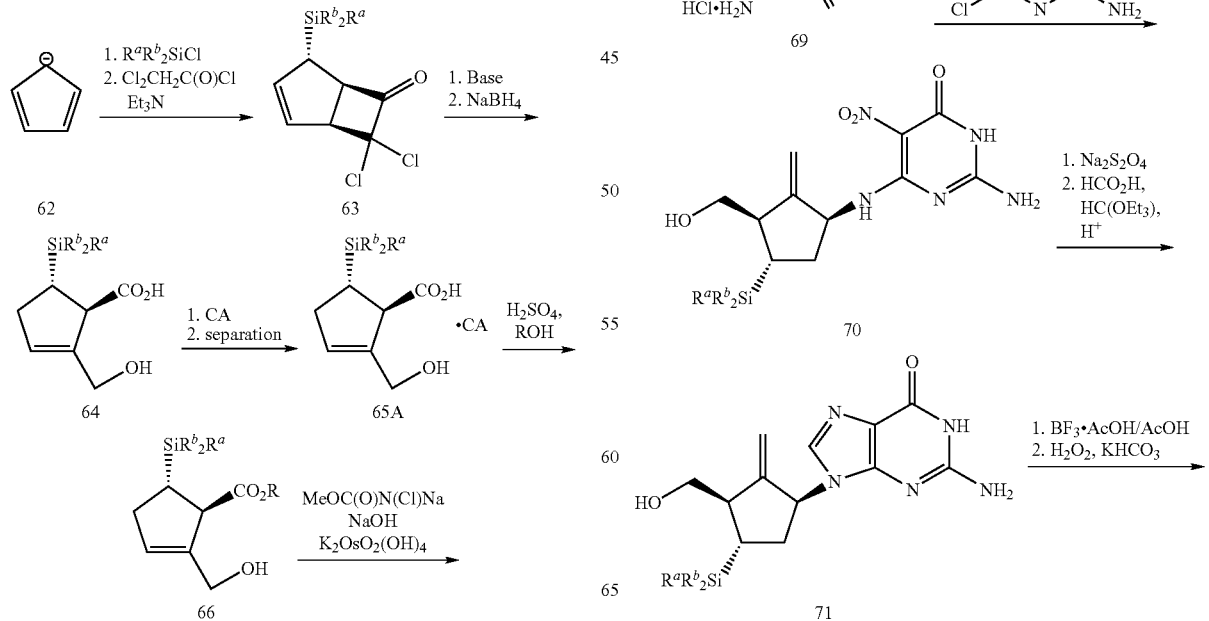

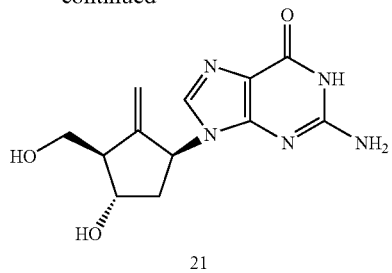

21

In Process D of the invention, the ester of the formula 66 (Scheme 1) can be converted to the compound of formula 21 using different synthetic methods. In Process D, the ester of formula 66 is aminohydroxylated to provide a chiral oxazolidinone of the formula 67. After a series of synthetic steps, a pyrimidine carbocyclic nucleoside, the compound of formula 70 is prepared. The pyrimidine carbocyclic nucleoside can be elaborated to a purine containing compound, the methylene compound of formula 71 which is subsequently converted to the compound of formula 21 by, for example, the oxidation procedure described in the final steps of Processes B and C. One embodiment of Process D is depicted in Scheme 7.

Aminohydroxylation conditions are used to convert the ester of formula 66 to the oxazolidinone of formula 67. Amino hydroxylation procedures are analogous to those described in Li, G.; Angert, H.; Sharpless, K. B. *Angew. Chem. Int. Ed.*, (1996), at 2813. Preferably, the aminohydroxylation conditions comprise treatment with: the reagent prepared from the treatment of methyl carbamate with tert-butyl hypochlorite and sodium hydroxide [i.e., MeOC(O)N(Cl)Na]; and potassium osmate in an inert solvent such as DCM. Alternative reagents include EtOC(O)N(Cl)Na and BnOC(O)N(Cl)Na. Preferably, the chiral oxazolidinone of formula 67 is formed in at least 96% de.

The primary alcohol moiety of the oxazolidinone of formula 67 can then be converted to an iodide. For instance, in one preferred procedure, the compound of formula 67 is treated with trifluoromethanesulfonic anhydride (Tf$_2$O) in the presence a tertiary amine base such as pyridine, and subsequently treated with an iodide salt, e.g, lithium iodide. The resulting iodide of the formula 68 can then be converted to a methylene compound of formula 69 by a two step procedure. In the first step the iodide of formula 68 is treated with zinc powder and acetic acid. The ester moiety of the resulting intermediate can then be reduced to a primary alcohol in the second step by a hydride reagent such as sodium bis[2-methoxyethoxyaluminum]hydride to give the amine of the formula 69.

The amine of the formula 69 is subsequently reacted with a substituted chloropyrimidine. The amine can be condensed, for example, with 2-amino-6-chloro-5-nitro-4-(3H)-pyrimidinone in the presence of a tertiary amine base, preferably triethylamine, in refluxing n-butanol to give a pyrimidine compound of formula 70. The pyrimidine compound of formula 70 can then be converted to a purine derivative by a two step procedure. In the first step, the nitro moiety of the pyrimidine is reduced with, for example, sodium dithionite, to give a triaminopyrimidine intermediate. Alternative reducing agents and conditions that can also successfully reduce the nitro group include NaBH$_4$/THF, NaBH$_4$—BiCl$_3$, Sn/HCl, SnCl$_2$, Mg/(NH$_4$)$_2$SO$_4$/MeOH, CuBr.SMe$_2$, TiCl$_2$(Cp)$_2$/Sm, iron and nickel catalyzed procedures. In the second step, treatment of the triaminopyrimidine intermediate with formic acid, hydrochloric acid, and an orthoformate derivative, e.g., triethylorthoformate, effects cyclization and provides the methylene compound of formula 71. The methylene compound of formula 71 can be converted to the compound of formula 21 by the oxidation procedure described in the final steps of Processes B and C.

Process E

SCHEME 8

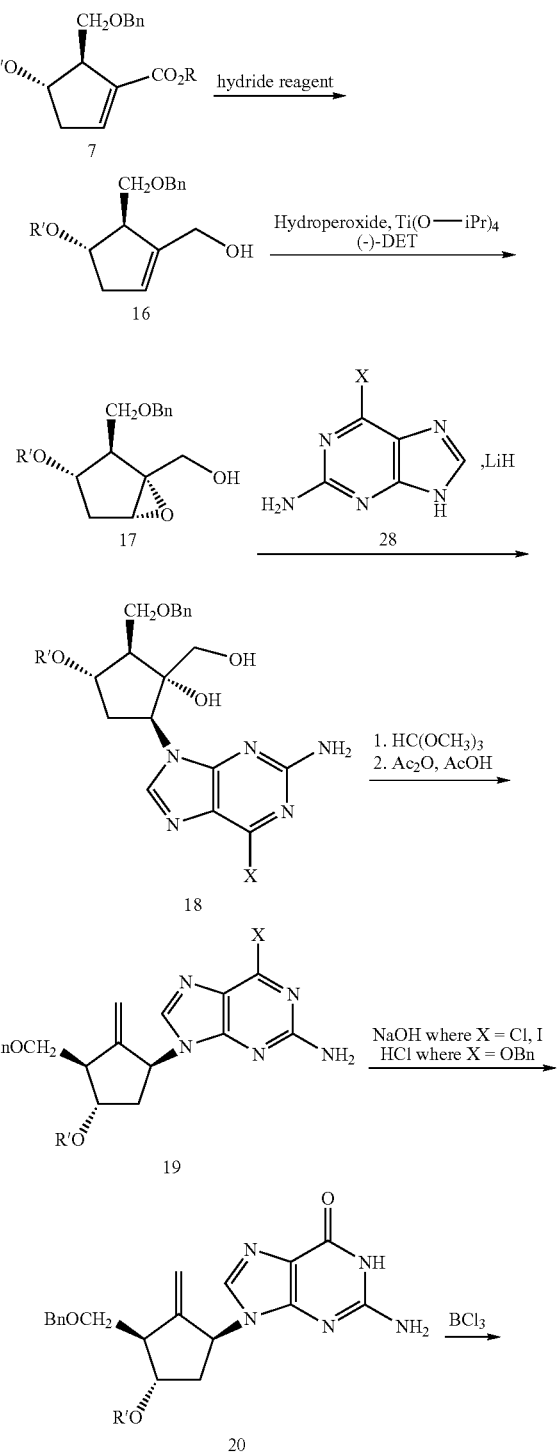

-continued

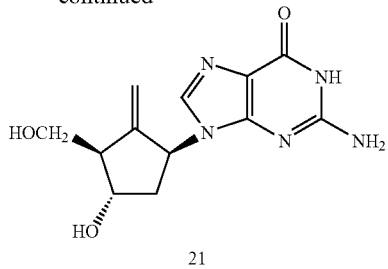

R' = H, Bn- or $R^cR^d{}_2Si$-
  $R^c$ is $C_1$ to $C_4$ alkyl, or phenyl
  $R^d$ is $C_1$ to $C_3$ alkyl Process E of the invention comprises using an alternative carbocyclic sugar precursor, an allylic alcohol of the formula 16, to prepare the compound of formula 21. Process E is similar to Processes B and C as all three processes use cyclopentane epoxide intermediates to accomplish a coupling reaction with a guanine precursor. In a first embodiment of Process E, the protecting group that serves to protect the secondary alcohol of the cyclopentane ring of 16 is a benzyl/substituted benzyl ether, while in a second embodiment a silyl ether protecting group ($R^cR^d{}_2Si$) protects the same secondary alcohol. (In this instance, $R^c$ is linear or branched $C_1$ to $C_4$ alkyl, or phenyl, and $R^d$ is linear or branched $C_1$ to $C_3$ alkyl.) A preferred benzyl ether protecting group is benzyl ether, per se, while a preferred silyl ether is tert-butyldimethyl silyl ether. The difference in these protecting groups changes the identity of the intermediates for the different embodiments of Process E. Certain embodiments of Process E are depicted in Scheme 8.

In one embodiment of Process E, the allylic alcohol of formula 16 is obtained through a reduction of the ester of the formula 7. The ester of the formula 7, wherein R and R' are as defined above, can be obtained by Processes E(a)-E(d) that are described below. The ester of formula 7 can be reduced with hydride reagents that selectively effect 1,2-reduction of the ester. For example, in one embodiment, diisobutylaluminum hydride reduces the ester group and provides the allylic alcohol of the formula 16.

The allylic alcohol of formula 16 can then be diastereoselectively epoxidized. For example, the epoxidation can be accomplished using a homochiral diester of tartaric acid, a hydroperoxide, and a metal catalyst, such as a transition metal catalyst, to yield a cyclopentane epoxide of the formula 17. In one embodiment, the homochiral diester is (−)-diethyl tartrate [(−)-DET], the hydroperoxide is TBHP or CHP, and the metal catalyst is titanium (IV) isopropoxide. Preferably, the reaction is carried out in an inert solvent such as DCM.

The epoxide of formula 17 can be subsequently coupled to an alkali metal salt (e.g., lithium) of a purine compound of formula 28, wherein X is Cl, I or BnO, in a dipolar aprotic solvent such as DMF to afford the compound of formula 18. Preferably the coupling of the cyclopentane epoxide of the formula 17 is conducted with the lithium salt of 2-amino-6-benzyloxypurine. The compound of formula 18, wherein X is benzyloxy, can be purified by crystallization from solvents such as ethyl acetate and hexanes. Typically the yield of the coupling step after purification is at least 75%.

The vicinal diol moiety of the compound of formula 18 can then be converted to an alkene moiety. For example, the diol moiety can be converted to an alkene by procedures that are analogous to those used in Processes B and C. Accordingly, in one embodiment, the compound of formula 18 can be treated with an orthoformate derivative, e.g, trimethyl orthoformate, in the presence of a catalytic amount of an acid such as TFA or PTSA, or acid catalyst such as PPTS. The resulting mixture of dioxolanes (preferably as a crude mixture) is heated with a mixture of acetic anhydride and optionally acetic acid to provide the methylene compound of formula 19. Alternatively, this reaction can be performed in the presence of antioxidant such as BHT as described previously. In the instance of the second embodiment of Process E (where the secondary alcohol of 18 is protected by a silyl ether group), the silyl ether protecting group is simultaneously hydrolyzed during the acetic anhydride/acetic acid treatment step (i.e., R' is H in the methylene compound of formula 19).

In embodiments of the Process E, wherein X is OBn, the 6-O-benzyloxy group can be hydrolyzed (as well as any pendant 2-acetamide group formed from the acetylation of the 2-amino group of the purine during the acetic anhydride treatment step) by heating the compound of formula 19 with aqueous mineral acid, such as 2 N HCl to give the methylene compound of formula 20. In embodiments of Process E, wherein X is Cl or I, the 6-halo group can be hydrolyzed by treatment with aqueous acid or base (e.g., aqueous hydroxide solution). Removal of the remaining benzyl ether protecting group(s) on the cyclopentane ring by boron trichloride treatment in an inert solvent, e.g., DCM, provides the compound of formula 21.

Process E(a)

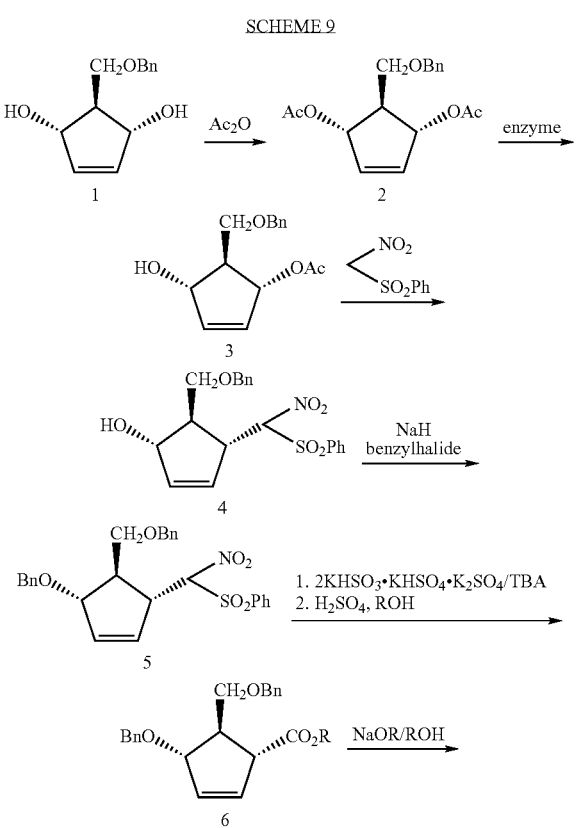

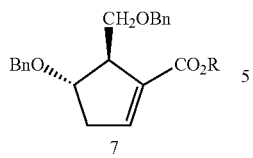

The ester of formula 7 can be prepared by methods that yield scaleable quantities of enantiomerically pure ester. In Process E(a) the ester of formula 7 can be prepared from a diol of the formula 1, which is prepared according to procedures described in *J. Am. Chem. Soc.* 1989, 3456 and *J. Am. Chem. Soc.* 1996, 9526. One embodiment of Process E(a) is depicted in Scheme 9.

The diol of formula 1 can be acetylated with, for example, acetic anhydride and pyridine to provide a diacetate of the formula 2. Selective enzymatic hydrolysis of one of the prochiral acetate functions of the diacetate provides enantiomerically pure monoacetate of the formula 3. Preferably the enzyme used is a hydrolase such as Lipase PS-30 from *Pseudomonas cepacia* or Pancreatin. Preferably the enantiomeric excess of the product monoacetate of formula 3 is at least 96% ee, more preferably at least 98% ee. In some embodiments the enzyme is immobilized on a support, e.g., polypropylene, to aid in recovery of the enzyme and facilitate reaction workup. The reaction is typically carried out in a mixture of a buffer and an organic solvent, preferably having a buffer/organic solvent ratio of about 3/1 to about 20/1, preferably about 9:1. The buffer is selected to have a buffering range effective to maintain the pH of the reaction mixture in a range effective to support enzyme catalysis, such as at about pH=7. For example, 25 mM potassium phosphate buffer can be used. In one embodiment the organic solvent is toluene.

The monoacetate of formula 3 can be coupled to phenylsulfonylnitromethane to provide a compound of formula 4. The coupling is preferably catalyzed by a palladium (0) catalyst such as tetrakis(triphenylphosphine)palladium in THF with a tertiary amine base, such as triethylamine. The secondary hydroxyl group of the compound of formula 4 is protected using a benzyl halide and a non-nucleophilic strong base such as sodium hydride to give the dibenzyl compound of formula 5. The dibenzyl compound of formula 5 can be oxidized, such as with potassium peroxymonosulfate: tetrabutyl ammonium, preferably in a solvent mixture of DCM and MeOH. The intermediate carboxylic acid can be esterified, for example, by directly heating with an alcohol (ROH), preferably MeOH, and sulfuric acid in the same reaction vessel to afford the ester of formula 6.

Isomerization of the double bond provides the desired ester of formula 7. The isomerization can be accomplished by heating the crude ester of formula 6 under basic conditions. Preferably the basic conditions comprise heating the ester with a sodium alkoxide/alcohol mixture. As will be apparent to those of ordinary skill in the art, the alkoxide and alcohol mixture are preferably selected so that transesterification of the ester moiety during the isomerization is minimized or eliminated. By way of example, if a methyl ester is desired for the compound of formula 7 (i.e., R=methyl) then the basic conditions chosen for the isomerization are preferably sodium methoxide/MeOH. The ester of formula 7 can be purified by recrystallization from a mixture of solvents such as hexanes and tert-butyl methyl ether.

Process E(b)

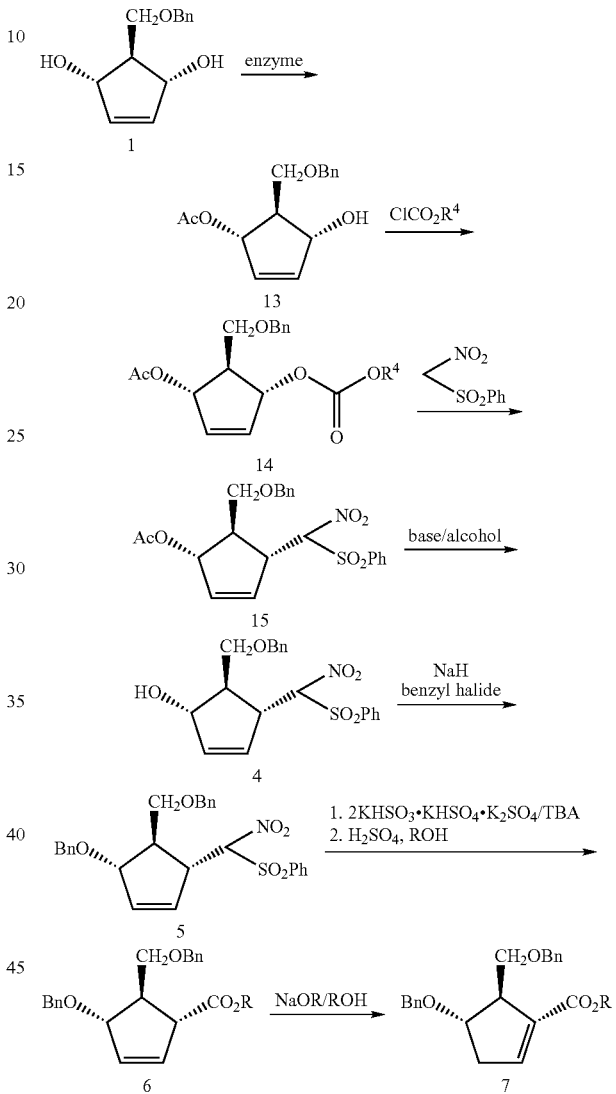

SCHEME 10

$R^4$ is $C_1$ to $C_6$ alkyl, benzyl, phenyl, or phenyl substituted by $C_1$ to $C_6$ alkyl or $C_1$ to $C_6$ alkoxy In Process E(b), the ester of formula 7 is prepared using alternative synthetic methods. One embodiment of Process E(b) is depicted in Scheme 10. The diol of formula 1 is selectively acetylated using a hydrolase enzyme, such as Lipase PS-30 or Pancreatin to generate enantiomerically enriched monoacetate compound of formula 13. Here again, the enzyme can be immobilized on a support. The acetylation reaction can be carried out in an organic solvent such as mixture of heptane:methyl tert-butyl ether. Preferably, the enantiomeric excess of the product, the monoacetate of formula 13, is at least 96% ee, more preferably at least 98% ee.

The monoacetate of formula 13 can be converted to the alkyl carbonate of the formula 14, wherein $R^4$ is preferably $C_1$ to $C_6$ alkyl, benzyl, phenyl, or phenyl substituted by $C_1$ to $C_6$ alkyl, for example, by treatment with an activated alkyl carbonic acid derivative, such as methyl chloroformate, dimethyl carbonate, etc. Preferably, the conversion is accomplished with methyl chloroformate and a tertiary amine base, e.g., pyridine, in an inert solvent, preferably DCM.

The alkyl carbonate of formula 14 can then be coupled with phenylsulfonylnitromethane to provide a compound of formula 15. The coupling is preferably catalyzed by a Pd(0) catalyst, e.g., tetrakis(triphenylphosphine)palladium, tris(dibenzylideneacetone)dipalladium(0), bis(dibenzylideneacetone)palladium(0).CHCl$_3$, in a solvent, e.g., THF, with a tertiary amine base, such as triethylamine. The compound of formula 15 is treated with a base, e.g., potassium carbonate in MeOH, to remove the acetate group and provide the compound of formula 4. The secondary alcohol moiety can be protected as a benzyl ether group by reacting the compound of formula 4 with a benzyl halide, e.g., benzyl bromide, preferably in the presence of a strong non-nucleophilic base, e.g., sodium hydride, to give the compound of formula 5. The compound of formula 5 can be converted to the ester of formula 7 by the methods already described in Process E(a).

Process E(c)

formula 8 serves as the chiral starting material. The cyclopentane epoxide of formula 8 can be prepared according to the procedure described in U.S. Pat. No. 5,206,244, the disclosure of which is incorporated by reference as if fully set forth herein. An allylic alcohol of formula 9 is prepared by heating the epoxide of formula 8 with a strong non-nucleophilic base, e.g., lithium hexamethyldisilazide in THF. After aqueous workup, the allylic alcohol of formula 9 can be used without further purification. Here again, the allylic alcohol moiety can be converted to the alkyl carbonate group, wherein $R^4$ is preferably $C_1$ to $C_6$ alkyl, benzyl, phenyl, or phenyl substituted by $C_1$ to $C_6$ alkyl, for example, by treatment with an activated alkyl carbonic acid derivative, such as methyl chloroformate, dimethyl carbonate, etc to give the alkyl carbonate of the formula 10. In one embodiment, the allylic alcohol of formula 9 is stirred with methyl chloroformate and a tertiary amine base, preferably pyridine, in an inert solvent, e.g, DCM, to give a methyl carbonate. The crude alkyl carbonate can be directly coupled to phenylsulfonylnitromethane in THF to provide a compound of formula 5. The coupling of the alkyl carbonate compound is preferably catalyzed by a palladium (0) catalyst such as tetrakis(triphenylphosphine)palladium in THF with a tertiary amine base, e.g. triethylamine. The compound of formula 5 can be converted to the ester of formula 7 by the methods described in Process E(a).

Process E(d)

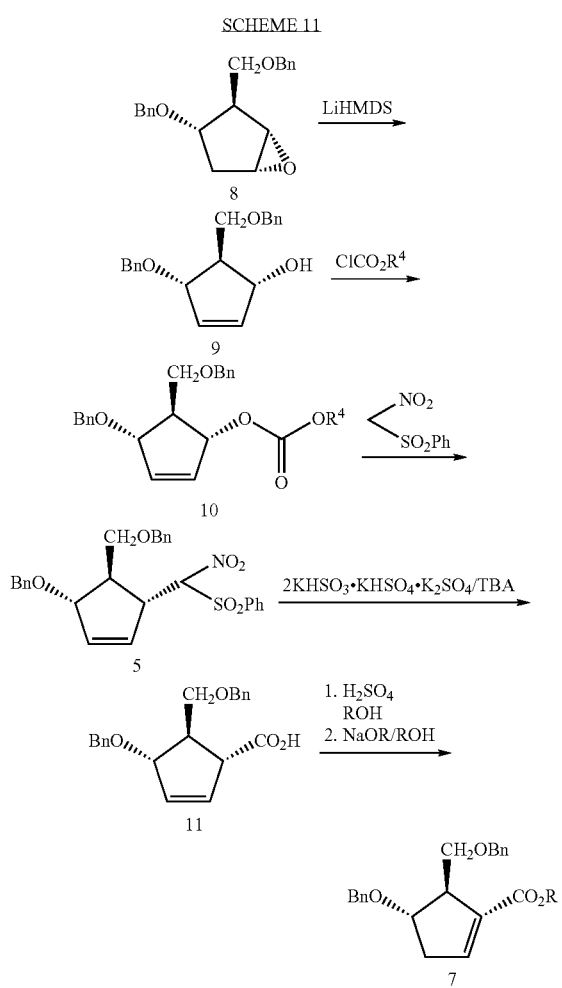

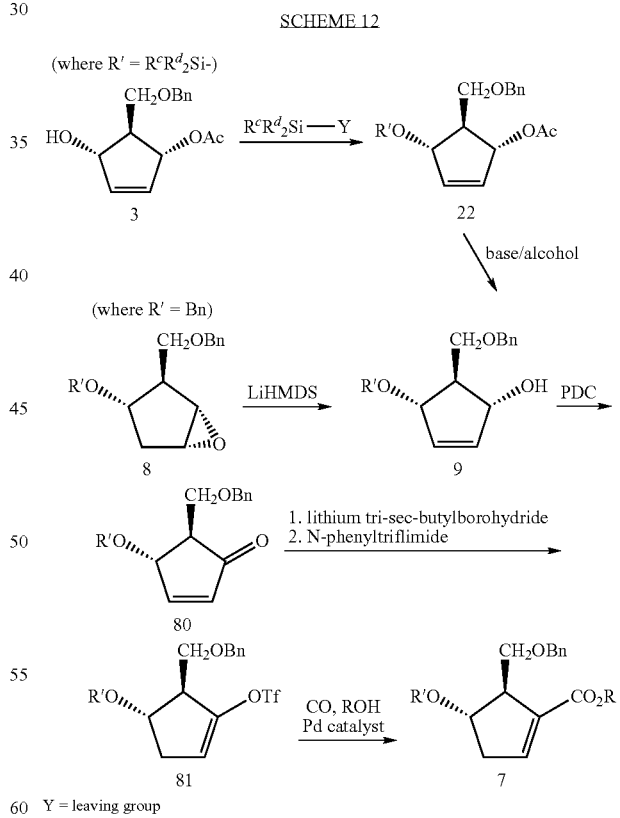

Y = leaving group

Alternatively, Process E(c) can be used to prepare the ester of formula 7 (where R is benzyl). One embodiment of Process E(c) is depicted in Scheme 11. A cyclopentane epoxide of the Process E(d) can also be used to prepare the ester of formula 7, wherein R' is benzyl or silyl. Embodiments of Process E(d) are depicted in Scheme 12. In the process, the allylic alcohol of formula 9 is oxidized with an oxidizing reagent such as pyridinium dichromate (PDC), pyridinium chlorochromate, manganese dioxide, and the like, in an inert solvent, preferably DCM, to afford the cyclopentenone of formula 80. The cyclopentenone is reduced with hydride reagents that selectively effect a 1,4-hydride addition. Suitable reducing conditions include, for example, treatment with lithium tri-sec-butylborohydride in THF. The intermediate from the reduction is trapped with an activated trifluoromethanesulfonic acid derivative such as N-phenyltriflimide to provide the triflate of the formula 81. An alkyloxycarbonyl group is then inserted onto the ring using, for example, a palladium catalyzed carbonyl insertion reaction to prepare the ester of formula 7. Preferably the insertion reaction is performed in a mixture of DMF and an alcohol, preferably MeOH, with an excess amount of a tertiary amine base, such as triethylamine. A preferred catalyst for the reaction is a palladium (0) catalyst, e.g., tetrakis(triphenylphosphine)palladium.

In embodiments of Process E(d) wherein R' is a benzyl or substituted benzyl group, the allylic alcohol 9 can be prepared as described in Process E(c) from the cyclopentane epoxide of formula 8. In embodiments of Process E(d) wherein R' is a silyl ether protecting group, the allylic alcohol can be prepared in a two-step procedure from the monoacetate of formula 3 (which can be prepared as described in Process E(a)). The secondary alcohol moiety of the monoacetate of formula 3 is reacted with a silylating reagent $R^cR^d_2SiY$, wherein Y is a suitable leaving group, e.g., chloride, triflate, and the like. In one embodiment, the secondary alcohol is protected as a tert-butyldimethylsilyl ether using tert-butyldimethylsilyl chloride (TBSCl) in the presence of pyridine in an inert solvent such as DCM to give a compound of formula 22. The acetyl group of the compound of formula 22 is hydrolyzed by using a base e.g., potassium carbonate in an alcohol solvent, to give the allylic alcohol of formula 9.

Process F

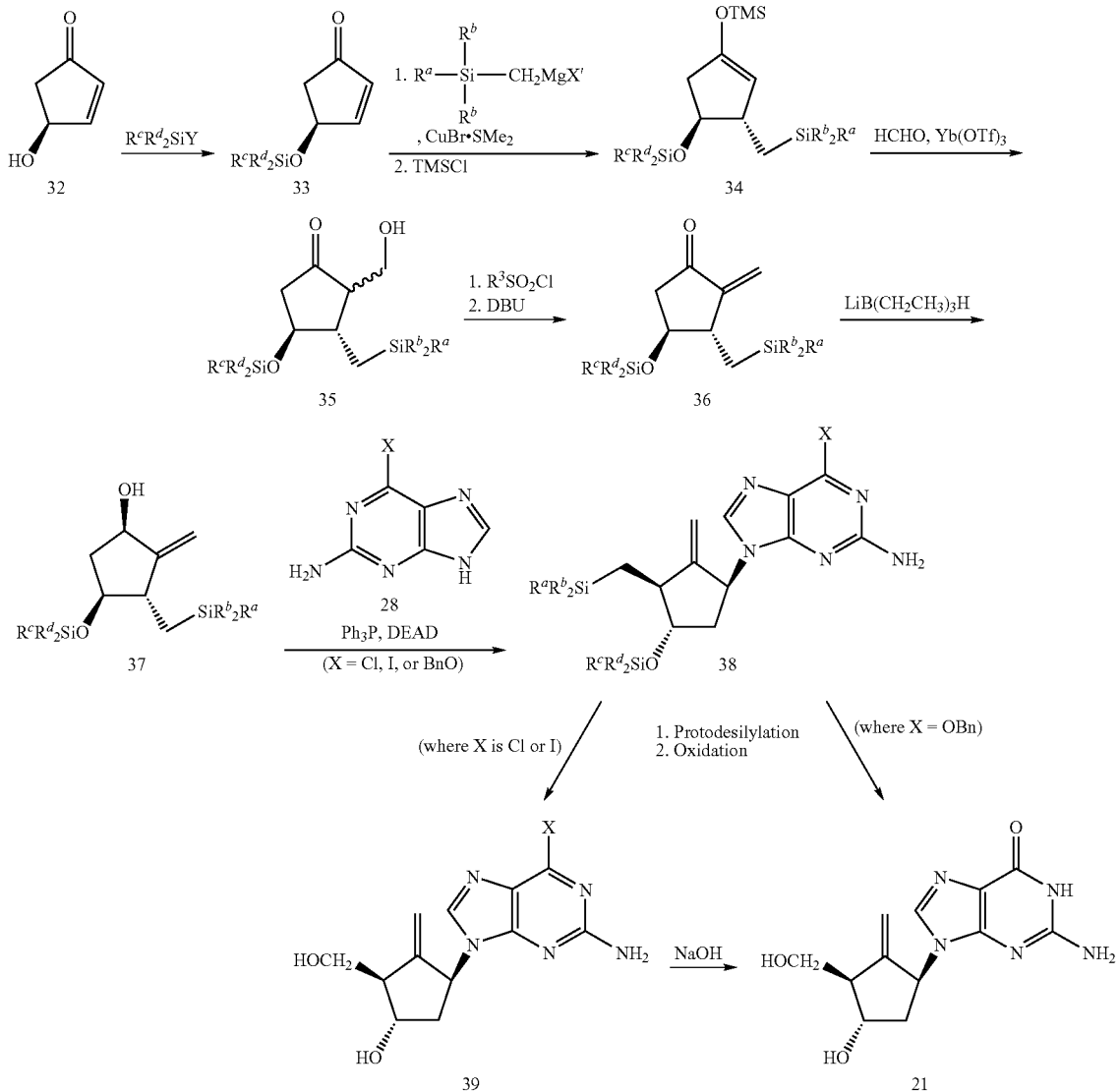

SCHEME 13

Process F of the invention includes preparation of a suitably substituted cyclopentanol of formula 37, and coupling of the cyclopentanol with a guanine precursor, such as 2-amino-6-iodopurine under Mitsonobu conditions to give a carbocyclic nucleoside, the methylene compound of formula 38. The methylene compound of formula 38 can then be elaborated to the compound of formula 21. One embodiment of Process F is depicted in Scheme 13.

The cyclopentenone of formula 32 (also known as 4-(S)-hydroxy-2-cyclopenten-1-one) serves as starting material for Process F. The cyclopentenone can be obtained according to procedures described in Khanapure, S.; Najafi, N.; Manna, S.; Yang, J.; Rokash. J. *J. Org. Chem.*, 1995, 60, 7448. The alcohol moiety of the cyclopentenone of formula 32 can be protected as a silyl ether using the silylating reagent of the formula $R^cR^d{}_2SiY$ (wherein $R^c$, $R^d$ and Y are as defined in Process E and E(d)). For example, the alcohol moiety of the cyclopentenone of formula 32 can be protected as a tert-butyldimethylsilyl ether using tert-butyldimethylsilyl chloride (TBSCl), a tertiary amine base such as N,N-dimethylethylamine, and a catalytic amount of 4-N,N-dimethylaminopyridine in an inert solvent such as DCM to give the cyclopentenone of formula 33. The cyclopentenone of formula 33 can then be treated with a Grignard reagent prepared from a (halomethyl)dialkylphenylsilane of the formula $R^aR^b{}_2SiCH_2X'$ (wherein $R^a$ and $R^b$ are as described above for Process A, and X' is Cl, Br, or I) and magnesium, in the presence of copper (I) salt such as Cu (I) bromide dimethylsulfide complex. In one embodiment, (chloromethyl)-dimethylphenylsilane is used to prepare the Grignard reagent. A trimethylsilylating reagent such as chlorotrimethylsilane (TMSCl) can be used to treat the intermediate enolate to form the silyl enol ether of formula 34. The resulting silyl enol ether is hydroxymethylated, for example by using aqueous formaldehyde in the presence of a Lewis acid, e.g., $Yb(OTf)_3$, $La(OTf)_3$, $Pr(OTf)_3$, $Nd(OTf)_3$, $Sm(OTf)_3$, $Eu(OTf)_3$, $Eu(OTf)_3$, $Gd(OTf)_3$, $Dy(OTf)_3$, $Ho(OTf)_3$, or $Er(OTf)_3$ in THF to give the compound of formula 35.

The compound of formula 35 can be dehydrated by reacting the compound with a sulfonylating agent of the formula $R^3SO_2Cl$, wherein $R^3$ is $C_1$ to $C_6$ alkyl, trifluoromethyl, phenyl, or substituted phenyl (substituted by $C_1$ to $C_6$ alkyl and/or $C_1$ to $C_6$ alkoxy) in the presence of a tertiary amine base, e.g., triethylamine, and then eliminating the intermediate sulfonate by addition of a strong base, preferably DBU, to give the methylene compound of formula 36. Preferably the sulfonylating agent used is methanesulfonyl chloride. The carbonyl moiety of the methylene compound of formula 36 can be reduced by hydride reagents that selectively effect 1,2-reduction of the carbonyl group and provides the allylic alcohol with high diastereoselectivity. These hydride reagents include sodium borohydride, zinc borohydride, lithium aluminum hydride, diisobutylaluminum hydride, sodium borohydride-cerium chloride, lithium triethylborohydride, lithium 9-BBN hydride, 9-BBN pyridine, borane-sulfide complex, 5,5-diphenyl-2-methyl-3,4-propan-1,3,2-oxazaborolidine (Corey Reagent), lithium tri-tert-butoxyaluminum hydride, sodium cyanoborohydride, lithium tri-sec-butyl borohydride (L-Selectride®), sodium bis(2-methoxyethoxy)aluminum hydride (Red-Al®), diisobutylaluminum chloride and borane-tetrahydrofuran complex. The carbonyl group can be reduced, for example, with lithium triethylborohydride in THF to give the crude allylic alcohol of formula 37 in 95% yield in an 8:1 diastereomeric ratio. The crude product is purified, for example, using silica gel chromatography to isolate the desired diastereomer of the allylic alcohol of the formula 37.

The allylic alcohol of formula 37 is condensed with 2-amino-6-iodopurine (purine compound of formula 28, wherein X is I) under Mitsonobu conditions. Alternatively, other guanine precursors, such as 2-amino-6-chloropurine and 2-amino-6-O-benzyloxypurine can be used in the condensation. Preferred Mitsonobu conditions include treatment of the allylic alcohol with about 1.3 molar equivalents each of triphenylphosphine, DEAD, and 2-amino-6-iodopurine in THF. The product of the Mitsonobu reaction, the methylene compound of formula 38, can be further purified by, for example, silica gel chromatography.

The methylene compound of formula 38 can be converted to the compound of formula 21. In one conversion method, the dialkylphenylsilane moiety of the methylene compound of formula 38 can be converted to a hydroxy moiety by oxidation procedures analogous to those used in Processes B and C. The silyl ether protecting group is simultaneously hydrolyzed during these procedures. For example, the methylene compound of formula 38 can be treated with tetrafluoroboric acid-dimethyl ether complex in DCM. After addition of potassium bicarbonate and potassium fluoride, the intermediate silanol from this reaction is oxidized with hydrogen peroxide to provide the compound of formula 39. The two reactions can be conveniently performed using a one-pot procedure. The 6-iodo group can be hydrolyzed by heating the compound of formula 39 with aqueous base such as a 2 N sodium hydroxide solution. After neutralization the aqueous solution can be heated with decolorizing carbon and allowed to crystallize to furnish the purified compound of formula 21.

Process G

SCHEME 14

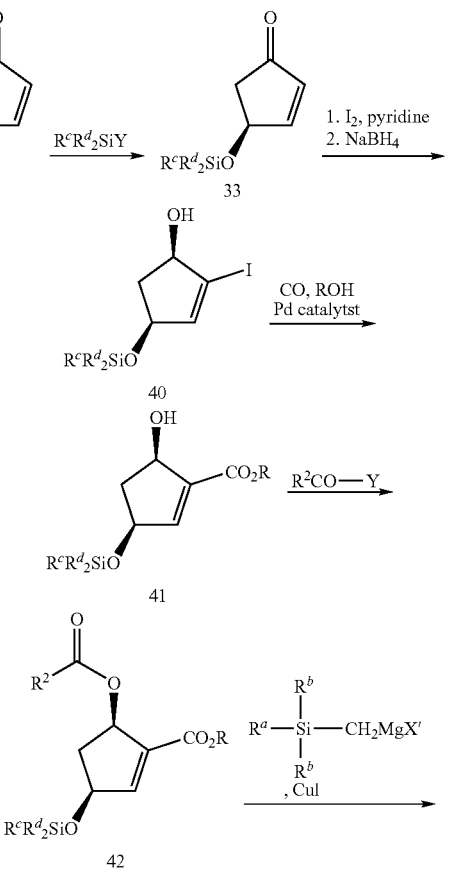

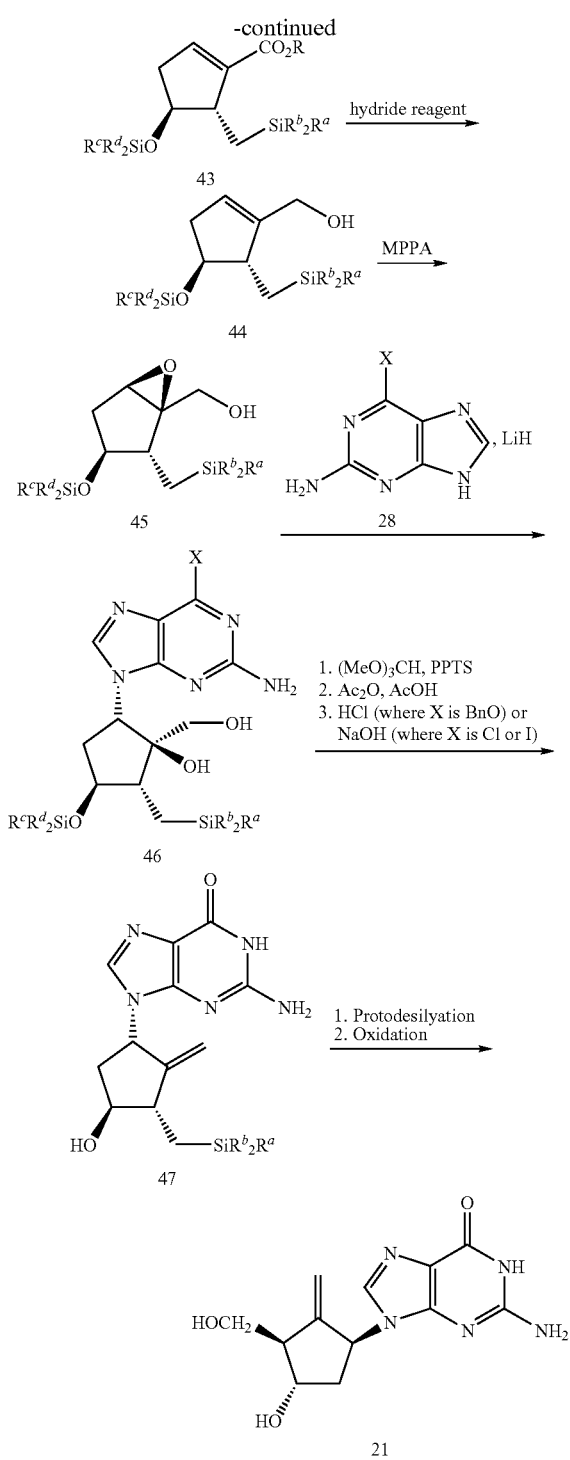

cyclopentenone intermediate is reduced, with a hydride reagent, for example, sodium borohydride in MeOH, to form the iodo compound of formula 40 in >98% de The iodo compound of formula 40 can then be subjected to a carbonyl insertion reaction. For example, the allylic alcohol of formula 40 is reacted with carbon monoxide and an alcohol ROH wherein R is $C_1$ to $C_4$ alkyl or benzyl to form the ester of formula 41. Preferably, the insertion reaction is conducted with carbon monoxide and MeOH in the presence of a tertiary amine base, e.g., triethylamine, in a pressurized sealed reaction vessel. The reaction is preferably catalyzed by a palladium catalyst, e.g., dichloro bis(triphenylphosphine)palladium. The crude product from the insertion reaction can be purified by column chromatography to provide pure compound of formula 41.

The secondary alcohol of the compound of formula 41 is acylated by treatment with an activated acid derivative of the formula $R^2C(O)$—Y, and a base, preferably lithium hexamethyldisilazide. While other activated acid derivatives can be used (including alkyl and aryl acid derivatives) to form the acyl intermediate 42, adamantane carbonyl chloride is preferably used (i.e., $R^2$=adamantane). With this preferred reagent, a more crystalline intermediate is obtained that is more easily purified and handled. The intermediate of formula 42 is subjected to allylic displacement by treatment with the Grignard reagent prepared from a (halomethyl)dialkylphenylsilane of the formula $R^aR^b{}_2SiCH_2X'$ (wherein $R^a$ and $R^b$ are as described above for Process A, and X' is Cl, Br, or I) and magnesium, in the presence of copper (I) salt such as Cu (J) iodide. In one embodiment, (chloromethyl)-dimethylphenylsilane is used to prepare the Grignard reagent. The reaction product, the compound of formula 43, can be used in the next synthetic step without further purification.

The compound of formula 43 can be reduced with a hydride reagent, such as diisobutylaluminum hydride in toluene, to provide the allylic alcohol of formula 44. Epoxidation of the crude allylic alcohol of the formula 44 provides the cyclopentane epoxide having the formula 45. For example, in one epoxidation method, the allylic alcohol is treated with a peracid, e.g., magnesium monoperoxyphthalate (MPPA) in MeOH, to prepare the cyclopentane epoxide. Using this method, the cyclopentane epoxide of formula 45 is of sufficient diastereomeric purity to be used in the next synthetic step without further purification.

In the next step of Process G, the cyclopentane epoxide of formula 45 is converted to the compound of formula 46 by condensation with an alkali metal salt, e.g. lithium salt, of 2-amino-6-O-benzyloxypurine in a dipolar aprotic solvent, e.g., DMF. The lithium salt, for example, can be generated by reaction of 2-amino-6-benzyloxypurine with lithium hydride. The crude product from the condensation reaction can be purified by recrystallization from a suitable solvent, e.g., MeOH, to provide the pure compound of formula 46. Here again similar to Processes B and C, alkali metal salts of other guanine precursors, e.g., 2-amino-6-chloropurine, 2-amino-6-iodopurine, can be used in place of 2-amino-6-benzyloxypurine to couple with the cyclopentane epoxide of the formula 45.

The diol moiety of the compound of formula 46 is then converted to an alkene. For example, the conversion to the methylene compound of formula 47 can be performed using a two step procedure. The compound of formula 46 is treated with an orthoformate derivative, preferably trimethylorthoformate, and a catalytic amount of an acid such as TFA or PTSA, or acid catalyst such as PPTS. The excess orthoformate reagent is evaporated, and the resulting mixture of dioxolanes is heated with acetic anhydride. The methylene compound of formula 47 is obtained after evaporation of the acetic anhydride and acid workup, which treatment also hydrolyzes the 6-O-benzyloxy group. In embodiments of Process G, Process G includes preparation of a cyclopentane epoxide of the formula 45, and coupling of the cyclopentane epoxide with a guanine precursor to give a carbocyclic nucleoside, the compound of formula 46. The compound of formula 46 can then be converted by a series of synthetic steps to the compound of formula 21. One embodiment of Process G is depicted in Scheme 14.

In Process G, the cyclopentenone of formula 33 (prepared as described in Process F) can be iodinated, for example, by treatment with iodine solution. Preferably, the reaction solvent is a mixture of DCM and pyridine. The resulting iodo wherein X is Cl or I, the 6-halo group on the purine can be hydrolyzed using hydroxide solution, e.g., NaOH.

The phenyldimethylsilylmethyl group of the methylene compound of formula 47 can be converted to a hydroxymethyl moiety, for example, by the procedures described in Processes B, C, and F. For example, in one embodiment, the methylene compound of formula 47 can be treated with tetrafluoroboric acid-dimethyl ether complex in DCM to provide the silanol intermediate. Treatment of the silanol intermediate with potassium bicarbonate, potassium fluoride, and hydrogen peroxide provides the compound of formula 21.

Process H

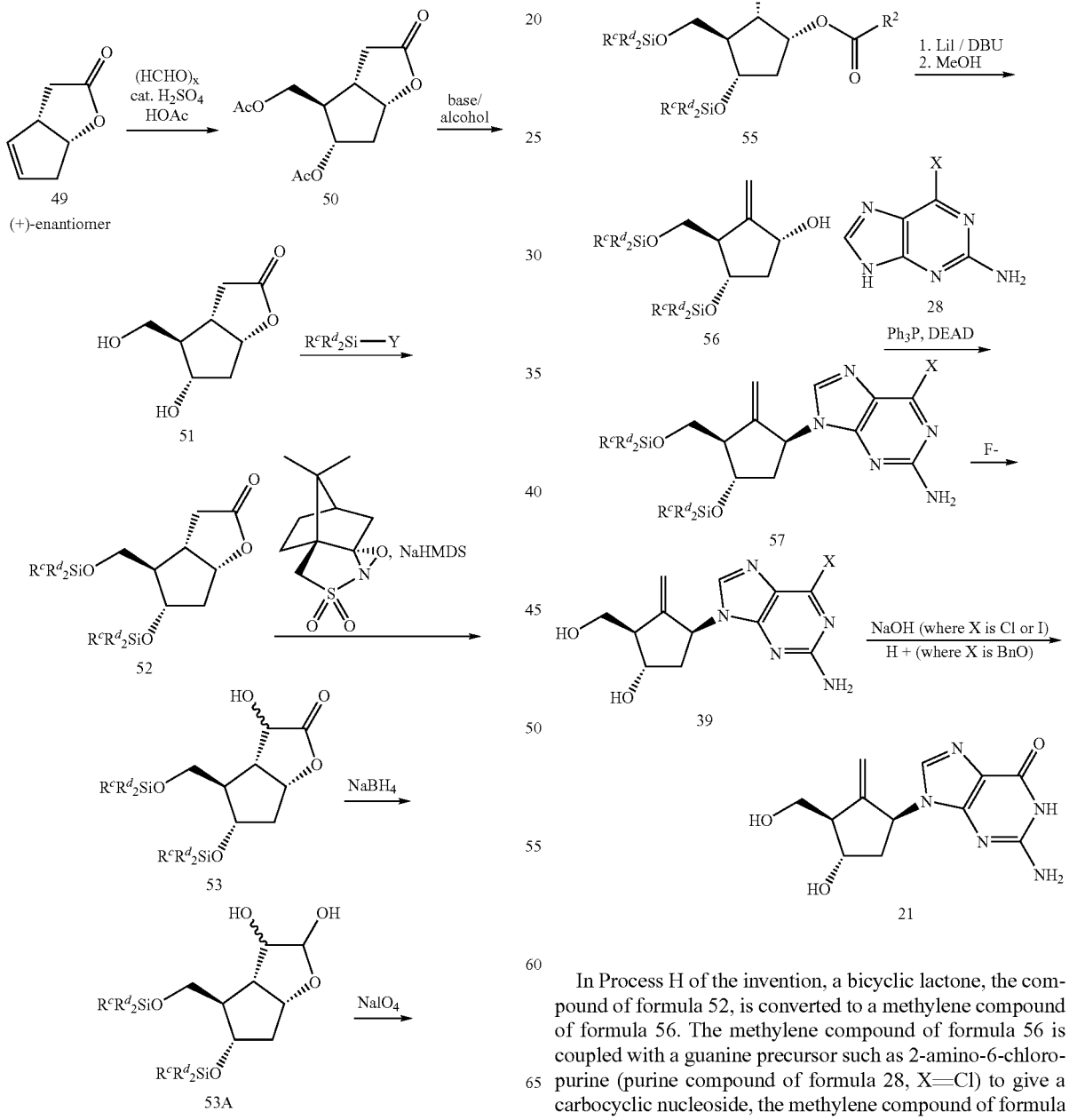

In Process H of the invention, a bicyclic lactone, the compound of formula 52, is converted to a methylene compound of formula 56. The methylene compound of formula 56 is coupled with a guanine precursor such as 2-amino-6-chloropurine (purine compound of formula 28, X=Cl) to give a carbocyclic nucleoside, the methylene compound of formula 57. The methylene compound of formula 57 is subsequently converted to the compound of formula 21 by deprotection and hydrolysis steps. Embodiments of Process H are depicted in Scheme 15.

The compound of formula 52 can be treated with the oxaziridine reagent, e.g., (1S)-(+)-(10-Camphorsulfonyl)oxaziridine, and a strong non-nucleophilic base, preferably sodium bis[trimethylsilyl]amide (NaHMDS) in THF, to generate a compound of formula 53. After quenching the reaction with, for example, MeOH, the compound of formula 53 can be directly reduced by treatment with a suitable hydride reagent such as sodium borohydride in MeOH, to reduce the lactone moiety and provide the compound of formula 53A. The vicinal diol of the compound of formula 53A can be oxidatively cleaved by treatment with an oxidizing agent such as sodium periodate, potassium permanganate, or ruthenium oxide. The resulting aldehyde containing intermediate 53B can then be reduced with a suitable hydride reagent, e.g., sodium borohydride, to generate the diol of the formula 54.

The primary alcohol moiety of the diol of formula 54 can be selectively converted to a suitable leaving group, preferably using a sulfonylating reagent having the formula $R^3SO_2Cl$, wherein $R^3$ is $C_1$ to $C_6$ alkyl, trifluoromethyl, phenyl, or substituted phenyl (substituted by $C_1$ to $C_6$ alkyl or $C_1$ to $C_6$ alkoxy). For example, the diol of formula 54 is treated with p-toluenesulfonyl chloride (TsCl), a tertiary amine base such as pyridine, and a catalytic amount of 4-N,N-dimethylaminopyridine to convert the primary alcohol to a tosylate group. The secondary alcohol is protected as an ester by acylation with an acylating agent to provide the compound of formula 55. Preferably the secondary alcohol is protected by an acyl group of the formula $R^2C(=O)-$, wherein $R^2$ is alkyl, aryl, arylalkyl, any of which can be substituted. Most preferably, $R^2$ is methyl so that the acyl protecting group in the compound of formula 55 is acetyl. A preferred acylating agent is an acylating agent of the formula $R^2C(O)Y$, wherein Y is a leaving group. For example, the acylating agent can be an anhydride, acid chloride, and the like.

The compound of formula 55 is treated with an iodide salt, e.g., lithium iodide, and a strong base such as DBU to effect elimination of the intermediate iodide. Hydrolysis of the acyl ester is carried out by direct addition of MeOH to the basic reaction mixture, providing the methylene compound of formula 56. The methylene compound of formula 56 can be further purified by, for example, silica gel chromatography.

The methylene compound of formula 56 serves as a suitable compound for coupling with a guanine precursor (purine compound of formula 28, wherein X is Cl, Br or benzyloxy). For instance, the methylene compound of formula 56 is treated under Mitsonobu conditions with 2-amino-6-chloropurine to give the methylene compound of formula 57. Preferably the Mitsonobu conditions comprise treatment with DEAD and triphenylphosphine. The methylene compound of formula 57 can be further purified by, for example, silica gel chromatography.

The conversion of the methylene compound of formula 57 to the compound of formula 21 can be completed by deprotection of the silyl ether moieties and hydrolysis of the 6-X group on the purine moiety. The two silyl ether moieties are cleaved by treatment with fluoride ion (e.g., tetralkylammonium fluoride reagent such as tetrabutylammonium fluoride in THF) to give the compound of formula 39. In embodiments of the process wherein the purine moiety has a 6-chloro or iodo group, the 6-halo group is hydrolyzed by heating the compound of formula 39 with aqueous base or acid, preferably aqueous base, e.g., 2 N sodium hydroxide solution, to give the compound of formula 21. In embodiments of the process where X is a 6-O-benzyloxy group, conversion to the 6-oxo group can be performed using acidic conditions, e.g. 2 N HCl. The compound of formula 21 can be further purified by, for example, silica gel chromatography.

In Process H, the homochiral bicyclic lactone of formula 49 can be used as starting material for the preparation of the compound of formula 52, and can be prepared as described in Corey et al. *J. Med. Chem.* 1993, 36, 243. The bicyclic lactone of formula 49 can be treated with paraformaldehyde in a mixture of glacial acetic acid and sulfuric acid to add formaldehyde across the double bond. This treatment yields a diacetate of formula 50. The diacetate of formula 50 is subsequently stirred with a base such as potassium carbonate in an alcohol solvent, e.g., MeOH, to hydrolyze the acetate moieties and provide the diol of the formula 51. The alcohol moieties of the diol of formula 51 can be protected as silyl ether groups by treating the diol with a silylating reagent of the formula $R^cR^d_2SiY$ (wherein $R^c$, $R^d$, and Y are as described above in the description of Process E) to provide the compound of formula 52. In one embodiment of Process H, the silylating reagent is tert-butyldimethyl chloride (TBSCl).

Process I

SCHEME 16

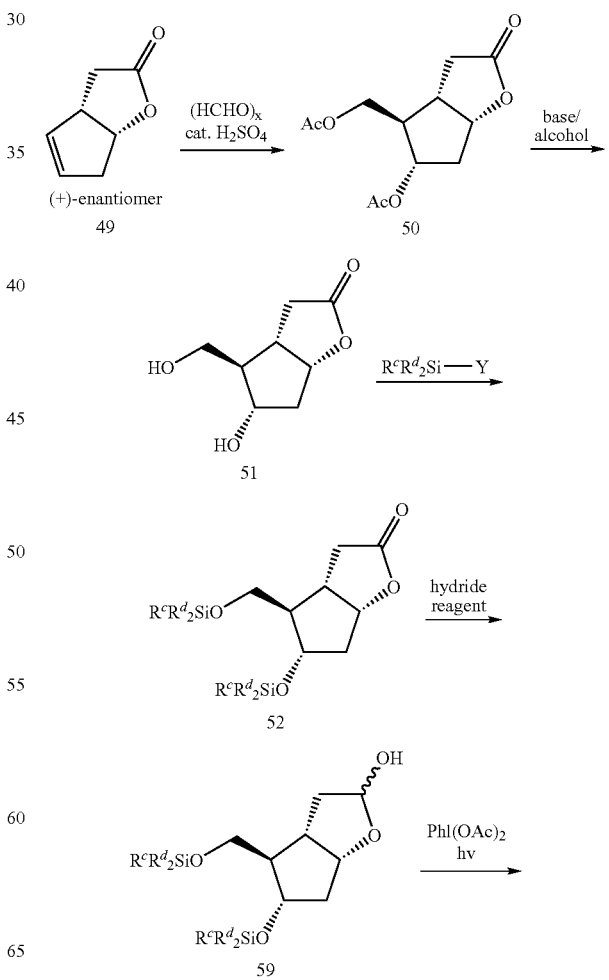

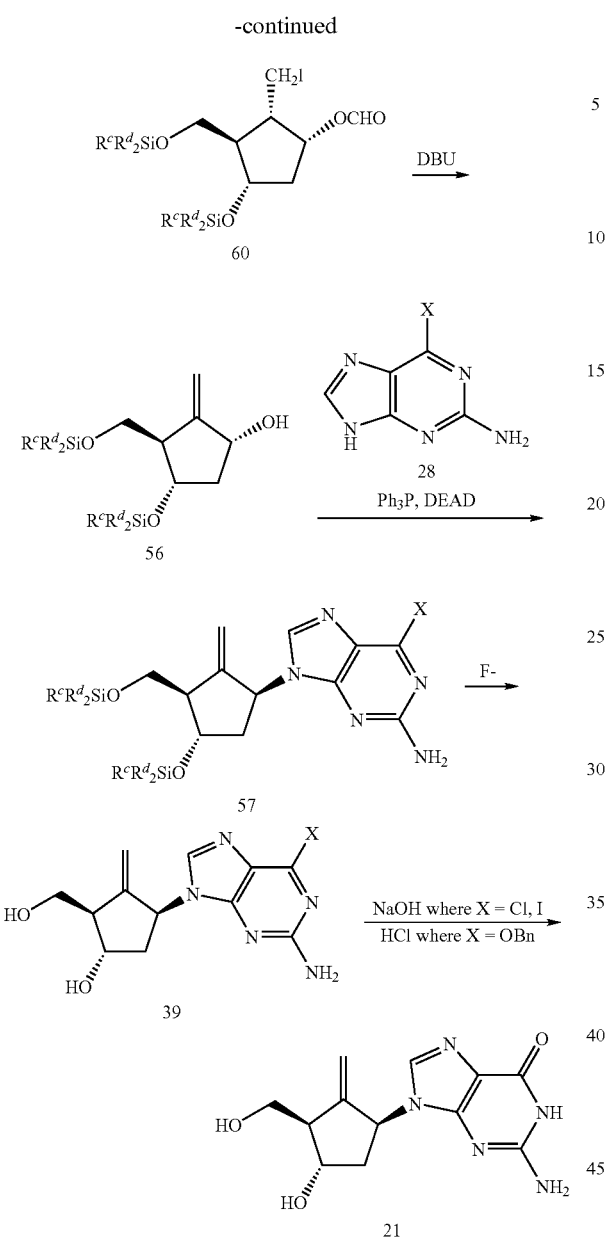

the lactol of formula 59, is subsequently cleaved using an oxidizing agent, such as iodobenzene diacetate under UV irradiation (sun lamp) in DCM to give the iodide compound of formula 60. The iodide compound of formula 60 can be treated with a strong base such as DBU to effect elimination of the iodide moiety with removal of the formate ester upon water workup to yield the methylene compound of formula 56.

The methylene compound of formula 56 can be coupled to a guanine precursor, such as 2-amino-6-iodopurine (purine compound of formula 28 wherein X is I), under reaction conditions such as those described for the conversion of the methylene compound of formula 56 to the compound of formula 57 described above in Process H. The resulting carbocyclic nucleoside, the compound of formula 39, can be converted to the compound of formula 21 by methods such as those used in the Process H.

Process J

SCHEME 17

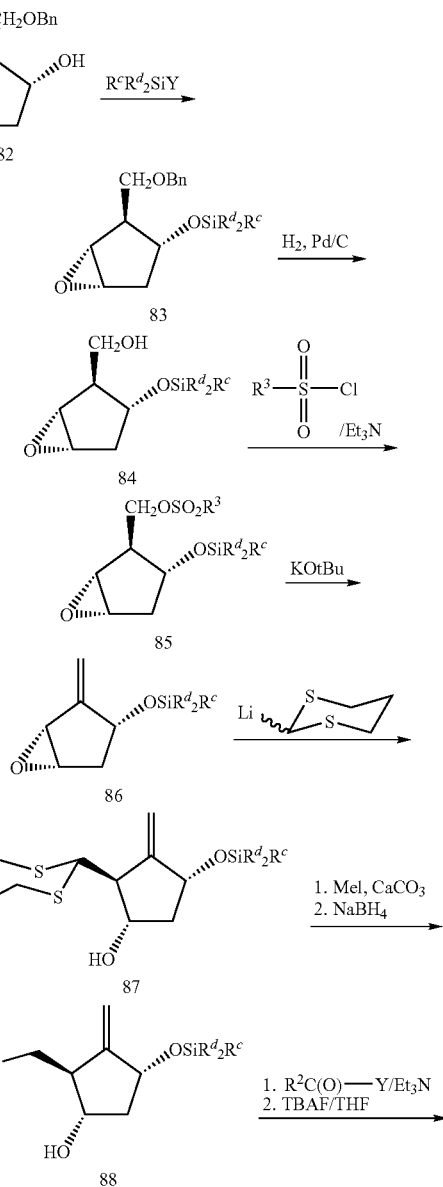

Similar to Process H of the invention, Process I of the invention comprises preparation of a methylene compound of formula 56 from the homochiral bicyclic lactone intermediate, the compound of formula 52. The coupling of the methylene compound of formula 56 to a guanine precursor (purine compound of formula 28), and subsequent conversion of the resultant carbocyclic nucleoside to the compound of formula 21 are analogous to the methods used in Process H as well. The preparation of the methylene compound of formula 56 from the compound of formula 52, however, is achieved by different synthetic methods than those used in Process H. One embodiment of Process I is depicted in Scheme 16.

In Process I, the lactone moiety of the compound of formula 52 is reduced under controlled reaction conditions to provide the lactol of formula 59. For instance, the compound of formula 52 can be treated with a hydride reagent, e.g., diisobutylaluminum hydride in toluene at 25° C. to achieve reduction to the lactol oxidation state. The reduction product,

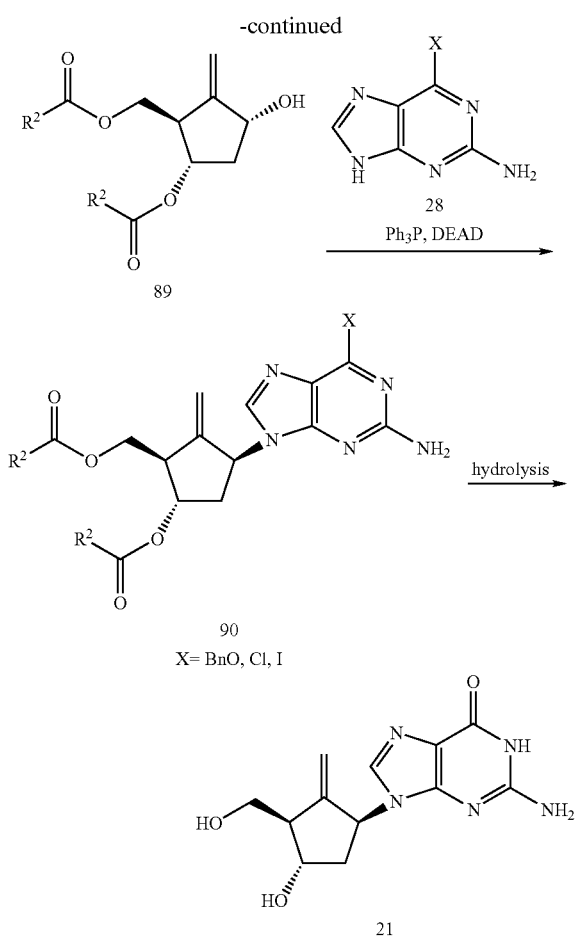

Process J of the invention depicts another approach for the preparation of the compound of formula 21 (Scheme 17). Process J includes formation of a methylene compound of formula 89, and subsequent coupling of the methylene compound with a guanine precursor, e.g., 2-amino-6-iodopurine, using Mitsonobu conditions to yield a carbocyclic nucleoside intermediate, the methylene compound of formula 90. The protecting groups of 90 are removed and the X group is hydrolyzed to provide the compound of formula 21.

The methylene compound of formula 89 is prepared from the cyclopentane epoxide of formula 82, prepared as described in Example 1 of U.S. Pat. No. 5,206,244. The secondary alcohol moiety of 82 is protected as a silyl ether having the formula $R^cR^d{}_2SiO$— wherein $R^c$ and $R^d$ are as described above in the description of Process E. In one embodiment, the secondary alcohol of 82 is protected as a tert-butyl dimethylsilyl ether. The primary alcohol is unmasked by catalytic reduction of the benzyl group of 83 with, for example, palladium on carbon to give the compound of formula 84. The compound of formula 86 is prepared by a base catalyzed elimination procedure. In the first step of the procedure, the primary alcohol of 84 is converted into a suitable leaving group, preferably using a sulfonating reagent having the formula $R^3SO_2Cl$, wherein $R^3$ is as described above in Process F, to give the compound having the formula 85. A strong base, e.g., potassium t-butoxide, in a suitable solvent, e.g. THF, is then used to effect the elimination of alkyl or (substituted) phenylsulfonic acid to provide the exocyclic methylene moiety in the compound of formula 86.

A hydroxymethyl moiety is then installed on the cyclopentane ring adjacent to the exocyclic methylene moiety in the compound of formula 86 to give the compound of formula 87. To efficiently effect this transformation, a regioselective 1,2-addition of a carbon nucleophile to the epoxide of the compound of formula 86 is preferably conducted. Preferably, the carbon nucleophile is a carbanion of 1,3-dithiane, e.g., lithium salt of 1,3-dithiane, that adds to the allylic position to provide the compound of formula 87. The lithium salt of 1,3-dithiane can be generated with a strong non-nucleophilic base, e.g., n-butyl lithium, lithium diisopropylamide, lithium hexamethylsilazide, and the like in an ethereal solvent, e.g., THF. A chelating agent such as 1,4-diazabicyclo[2.2.2]octane (DABCO) is preferably added to enhance the efficiency of the process. The reaction is preferably carried out below 25° C., more preferably below about −15° C. to ensure high regioselectivity. Preferably, the regioselectivity of the addition is >10:1, more preferably >15:1.

The dithianylmethyl group of the compound of formula 87 is readily converted to an alcohol by a hydrolysis reaction followed by a reduction reaction. The hydrolysis to an intermediate aldehyde is carried out, for example, by stirring a mixture of compound of formula 87 with calcium carbonate and iodomethane in aqueous acetonitrile. Other methods for hydrolyzing dithioacetals are well known in the art and include methods recited in Greene, T. W.; Wuts, P. G. M. *Protecting Groups in Organic Synthesis 2nd Edition*; Wiley and Sons: New York, 1991, pp. 199-201. The intermediate aldehyde can be reduced with a suitable hydride reagent, e.g., sodium borohydride, to provide the compound of formula 88.

The compound of formula 88 is converted to a compound suitable for coupling with a protected guanine derivative, by acylation of the alcohol groups. Acyl groups of the formula $R^2C(=O)$— wherein $R^2$ is as described above for Process H can serve as protecting groups. Preferably, $R^2$ is methyl so that the acyl group is acetyl. The silyl ether group is then cleaved using fluoride ion, e.g., tetrabutylammonium fluoride, to give the methylene compound of formula 89.

The compound of formula 89 is coupled to a suitable guanine precursor, e.g., 2-amino-6-iodopurine, to provide a carbocyclic nucleoside intermediate, the methylene compound of formula 90. In alternative embodiments, 2-amino-6-chloropurine or 2-amino-6-benzyloxypurine can be used as the guanine precursor. The methylene compound of formula 90, can be converted to the compound of formula 21 by suitable hydrolysis methods. For example, the ester groups can be cleaved by treatment with an alkali metal alkoxide, e.g. sodium methoxide, and the 6-halo group can be hydrolyzed by heating in aqueous base. In embodiments of the process wherein 2-amino-benzyloxypurine is used as a guanine precursor, the 6-benzyloxy group is hydrolyzed using acid, e.g., HCl.

Process K

Resin Purification

Another aspect of this invention is the use of a resin adsorption process for isolation and purification of the compound of formula 21 or intermediates thereof. This process employs a crude mixture comprising compound 21 or a mixture comprising entacavir intermediate(s) and other reagents, such as, for example, an oxidative mixture resulting from the treatment of an intermediate for compound 21 with hydrogen peroxide in an oxidative desilylation reaction in the presence of KF and $KHCO_3$. Compound 21 is soluble in water at 2.2 mg/mL and more preferably below 1.5 mg/mL. Compound 21 and related compounds are adsorbed on the resin specifically while inorganic salts pass through. The resin bed is then washed with water to remove any additional salts and compound 21 or a compound related thereto (e.g., such as an intermediate or precursor) is eluted from the resin via washing with an organic solvent. In one embodiment, the organic solvent comprises a mixture of MeOH and water, preferably 40-60% MeOH:40-60% water, more preferably 45-55% MeOH:45-55% water, even more preferably 50:50 MeOH and water, as 50% MeOH provides optimal separation of compound 21 or compound related thereto which is then concentrated and crystallized to obtain a pure compound. As use herein, by "pure" it is meant a compound having greater than or equal to 97%, or more preferably 99%, purity. Most preferred is a compound wherein all impurity peaks are less than 0.1 area percent as determined by high performance liquid chromatography (HPLC).

Resins suitable for use in this adsorption process are hydrophobic resins with selectivity for non-polar molecules. In one embodiment, the resin is styrene-based. More preferably, the styrene-based resins are brominated to provide for greater strength and abrasion resistance. Exemplary resins with such properties include, but are not limited to, SP207 Sepabeads, SP700 Sepabeads, Diaion HP20, Diaion SP70, Diaion SP825, Diaion SP850, Diaion HP2MG methacrylate, AMBERLITE XAD4, AMBERLITE XAD7HP, AMBERLITE XAD16, and AMBERLITE XAD1600. In a preferred embodiment, SP207 is used as the resin as this resin exhibits abrasion resistance, long-term recycling utilization, and the ability to withstand extremes of organic solvent conditions, temperatures, and pH, to be particularly useful in purification of compound 21 and compounds related thereto.

The following examples further illustrate the present invention, but of course, should not be construed as in any way limiting its scope.

EXAMPLE 1

Process for the Preparation of [1S-(1α,3α,4β)]-2-Amino-1,9-dihydro-9-[4-hydroxy-3-(hydroxymethyl)-2-methylenecyclopentyl]-6H-purin-6-one (21)

Preparation of (1α,4α,5α)-7,7-Dichloro-4-(dimethylphenylsilyl) bicyclo[3.2.0]hept-2-en-6-one (63)

A 3-L three necked flask equipped with a mechanical stirrer, a 500-mL addition funnel, a thermometer and an argon inlet was charged with phenyldimethylchlorosilane (153.6 g, 0.90 moles) and anhydrous THF (320 mL). The flask was then cooled to –78° C. To this stirring solution, was added sodium cyclopentadienide (441 mL, 2.04 M in THF, 0.90 moles) over a period of one hour. The reaction mixture was stirred for about two hours and then it was allowed to warm to about 0° C. over a period of two hours. At this time the reaction was assumed to be complete. The reaction was quenched by addition of cold water (~150 mL) and allowed to warm to ~15° C. The mixture was diluted with hexanes (~100 mL) and transferred to a separatory funnel. The organic layer was separated and the aqueous layer was extracted with hexanes (200 mL). The combined organic layer was washed with brine (200 mL), dried over anhydrous magnesium sulfate, filtered, and concentrated in vacuo to give the crude diene as dark brown oil (177 g, ~98% yield). The crude diene was used without further purification in the next reaction.

A 3-L three necked flask equipped with a mechanical stirrer, 500-mL addition funnel, thermometer, and argon inlet was charged with diene of the above reaction (176.5 g, 0.88 moles) and hexanes (600 mL). The mixture was cooled to about –10° C. and dichloroacetyl chloride (173 mL, 1.80 moles) was added over the course of five minutes. To this stirred mixture a solution of $Et_3N$ (251 mL, 1.80 moles) in hexanes (400 mL) was added over a period of one hour. The resulting mixture was stirred for about three hours at 0-4° C. and then at ambient temperature for about ten hours to complete the reaction. The reaction was quenched by addition of water (400 mL). After stirring for about 30 minutes at room temperature, the solution was transferred to a separatory funnel and the organic layer was separated. The aqueous layer was extracted with hexanes (300 mL). The combined organic layer was washed with water (250 mL), sodium bicarbonate (5%, 250 mL) and water (500 mL). The combined filtrate was concentrated in vacuo. The resulting dark oil was further dried under high vacuum to give 307 g of the crude title compound.

Preparation of trans-5-(Dimethylphenylsilyl)-2-(hydroxymethyl)-2-cyclopentene-1-carboxylic acid (64)

A 3-L three necked flask equipped with a mechanical stirrer, a 500-mL addition funnel, a thermometer and an argon inlet was charged with the above obtained 63 (211 g, 0.68 moles), tert-butanol (348 g), water (710 mL), and $Et_3N$ (343 g, 3.39 moles). The reaction mixture was heated to reflux for 3 hours. The reaction mixture was cooled to ~10° C. and potassium carbonate (300 g, 2.17 moles) was added over 30 minutes. After 30 minutes, sodium borohydride (13.6 g, 0.359 moles) was added in portion-wise. After 1 hour the cooling bath was removed and the reaction mixture was allowed to warm slowly. The reaction mixture was carefully quenched with water (800 mL). The pH was adjusted to 3.0 and the resulting mixture extracted with EtOAc (800 mL). The organic extract was concentrated in vacuo. The resulting dark oil was further dried under high vacuum to give 185 g of the racemic title compound.

Preparation of (1R,5S)-5-(Dimethylphenylsilyl)-2-(hydroxymethyl)-2-cyclopentene-1-carboxylic acid, (1R,2S)-2-amino-1-(4-nitrophenyl)-1,3-propanediol (1:1) salt (65A)

A 3-L three necked flask equipped with a mechanical stirrer, addition funnel, thermometer and argon inlet was charged with 64 (185 g, 0.67 moles), absolute ethanol (925 g) and R,R-(–)-2-amino-1-(4-nitrophenyl)-1,3-propanediol (102 g, 0.483 moles), and heated to 50° C. The solution was seeded with the salt 65A and left at 40° C. for 5 hours. The resulting crystals were filtered on a Buchner funnel and washed with ethanol. The solid was dried to give the title compound in ~28.3% yield (94 g) from sodium cyclopentadienide. The product has a purity of 98 AP and 99% ee.

Preparation of (1R,5S)-5-(Dimethylphenylsilyl)-2-(hydroxymethyl)-2-cyclopentene-1-carboxylic acid methyl ester (66)

To a 2-L 3-necked round bottomed flask equipped with a mechanical stirrer, an addition funnel and a thermometer, was charged 65A (390 g, 0.8 mole) and MeOH (800 mL). The reaction mixture was cooled to about 0° C. Concentrated sulfuric acid (123 g, 1.2 moles) was slowly added to the reaction flask with stirring. After addition of the acid, the reaction mixture was stirred for about 12 hours at room temperature to complete the reaction. After completion of the reaction, the reaction mixture was concentrated in vacuo to remove about 500 mL of MeOH. The residue was diluted with EtOAc (600 mL) and water (1000 mL). The mixture was transferred to a separatory funnel and the organic layer was separated. The aqueous layer was extracted with EtOAc (600 mL). The combined organic layer was washed with saturated sodium bicarbonate (500 mL), water (500 mL), brine (500 mL) and concentrated in vacuo to afford the crude title compound (224 g) as a brown oil.

Preparation of [1R-(1α,2α, 3β,5α)]-3-(Dimethylphenylsilyl)-6-oxabicyclo[3.1.0]hexane-1,2-dimethanol (72)

To a 5-L 3-necked round bottomed flask equipped with a mechanical stirrer, an addition funnel and a thermometer, was charged activated molecular sieves (224 g) and DCM (1000 mL) under an atmosphere of argon. The solution was cooled to about −30° C. DIPT (18 g, 0.08 moles) was added to the solution and the mixture stirred at −30° C. for about 20 minutes. Titanium (IV) isopropoxide (18.2 mL, 0.064 moles) was then added to the reaction mixture. The reaction mixture was stirred at −30° C. for about 20 minutes.

Compound 66 (224 g, 0.8 moles) in DCM (500 mL) was charged to the reaction mixture via syringe at −30° C. The reaction mixture was stirred at −30° C. for about 20 minutes. TBHP (308 mL, 5 M/decane, 1.6 moles) was added to the reaction mixture using an addition funnel, keeping the reaction temperature between −20° C. to −30° C. After complete addition of TBHP, the reaction mixture was stirred between −20° C. to −30° C. for about 2 hours. After the reaction was complete, the excess peroxide was quenched by addition of aqueous sodium bisulfite (250 g of sodium bisulfite in 500 mL of water). After the addition of sodium bisulfite, the mixture was stirred for about 30 minutes and filtered through a pad of diatomaceous earth (CeliteHyflo®). The filtrate was transferred to a separatory funnel and the aqueous layer was separated. The organic layer was washed with saturated sodium bicarbonate solution (1000 mL) and then water (500 mL). The organic layer was concentrated in vacuo to give the crude epoxide (276 g) as an oil.

To a 3-L 3-necked round bottomed flask equipped with a mechanical stirrer and a thermometer was charged the above obtained epoxide (276 g, 0.8 moles) and IPA (800 mL) under an atmosphere of argon. The resulting solution was cooled to about 0° C. in an ice bath and to it was added solid sodium borohydride (68 g, 1.6 moles) in portions. After the addition was complete, the cooling bath was removed and the reaction mixture was stirred for about 16 hours to complete the reaction. After completion of the reaction, the excess borohydride was quenched by adding the reaction mixture to a solution of saturated ammonium chloride (2000 mL). After the borohydride was completely quenched, the reaction mixture was extracted with EtOAc (1200 mL). The organic layer was washed with water (500 mL), brine (500 mL), and concentrated in vacuo to afford the title compound (251 g) as light yellow oil.

Preparation of [1S-(1α,2β,3α,4β)]-1-[2-Amino-6-(phenylmethoxy)-9H-purin-9-yl]-4-(dimethylphenylsilyl)-2-hydroxy-2,3-cyclopentanedimethanol (73, X=BnO)

To a 3-L 3-necked round bottomed flask equipped with a mechanical stirrer and a thermometer, was charged 2-amino-6-benzyloxypurine (193 g, 0.8 moles), lithium hydroxide monohydrate (33.6 g, 0.64 moles) and 72 (251 g, 0.8 moles) in DMF (800 mL). The mixture was heated to 80° C. and stirred for about 20 hours. After completion of the reaction, the reaction mixture was cooled to room temperature and extracted with EtOAc (3000 mL). The organic layer was washed with brine (1500 mL). The organic layer was washed with citric acid (1000 mL), brine (1000 mL) and concentrated in vacuo to furnish crude triol (330 g) as a thick brown oil. The product was crystallized from EtOAc-hexanes to give the title compound (~225 g) as a solid crystalline material.

Preparation of [1S-(1α,3α,4β)]-2-Amino-9-[4-(dimethylphenylsilyl)-3-(hydroxymethyl)-2-methylenecyclopentyl]-1,9-dihydro-6H-purin-6-one (71)

A 2.0-L 3-necked round bottomed flask, oven dried and equipped with a mechanical stirrer, an addition funnel, a temperature probe, and argon inlet, was charged with 73 (77.5 g, 0.1493 moles), pyridinium p-toluenesulfonate (1.875 g, 0.007465 mole), and DCM (371 mL) under an argon atmosphere. The resulting slurry was stirred and cooled to 0° C. Diethoxymethyl acetate (122 mL, 0.7465 moles) was added slowly over a period of about 15 minutes. The reaction mixture was warmed to room temperature over a period of one hour. After the complete consumption of the starting material, the resulting brown reaction mixture was slowly added to a stirring saturated solution of sodium bicarbonate (775 mL). The resulting mixture was extracted with EtOAc (1000 mL). The organic layer was concentrated in vacuo to afford a mixture of dioxolanes as a viscous brown oil (~125 g) which was transferred to a 2-L 3-necked round bottomed flask. The flask was additionally charged with acetic anhydride (279 mL, 2.96 moles) and heated at about 120° C. for 30 hours. After the complete consumption of the starting material, the reaction mixture was cooled ~65° C., and MeOH (745 mL) was added. The reaction mixture was stirred while maintaining the temperature at 65° C. for 40 minutes. Water (5-10 mL) was added to the reaction mixture, and the reaction mixture was cooled to about 45° C. Concentrated HCl (220 mL) was added and the mixture was reheated at 65° C. for 4 hours. The mixture was cooled to ~20° C., and extracted with a hexane-tert-butyl methyl ether (9:1) mixture (1500 mL). The organic extract was concentrated in vacuo. The residue was transferred to a 3-L 3-necked flask and heated to 55° C. and at this temperature, 10 N NaOH (413 mL) was added to adjust the pH of the solution to about 12.8. The reaction mixture was heated to 75° C. and stirred at that temperature for ~4 hours. Concentrated HCl (30 mL) was slowly added to the reaction mixture to adjust the pH to 7 and the reaction mixture was allowed to cool to 20° C. over a 4 hour period. The slurry was filtered and the cake washed with a mixture of cold MeOH-water (3:7) (200 mL), followed by water (800 mL), and tert-butyl methyl ether (150 mL). The light brown colored crude product was dried to afford the title compound (37.7 g, 64%).

Preparation of [1S-(1α,3α, 4β)]-2-Amino-1,9-dihydro-9-[4-hydroxy-3-(hydroxymethyl)-2-methylenecyclopentyl]-6H-purin-6-one (21)

A 2-L 3-necked round bottomed flask, oven dried and equipped with a mechanical stirrer, an addition funnel, temperature probe, and argon inlet, was charged with compound 71 (34.1 g, 86.2 moles), acetic acid (40.4 mL, 8 eq) and acetic acid-boron trifluoride complex (38 mL). The reaction mixture was heated to 95° C., stirred for 4 hours and then cooled to room temperature. The reaction mixture was diluted with MeOH (200 mL) and quenched with aqueous KOH (10 N, ~220 mL) to adjust the pH to about 9.5. Potassium bicarbonate (17.9 g) followed by aqueous hydrogen peroxide (30 wt.

%, 39 g) was added to the solution. The resulting solution was warmed to 70° C. and stirred for 10 hours. The reaction was cooled to 5-10° C. Sodium bisulfite (16.2 g) was added portion-wise over 30 minutes. The reaction mixture was concentrated in vacuo to remove most of the MeOH. The resulting yellow semi-solid was cooled to −5° C. and concentrated HCl (~55 mL) added to adjust the pH to 0.15. The resulting solution was extracted with EtOAc (500 mL) and aqueous KOH (10 N, ~48 mL) added to adjust the pH to ~11. The solution was stirred for 1 hour and then the pH was adjusted to ~7 with HCl (4 mL). The reaction mixture was stirred at room temperature for 1 hour and at ~5° C. for 3 hours. The solid was collected by filtration and dried under high vacuum for 16 hours. The solid was redissolved in water (600 mL) at 90° C. The clear solution was cooled to ~60-55° C. and seeded with 21. The solution was allowed to cool to room temperature for 5 hours. The resulting white crystalline solid was collected by filtration and dried under vacuum at 50° C. for 16 hours to afford the title compound (12.9 g).

EXAMPLE 2

Process for the Preparation of [1S-(1α,3α,4β)]-2-Amino-1,9-dihydro-9-[4-hydroxy-3-(hydroxymethyl)-2-methylenecyclopentyl]-6H-purin-6-one (21)

Preparation of (1R,5S)-5-(Dimethylphenylsilyl)-2-[(1-methoxy-1-methylethoxy)methyl]-2-cyclopentene-1-methanol (75)

To a 1-L 3-necked round bottomed flask equipped with a mechanical stirrer and a thermometer was charged 66 (29.6 g, 0.1 moles, obtained as described in Example 1) and toluene (50 mL) under an atmosphere of argon. The resulting solution was cooled to ~0° C. in an ice bath and 2-methoxypropene (95 mL, 1.0 mole) was added. Pyridinium p-toluenesulfonate (0.5 g, 0.002 moles) was added at 0° C. and the resulting mixture was stirred at 0° C. for 10 minutes. The cooling bath was removed and the reaction mixture was stirred at room temperature for 1.5 hours. After completion of the reaction, the reaction mixture was cooled to −78° C. Triethylamine (27 mL, 0.2 moles) was added to keep the reaction mixture in a basic environment. LAH (1 M in THF, 0.1 moles) was added at −78° C. The cooling bath was removed after 30 minutes and the reaction was allowed to warm to ambient temperature. The reaction mixture was stirred at room temperature for 1-2 hours. The reaction mixture was cooled to 0° C. and 2 N NaOH (20 mL) was added. After this addition, the reaction mixture was stirred for 30 min and filtered. The pad was washed with DCM (400 mL). The organic filtrate was washed with brine (100 mL) and concentrated in vacuo to afford the title compound (35 g) as a light yellow oil.

Preparation of (4S,5R)-4-(Dimethylphenylsilyl)-5-[(phenylmethoxy)methyl]-1-cyclopentene-1-methanol (76)

To a 250-mL 3-necked round bottomed flask equipped with a mechanical stirrer and a thermometer was charged 75 (35 g, 0.1 moles) and THF (60 mL) under an atmosphere of argon. NaH (6 g, 60%, mineral oil suspension, 0.15 moles) was added to the solution. The mixture was heated at 60° C. for 1 hour and then cooled to room temperature. Benzyl bromide (23.8 mL, 0.2 moles) and tetrabutylammonium bromide (10 g, 0.03 moles) were added to the suspension. The reaction mixture was heated at 70° C. for 6 hours and then the reaction mixture was cooled to room temperature. 1,9-diazabicyclo [5.4.0]undecen-7-ene (45 mL, 0.2 moles) was added and heated at 50° C. for 45 min. The reaction mixture was cooled to room temperature, quenched with 1N HCl to pH ~1 and extracted with a mixture of EtOAc-hexane (250 mL). The organic layer was washed with water (500 mL), brine (100 mL) and concentrated in vacuo to afford the title compound (42 g) as a brown oil.

Preparation of [1R-[(1α,2α,3β,5α)]-3-(Dimethylphenylsilyl)-2-((phenylmethoxy)methyl]-6-oxabicyclo[3.1.0]hexane-1-methanol (77)

To an oven dried, 1-L 3-necked round bottomed flask equipped with a mechanical stirrer, a temperature probe, and an argon line was charged activated molecular sieves (35 g) and DCM (160 mL) under an atmosphere of argon. The solution was cooled to about −30° C. DIPT (2.34 g, 0.01 moles) followed by titanium (IV) isopropoxide (2.36 mL, 0.008 moles) was added to the reaction mixture. The reaction mixture was stirred at −30° C. for about 20 minutes. Crude 76 (42 g, ~0.1 moles) in DCM (40 mL) was added to the reaction mixture and stirred for about 30 minutes. TBHP (40 mL, 0.2 moles) was added to the reaction mixture at −30° C. After complete addition of TBHP, the reaction mixture was stirred at −30° C. for about 5 hours to complete the reaction. The excess peroxide was quenched with aqueous sodium bisulfite (20 g). The mixture was filtered through a Buchner Funnel with a pad of diatomaceous earth (Hyflo Celite®). The filtrate was washed with saturated $NaHCO_3$, solution (100 mL) and brine (100 mL). The organic layer was concentrated in vacuo to give the crude title compound (60 g, >100% material balance) as an oil.

Preparation of [1R-(1α,2α,3β,5α)]-5-[2-Amino-6-(phenylmethoxy)-9H-purin-9-yl]-3-(dimethylphenylsilyl)-1-hydroxy-2-[(phenylmethoxy)methyl]cyclopentanemethanol (78A, X=BnO)

To a 1-L 3-necked round bottomed flask equipped with a mechanical stirrer and a thermometer, was charged 2-amino-6-benzyloxypurine (24 g, 0.1 moles), lithium hydride (0.48 g, 0.06 moles) and DMF (40 mL). The mixture was heated at 60° C. for about 1 hour under an atmosphere of argon. 77 (60 g, 0.1 moles) in 20 mL DMF was added. The reaction temperature was heated at 105° C. for 5 hours, cooled to room temperature and diluted with EtOAc (600 mL). The organic layer was washed with brine (300 mL), 1 M citric acid (150 mL), and $NaHCO_3$ solution (100 mL). The organic layer was concentrated in vacuo to furnish crude title product (60 g) as an oil. It was crystallized from EtOAc and hexane to give 23 g of the title compound as a crystalline solid.

Preparation of [1S-(1α,3α,5β)]-2-Amino-9-[4-(dimethylphenylsilyl)-2-methylene-3-[(phenylmethoxy)methyl]cyclopentyl]-1,9-dihydro-6H-purin-6-one (79)

A 100-mL 3-necked round bottomed flask, oven dried and equipped with a mechanical stirrer, an addition funnel, a temperature probe, and an argon inlet was charged with 78A (12.2 g, 0.02 moles), pyridinium p-toluenesulfonate (0.25 g, 0.001 moles) and DCM (20 mL) under argon atmosphere. The resulting solution was stirred at room temperature and DEMA (16 mL, 0.1 moles) was added. The reaction mixture was stirred at room temperature for one hour. After the complete consumption of the starting material, the resulting reaction mixture was quenched with a saturated solution of NaHCO$_3$ (100 mL) and extracted with EtOAc (100 mL). The organic layer was washed with brine (2×50 mL) and concentrated in vacuo to afford the mixture of dioxalanes as a viscous oil which was transferred to a 250-mL 3-necked round bottomed flask, equipped with a mechanical stirrer, a condenser, a temperature probe, and an oil bath. Acetic anhydride (20 mL, 0.2 moles) was added to this flask and the resulting mixture was heated at 120° C. for 15 hours. After the complete consumption of the starting material, the reaction mixture was cooled ~60° C. and MeOH (50 mL) was added. An HCl solution (50 mL, 6 N) was added to the reaction mixture and the temperature was raised to 70° C. and stirred for a total of 6 hours. During this period, a 50% MeOH/water solution was added (50 mL). The reaction mixture was concentrated to remove the excess MeOH (150 mL MeOH) on a rotary evaporator. The resulting mixture was warmed to ~50-55° C. NaOH (10 N) was added to adjust the pH of the solution to ~6.5. The resulting suspension was stirred at ~50° C. for 1 hour, and then cooled to 28° C. over the course of 2 hours. The solid was filtered, washed with 1:2 MeOH/water (80 mL), water (100 mL), and dried to afford the title compound (7.65 g).

Alternative Conversion of 78A to 79

78A (5 kg) was dissolved in toluene (17 L) and treated with pyridium-p-toluenesulfonate (110 g, 0.05 mole) and DEMA (5.33 kg, 4 moles) at ambient temperature, affording a diastereomeric mixture of orthoesters. The reaction was quenched with aqueous NaOH while maintaining the pH above 7.5. Tert-butyl methyl ether (70 L) was added and the layers were separated. The product rich organic layer was dried by azetropic distillation to a moisture content of less than 0.1%. Butylated hydroxytoluene (10 kg) and glacial acetic acid (0.99 kg, 2 equiv) and acetic anhydride (10.9 kg, 13.2 equiv) were added to the toluene reaction mixture, and the mixture was heated to 120 to 125° C. for several hours.

At the end of the olefination reaction, the reaction mixture was added to MeOH (80 L) and aqueous HCl (6 N, 21.6 L) while maintaining the temperature at less than 35° C. The reaction mixture was heated to 60 to 65° C. to effect deacetylation. The reaction mixture was cooled to ambient temperature and washed with heptane (2×35 L) to remove butylated hydroxytoluene. The layers were separated and the product rich aqueous methanolic layer was heated to 55 to 65° C. Water (14.2 L) was added, followed by cooling to ambient temperature over 2 to 5 hours to effect crystallization of the hydrochloride salt of 79. The crystal slurry was filtered and washed with water (2×20.2 L) and heptane (2×30 L). The filter cake was dried to 60 to 65° C. to a moisture content of less than 3.5% (3.64 kg, 85.6% yield).

The above hydrochloride salt of 79 (1.26 kg) was suspended in MeOH (13 L) and heated to 55 to 65° C. to achieve complete dissolution. The apparent pH of the solution was adjusted to 5.4 to 6.4 with 1 N NaOH (about 1.5 L) while maintaining the temperature at 50 to 65° C. The free base slurry was held at 50 to 65° C. for an additional 60 to 90 minutes then slowly cooled to ambient temperature over 90 to 120 minutes. More water (about 1.5 L) was added over 45 to 60 minutes, and the pH was readjusted to 5.5 to 6.4 with 1 N HCl or NaOH. The crystal slurry was filtered and washed with 1:1 MeOH:water (2.6 L), followed by water (2.8 L) and finally heptane (4 L). The cake was dried in a vacuum oven at 60-65° C. to a moisture content of less than 1% (1.03 kg, 85%).

The free base can be reprecipitated from toluene/heptane to afford highly purified 79 in 90-93% yield, 99% AP, 99.0+% potency.

Alternative Conversion of 78A to Methanesulfonate Salt of 79

Under nitrogen, a solution of 78A (50.0 g, 82.06 mmol), triisopropyl orthoformate (46.85 g, 246.2 mmol) and TFA (7.02 g, 61.57 mmol) in toluene (300 ml) was stirred for one hour at room temperature. To this solution were added butylated hydroxytoluene (50 g), acetic anhydride (100 ml) and glacial acetic acid (4.93 g, 82.10 mmol) and the solution was heated to 120° C. After holding the reaction solution at 120° C. for 12.5 hours, the dark solution was cooled to room temperature and added to a cold (4° C.) solution of methanesulfonic acid (63.40 g, 659.70 mmol) in water (309 ml) at a rate to keep the temperature at 5-10° C. The reaction mixture was stirred for 15 minutes at 5-10° C. and MeOH (600 ml) was added at a rate to keep the temperature at 5-10° C. After stirring at 5-10° C. for 15 minutes, the reaction mixture was heated to 65° C. and held for 12 hours. After cooling to room temperature, the crude reaction mixture was washed with heptane (300 ml) and the layers separated. Additional MeOH (200 ml) was added to the product rich aqueous layer, and it was again extracted with heptane (300 ml). The reaction mixture was heated to 65° C. and water (500 ml) was added so as to keep the temperature at 65-55° C. to initiate crystallization of the methanesulfonate salt. The reaction solution was cooled to 10° C. and the solids were filtered, washed with water (200 ml), and dried at 50° C. under vacuum to afford 39.5 g of the methanesulfonate salt of 79 with AP of 99.6 and purity of 86.4%.

Preparation of [1S-(1α,3α,4β)]-2-Amino-1,9-dihydro-9-[4-hydroxy-3-(hydroxymethyl)-2-methylenecyclopentyl]-6H-purin-6-one (21)

To a 500-mL round bottomed flask, equipped with a magnetic stirrer, a nitrogen inlet, an oil bath, and a temperature probe was charged 79 (7.2 g, 4.7 mmols) and boron trifluoride-acetic acid complex (12.3 mL, 88.2 mmols). The reaction mixture was heated at ~70° C. for 3.5 hours, cooled to room temperature, and diluted with MeOH (80 mL)/H$_2$O (4 mL). The mixture was neutralized with KOH (10 N, ~40 mL) to pH ~9.6. Potassium bicarbonate (4.45 g, 44.1 mmols) was added to the solution and the resulting suspension was warmed up to ~60° C. Hydrogen peroxide (30 wt. % in water, 7.49 g, 73 mmols) was added, and then the reaction mixture was heated at 65° C. for 11 hours. The resulting mixture was cooled to 0° C. and sodium bisulfite (4.42 g) was added. MeOH was removed from the reaction mixture. The resulting mixture was diluted with water (50 mL) and acidified with HCl to pH ~0.5. The mixture was washed with methyl tert-butyl ether (100 mL) and neutralized with NaOH (10 N) to pH ~6.7. The resulting solution was cooled to room temperature and stirred for 6 hours to crystallize the product. The white crystalline solid was collected by filtration to afford 2.05 g of the title compound.

Alternate Conversion of 79 to 21 with Methanesulfonic Salt

A solution of 79 (30 g, 61.77 mmol) in methylene chloride (90 mL) was cooled and treated with methanesulfonic acid (90 mL). The resulting dark solution was stirred at 18-25° C. until the reaction was considered complete by an HPLC analysis. The reaction mixture was then quenched into a mixture of 45% aqueous KOH (155 mL) and MeOH (1.8 L) at 10 to 15° C. The resulting potassium methanesulfonate salt that formed was removed by filtration. The filtrate was concentrated, pH adjusted to 7.5 to 8.8 with glacial acetic acid (17 mL) and then treated with aqueous $KHCO_3$ (18.6 g in 82 mL of water, 3 equiv), aqueous KF (9.1 g in 25 mL of water, 2.5 equiv), and 30% aqueous hydrogen peroxide (19.8 mL, 3.1 equiv). The reaction mixture was then held at 60-70° C. until the formation of 21 was complete as determined by HPLC analysis.

Alternate Conversion of 79 to 21 via Compounds 110 and 114

Preparation of [1S-(1α,3α,4β)]-2-Amino-1,9-dihydro-9-[4-(dimethylhydroxylsilyl)-2-methylene-3-[(phenylmethoxymethyl]cyclopentyl]-6H-purin-6-one (110)

An aqueous solution of KOH (45 wt. %, 5.1 mL) was charged to a solution of compound 79 (4.85 g, 10 mmol) in NMP (49 mL). The mixture was heated at 50° C. for 12 hours. The reaction was cooled to room temperature. Water (75 mL) was charged while maintaining the reaction temperature below 35° C. The reaction mixture was cooled to 5-10° C., neutralized with aqueous HCl (6 N, ~10 mL) to pH~7, and then stirred at 0-5° C. for 0.5 hour. The solid was collected by filtration, and the wet cake washed with water (3×50 mL). The solid was dried under vacuum at (50° C.) for 24 hours to afford the title compound 110 (3.66 g in 87% yield).

Preparation of [1S-(1α,3α,4β)]-2-Amino-1,9-dihydro-9-[4-hydroxy-2-methylene-3-[(phenylmethoxymethyl]cyclopentyl]-6-purin-6-one (114)

A solution of KF (0.14 g, 0.23 mmol) in MeOH (1.4 mL) was added to a suspension of compound 110 (1.0 g, 2.3 mmol) in MeOH (8.4 mL) at room temperature. Potassium bicarbonate (0.47 g, 2.3 mmol) was charged to the resulting suspension. The mixture was stirred at 45° C. for 0.5 hour to form a clear solution and aqueous hydrogen peroxide (30 wt. %, 1.6 mL) was added. The reaction was heated at 45° C. for 3 hours, then cooled to 0-5° C. An aqueous solution of sodium bisulfite (10 wt. %, 5.0 mL) was added portion-wise in 0.5 hour. The mixture was slowly acidified with aqueous HCl (6 N, ~8 mL) to pH=0.45. The resulting solid was filtered off and the filtrate neutralized with aqueous NaOH (4 N, ~10 mL) to pH~8. The mixture was stirred at 0-5° C. for 1 hour. The solid was collected by filtration and dried under vacuum at 40° C. for 24 hours to afford the title compound 114 (0.66 g in 77% yield).

Preparation of [1S-(1α,3α,4β)]-2-Amino-1,9-dihydro-9-[4-hydroxy-3-(hydroxymethyl)-2-methylenecyclopentyl]-6H-purin-6-one (21)

To a solution of 114 (2.0 g, 5.44 mmoles) in methylene chloride (20 mL), cooled to −20° C., was added a methylene chloride solution of boron trichloride (1M, solution, 22 mL. 22 mmoles, 4.04 equivalents) over a period of ~30 minutes. During addition, the temperature was maintained at −19° to −23° C. After stirring for an additional 3 hours at −20° C., methanol (14 mL) was added to quench the reaction. The reaction mixture was stirred until HPLC showed no borane ester (~4 hours). MTBE (30 mL) was added, and the reaction mixture was stirred overnight at room temperature. The solid obtained was filtered, washed with MTBE (~5 mL), and dried under vacuum at room temperature to obtain 1.66 g of the hydrochloride salt of 21. The HCl salt (0.72 g, 2.29 mmoles) was taken in ~13 mL of water and heated to ~40° C. The pH was adjusted to ~7 with 2N NaOH. The thin slurry obtained was heated to 80-85° C. and treated with activated carbon (0.12 g). After 30 minutes at reflux, the hot mixture was filtered on a small Hyflo pad. The filtrate was cooled to room temperature over 3 hours and further stirred at 0° C. for 2 hours. The crystals obtained were filtered, washed with water, and dried under vacuum to obtain the compound of formula 21 (0.32 g, 44% overall yield from 114)

Isolation and Purification of Compound 21

Isolation of 21 was achieved by a resin adsorption procedure in which the oxidation mixture was diluted about 20 fold with water (about 1 mg of 21 per mL of diluted stream) and loaded onto SP207 resin (1 kg). The resin bed was first washed with water to remove salt, and compound 21 was eluted off the resin using 50:50 MeOH:water solution (about 20 L). The eluent, after a polish filter, was concentrated by distillation under vacuum at a temperature less than or equal to 55° C. to a batch volume of about 25 mL/g of 21. The resulting slurry was heated to 90° C. to form a clear solution. The clear solution was then slowly brought to ambient temperature to crystallize 21. After stirring the slurry for several hours at ambient temperature, 21 was filtered and dried under vacuum at ambient temperature until the moisture content of the product was between 6 and 7 wt. %. This procedure gave 21 in an average yield of 75 % from compound 79 and an HPLC area % of greater than 99.9.

EXAMPLE 3

Process for the Preparation of [1S-(1α,3α,4β)]-2-Amino-1,9-dihydro-9-[4-hydroxy-3-(hydroxymethyl)-2-methylenecyclopentyl]-6H-purin-6-one (21)

Preparation of [3aS-(3aα,5α,6β,6aα)]-5-(Dimethylphenylsilyl)hexahydro-6a-(hydroxymethyl)-2-oxo-2H-cyclopentoxazole-6-carboxylic acid methyl ester (67)

To a 500-mL round bottomed flask equipped with a magnetic stirrer and a thermometer was charged methyl carbamate (4.5 g, 60 mmol) and MeOH (40 mL) under an atmosphere of argon. The resulting solution was cooled to ~0° C. in an ice bath. Tert-butyl hypochlorite (6.52 g, 60 mmol) was added and the resulting mixture was stirred at 0° C. for 15 minutes. A methanolic solution of sodium hydroxide (2.44 g of sodium hydroxide (60 mmol in 40 mL MeOH) was added to this solution and the resulting mixture was stirred at room temperature for 1 hour. The mixture was directly concentrated in vacuo to give a white powdery reagent. To this reagent, isopropanol (53 mL), and water (26 mL) were added. The resulting mixture was stirred at room temperature until the mixture became a clear solution. This mixture was cooled to ~0° C. and then 66 (5.8 g, 20 mmol, obtained as described in Example 1) was added. The mixture was stirred for 10 minutes and then potassium osmate hydrate (280 mg) was added. The mixture was stirred at 0° C. for 1.5 hours followed by 12 hours at room temperature to complete the reaction. The reaction was quenched by addition of sodium thiosulfate (4 g) and stirred for 1 hour at room temperature. The mixture was filtered through a bed of diatomaceous earth (Celite®), and the filtrate diluted with water (100 mL) and extracted with ethyl acetate (3×50 mL). The organic layer was washed with water (3×50 mL), brine (50 mL) and dried over magnesium sulfate. The organic layer was concentrated in vacuo to afford the title compound (5.9 g in 85% yield).

Preparation of [3aS-(3aα,5α,6β,6aα)]-5-(Dimethylphenylsilyl)hexahydro-6a-(iodomethyl)-2-oxo-2H-cyclopentoxazole-6-carboxylic acid methyl ester (68)

To a 500-mL 3-necked round bottomed flask equipped with a magnetic stirrer and a thermometer was charged 67 (33.75 g, 96.7 mmol), DCM (100 mL) followed by pyridine (9.4 mL, 116 mmol) under an atmosphere of argon. The resulting mixture was cooled to 0° C. To this stirring mixture, trifluoromethanesulfonic anhydride (19.5 mL, 116 mmol) was slowly added over a period of 10 minutes keeping the temperature below 5° C. The mixture was stirred at the same temperature for 2 hours to complete the reaction. The mixture was washed with HCl (1 N, 2×50 mL), water (3×50 mL), dried over magnesium sulfate, and concentrated in vacuo to afford the triflate which was used without further purification in the next step.

The above triflate was taken in a 500-mL round bottomed flask which was charged with acetone (100 mL) and then cooled to 0° C. To this solution, lithium iodide (25 g, 193 mmol) was added in portion-wise over a period of 30 minutes. The mixture was stirred at room temperature for 3 hours to complete the reaction. The mixture was directly concentrated in vacuo to remove the acetone. The resulting residue was dissolved in DCM (100 mL). The solution was washed with aqueous sodium thiosulfate solution (2×100 mL), water (2×100 mL), and dried over magnesium sulfate. The organic layer was concentrated in vacuo to give the title compound (51.5 g) as an oil.

Preparation of [1R-(1α,3α,5β)]-3-Amino-3-(dimethylphenylsilyl)-2-methylene-1-cyclopentanemethanol hydrochloride (2:1) (69)

To a round bottomed flask was mixed crude 68 (10.9 g, 20.5 mmol) zinc solid (2.68 g, 2 eq, 41 mmol) in acetic acid (20 mL). The reaction mixture was heated at 100° C. for 1 h and then cooled to room temperature. The crude mixture was mixed with tert-butyl methyl ether (30 mL) and filtered and the cake was rinsed with tert-butyl methyl ether (70 mL) at room temperature. The combined filtrate was neutralized to pH 7 with NaOH solution (1 N). The organic layer was washed with brine (30 mL), dried ($MgSO_4$) and concentrated in vacuo to afford a light yellow crude oil. This crude oil was used for the next step without further purification. The crude oil was dissolved in toluene (20 mL) and cooled to −65° C. Sodium bis(2-methoxyethoxy)aluminum hydride (Red-Al®, 65 wt. % in toluene, d=1.036, 12.3 mL) was added into the solution over ~20 min. The reaction mixture was allowed to warm up to −20° C. and stirred at −20° C. for 1 h. The reaction was quenched with NaOH (1 N, 20 mL) at 0° C. and warmed to room temperature. After stirring at room temperature for 1.5 h, the mixture was filtered through a pad of diatomaceous earth (Celite®) and the cake was rinsed with tert-butyl methyl ether (100 mL). The filtrate was dried ($MgSO_4$) and a solution of HCl in ether (1 N, 22 mL) was added at room temperature to precipitate out of the HCl salt. After stirring for 1 h at room temperature, the HCl salt was collected by filtration and dried under vacuum to afford 69 (HCl salt, 4.4 g, 72% over 3 steps) as a beige-colored solid.

Preparation of [1S-(1α,3α,4β)]-2-Amino-6-[[4-(dimethylphenylsilyl)-3-(hydroxymethyl)-2-methylenecyclopentyl]amino]-5-nitro-4(3H)-pyrimidinone (70)

A 3-necked 500 mL round bottomed flask equipped with stirrer, temperature probe and reflux condenser was charged with the amine 69 (1.49 g, 5 mmol), 2,4-diamino-5-nitropyrimidin-6-one (1.56 g, 5.35 mmol) and n-butanol (20 mL). The resultant thin slurry was subjected to heating at 40-45° C. over 15 minutes. Triethylamine (0.71 mL, 5.1 mmol) was added slowly over a period of 2 minutes. The reaction mixture was stirred at about 70° C. for 1 h. HPLC data showed that the reaction was almost complete. At this point, five washes of 25 mL of water was given to the reaction mixture at 70° C. The last wash was almost colorless. The crude product, 70, in n-butanol was used without further purification in the next reaction.

Preparation of [1S-(1α,3α,4β)]-2-Amino-9-[(4-(dimethylphenylsilyl)-3-(hydroxymethyl)-2-methylenecyclopentyl]-1,9-dihydro-6H-purin-6-one (71)

Solid $Na_2S_2O_4$ (2 g, 12 mmol) was charged into the flask containing crude 70 and the resulting slurry was heated to ~60° C., over 20 minutes. Formic acid (9.5 mL, 250 mmol) was added slowly over the course of 10 minutes at 65° C. The resulting mixture was stirred for 5 min and heated to ~70° C. for 1 hour. The mixture was cooled to 25° C. and neutralized with 6 N NaOH solution to effect a pH=7.04. The aqueous layer was separated and extracted with n-BuOH (5 mL). The combined organic layer was filtered through a pad of diatomaceous earth and transferred into 3-neck 50 mL reaction flask equipped with overhead stirrer, temperature probe and distillation head. The resultant solution was distilled under in vacuo to remove water and excess n-butanol to afford the pyrimidine intermediate The resultant slurry containing the intermediate was heated to 40-50° C. and triethylorthoformate (8 mL, 48 mmol) was added over 3 minutes, followed by conc. HCl (0.2 mL) over 1 min. The reaction mixture was heated at ~85° C. for 3 h. The reaction mixture was cooled to room temperature and stirred at room temperature for 12 h. The reaction mixture was neutralized to a pH of ~7.2 with aqueous NaOH solution. The resulting crude product over an ion exchange column to give the product 71 (1.25 g) in ~65% yield.

The compound of formula 70 could then be converted to the compound of formula 21 as described in the Example 1.

EXAMPLE 4

Process for the Preparation of [1S-(1α,3α,4β)]-2-Amino-1,9-dihydro-9-[4-hydroxy-3-(hydroxymethyl)-2-methylenecyclopentyl]-6H-purin-6-one (21)

Preparation of (4S,5R)-4-(Phenylmethoxy)-5-[(phenylmethoxy)methyl]-1-cyclopentene-1-methanol (16)

To a round bottomed flask equipped with an argon inlet, magnetic stirrer and cooling bath was dissolved (4S,5R)-4-(Phenylmethoxy)-5-[(phenylmethoxy)methyl]-1-cyclopentene-1-carboxylic acid methyl ester 7 (3.62 g, 10.2 mmol) in DCM (40 mL). The solution was cooled to −78° C. and diisobutylaluminum hydride (1 M in toluene, 22.4 mL, 22.4 mmol) was added into the solution over the course of 10 minutes. After stirring at −78° C. for 1 hour the reaction mixture was quenched with a saturated solution of potassium sodium tartrate (Rochelle salt, 50 mL) and stirred at room temperature overnight. The organic layer was diluted with ethyl acetate, separated, dried (sodium sulfate) and concentrated in vacuo to afford the crude allylic alcohol as colorless oil (3.06 g, 90%). After standing at room temperature the title compound crystallized out as a white solid.

Preparation of [1R-(1α,2α,3β,5α)]-3-(Phenyl-methoxy)-2-[(phenylmethoxy)methyl]-6-oxabicyclo [3.1.0]hexane-1-methanol (17)

To a flame dried round bottomed flask equipped with an argon inlet, magnetic stirrer and cooling bath was added (−)-(D)-diethyltartrate (188 mg, 0.91 mmol) and 4A molecular sieves (flame dried, 1.45 g) in DCM (10 mL). The reaction suspension was cooled to −25° C. and titanium (IV) isopropoxide (0.20 mL, 0.69 mmol) was added into the suspension. The reaction mixture was stirred at −25° C. for 1 hour and then tert-butyl hydroperoxide (3 M in octane, 1.52 mL, 4.5 mmol) was added. After stirring the mixture for about 1.5 hours at −25° C., 16 (0.73 g, 2.28 mmol in 4 mL DCM) was added into the solution over the course of 10 minutes. The reaction mixture was stirred at −25° C. for 3-4 hours and quenched with sodium hydroxide (5 N, 2 mL). The mixture was stirred for 1 hour at room temperature and filtered through a bed of diatomaceous earth (Celite®). The bed was rinsed with DCM (2×10 mL). The combined organic layer was washed with brine (20 mL), dried (sodium sulfate) and concentrated in vacuo to afford (0.76 g, ~100%) a colorless oil. Flash column chromatography (2:1 to 1:1 hexane/ethyl acetate) gave 0.55 g of the title compound (73%) as a light yellow solid (mp 60-62° C.).

Preparation of [1S-(1α,2β,3α,5β)]-5-[2-Amino-6-(phenylmethoxy)-9H-purin-9-yl]-1-hydroxy-3-(phenylmethoxy)-2-(phenylmethoxy)methyl]cyclopentanemethanol (18, X=BnO)

To a round bottomed flask equipped with an argon inlet, a magnetic stirrer and a reflux condensor were charged 2-amino-6-O-benzyloxypurine (1.66 g, 6.87 mmol) with dimethylformamide (20 mL). Lithium hydride (32.7 mg, 4.13 mmol)) was added into the suspension, and the resulting mixture was stirred for 1 hour. A solution of 17 (2.13 g in 2 mL dimethylformamide, 6.25 mmol) was added into the solution. The solution was heated to 120-130° C. for 1 hour. The resulting solution was worked up by quenching with sodium hydroxide (1 N, 20 mL), and extracting with ethyl acetate (2×150 mL). The combined organic layer was washed with saturated ammonium chloride solution (200 mL) and brine (100 mL), dried (sodium sulfate), and concentrated in vacuo to afford a light brown solid. This solid was dissolved in ethyl acetate/DCM and passed through a pad of flash silica gel (eluted with ethyl acetate) to afford 3.1 g of the title compound (85%) as light yellow solid. Recrystallization (ethyl acetate/hexanes) gave 2.81 g of the title compound in ~78% yield as an off white solid.

Preparation of [1S-(1α,3α,4β)]-2-Amino-1,9-dihydro-9-[2-methylene-4-(phenylmethoxy)-3-[(phenylmethoxy)methyl]cyclopentyl]-6H-purin-6-one (20)

A 1-L round bottomed flask equipped with an argon inlet, and a magnetic stirrer was charged with 18 (2.6 g, 4.4 mmol), trimethyl orthoformate (2.38 mL, 21.8 mmol), pyridinium p-toluenesulfonate (0.56 g, 2.22 mmol), and DCM (20 mL). The reaction mixture was stirred for about 16 hours at room temperature. After the completion of the reaction, the reaction mixture was quenched with sodium bicarbonate solution (50 mL). The resulting mixture was extracted with ethyl acetate (2×50 mL) and the combined organic layer was washed with brine (50 mL), dried (sodium sulfate), and concentrated in vacuo to afford the orthoformate intermediate. The crude product was dissolved with acetic acid/acetic anhydride (1.5 mL/30 mL) in a round bottomed flask. The solution was heated to reflux for about 5 hours and then cooled to room temperature. The acetic acid/acetic anhydride was removed by vacuum distillation to afford an intermediate mixture (2.34 g). The above intermediate mixture (2.2 g, 3.7 mmol) was dissolved in acetonitrile (60 mL) and 2 N HCl (30 mL), and then heated to reflux to complete the reaction. The mixture was cooled to room temperature and neutralized by addition of triethylamine. The mixture was directly concentrated in vacuo to remove most of acetonitrile. Ethanol was added to the resulting solid residue and the suspension was stirred for 1 hour. The solid was collected by filtration, rinsed with ethanol, and dried under high vacuum to afford 1.57 g of the title compound in 93% yield.

Preparation of [1S-(1α,3α,4β)]-2-Amino-1,9-dihydro-9-[4-hydroxy-3-(hydroxymethyl)-2-methylenecyclopentyl]-6H-purin-6-one (21)

To a round bottomed flask equipped with magnetic stirrer and nitrogen inlet-outlet were mixed 20 (2.7 g, 5.9 mmol) with $CH_2Cl_2$ (10 mL). The mixture was cooled to −78° C. and $BCl_3$ (1 M, 35.4 mL, 35.4 mmol) was added into the reaction suspension at a rate so that the reaction temperature did not exceed −65° C. The reaction mixture was stirred at −78° C. for 0.5 h and then it was warmed up to −20° C. After stirring at −20° C. for 1 h, the reaction mixture was re-cooled to −78° C. and MeOH (30 mL) was added into the reaction mixture and warmed to room temperature. The reaction mixture was concentrated in vacuo to remove MeOH to afford a light yellow oil. This oil was re dissolved in MeOH (30 mL); Decolorizing carbon (2.7 g) was added into the solution and stirred at room temperature for 0.5 h. The suspension was filtered through diatomaceous earth and the cake was rinsed with MeOH (10 mL). The combined filtrate was concentrated in vacuo to afford a clear oil. This oil was dissolved in water (20 mL) and extracted with ethyl acetate (2×30 mL). The aqueous layer was neutralized by addition of NaOH to effect a pH ~7.2. The solid from the suspension was collected by filtration and recrystallized with water (30 mL) to afford 1.36 g of 21.

EXAMPLE 5

Process for the Preparation of [1S-(1α,3α,4β)]-2-Amino-1,9-dihydro-9-[4-hydroxy-3-(hydroxymethyl)-2-methylenecyclopentyl]-6H-purin-6-one (21)

Preparation of Compound (1α,2β,3α)-2-[(Phenylmethoxy)methyl]-4-cyclopentene-1,3-diol diacetate ester (2)

To a round bottomed flask equipped with magnetic stirrer was dissolved 1 (2.2 g, 10 mmol) in acetic anhydride (4 mL) and pyridine (2.5 mL). After stirring at room temperature overnight, the excess acetic anhydride and pyridine was removed by vacuum distillation, the crude oil was chromatographed (silica, 2:1 Hexane/EtOAc) to afford 2.8 g (92%) of 2 as light yellow oil.

Preparation of (+)-(1α,2β,3α)-2-[(Phenylmethoxy)methyl]-4-cyclopentene-1,3-diol monoacetate ester (3) (without immobilization of the enzyme)

Enantioselctive asymmetric hydrolysis of the diacetate 2 was carried out using the enzyme Pancreatin or Lipase PS-30 from *Pseudomonas cepacia*. The reaction mixture contained 25 mM potassium phosphate buffer (36 mL, pH 7.0), toluene (4 mL) and the diacetate 2 (2 mg/mL) and Lipase PS-30 or Pancreatin (50 mg/mL). The reaction was carried out at 25° C., maintaining the pH at 7.0 by addition of 1 N NaOH as required. The progress of the reaction was monitored by high pressure liquid chromatography. The reaction was terminated when the concentration of the remaining substrate 2 dropped below 0.05 mg/mL. The reaction mixture was concentrated under reduced pressure to obtain (+)-monoacetate 3. After 16 h of reaction time, a reaction yield of 80 M% and an ee of 98% was obtained using Lipase PS-30. A reaction yield of 75% and an ee of 98.5% was obtained using Pancreatin.

Preparation of (+)-(1α,2β,3α)-2-[(Phenylmethoxy) methyl]-4-cyclopentene-1,3-diol monoacetate ester (3) (using immobilized Lipase PS-30)

Enantioselective asymmetric hydrolysis of diacetate 2 was carried out using immobilized Lipase PS-30. Crude Lipase PS-30 from *Pseudomonas cepacia* was immobilized on polypropylene (Accurel Systems International Corp.) and immobilized enzyme was used. The reaction contained 25 mM potassium phosphate buffer (1.8 L, pH 7.0), toluene (200 mL), diacetate 2 (52 g), and immobilized Lipase PS-30 (180 g). After 18 h reaction time, a reaction of 80 M% (32.5 g) and ee of 98% were obtained for the (+)-monoacetate 3. At the end of the reaction, the immobilized enzyme was filtered and the clear supernatant obtained was extracted with two volumes of ethyl acetate. The separated organic phase was concentrated under reduced pressure to obtain the desired product 3.

Preparation of [1S-(1α,4α,5β)]1-4-[Nitro(phenylsulfonyl)methyl]-5-[(phenylmethoxy)methyl]-2-cyclopenten-1-ol (4)

To a round bottomed flask equipped with an argon inlet, magnetic stirrer, addition funnel and reflux condensor was added compound 3 (0.98 g, 3.74 mmol), phenylsulfonylnitromethane (0.91 g, 4.5 mmol) and tetrakis[triphenylphosphine]-palladium (43 mg, 0.037 mmol) in THF (7 mL) at 0° C. The reaction mixture was degassed using argon for a few minutes. Triethylamine (1.1 g, 1.6 mL, 11.4 mmol) was added into the reaction mixture over the course of 2 minutes at 0° C. The reaction mixture was stirred at 0° C. for 1 hour and allowed to warm up to room temperature. The reaction mixture was then stirred at room temperature for 3 hours. The reaction mixture was quenched with 1 N HCl at 0° C. (15 mL) and extracted with hexane/ethyl acetate (1:1; 2×20 mL). The combined organic layer was washed with brine (30 mL), dried (sodium sulfate) and concentrated in vacuo to afford a red-colored oily residue (2.2 g). Silica pad filtration was performed to remove the baseline materials to give the title compound (1.36 g).

Preparation of [1R-(1α,4α,5β)]-[[Nitro[4-(phenyl-methoxy)-5-[(phenylmethoxy)methyl-2-cyclopenten-1-yl]methyl]sulfonyl]benzene (5)

To a round bottomed flask with an argon inlet, a magnetic stirrer and a cooling bath was charged 4 (3.0 g, 7.43 mmol) in THF at 0° C. Sodium hydride (60% suspension in mineral oil, 0.68 g, 17 mmol) was added into the reaction mixture portionwise over the course of 10 minutes with stirring. The resulting suspension was stirred at 0° for 30 minutes, warmed to room temperature, and stirred for 1 hour at room temperature. Benzyl bromide (1.52 g, 1.06 mL, 8.91 mmol) was added and the reaction mixture was heated at 45° C. for 3 hours to complete the reaction. The reaction was quenched with cold HCl (1 N, 30 mL) and extracted with ethyl acetate (2×30 mL). The combined organic layer was washed with brine (30 mL), dried (sodium sulfate), and concentrated in vacuo to afford the title compound as a light brown oil (3.98 g). The crude product was used without further purification in the next step.

Preparation of (4S,5R)-4-(Phenylmethoxy)-5-[(phenylmethoxy)methyl]-1-cyclopentene-1-carboxylic acid methyl ester (7)

To a round bottomed flask equipped with an argon inlet, a magnetic stirrer, an addition funnel and a reflux condensor was added 5 (2.7 g, 5.47 mmol) and sodium carbonate (2.58 g, 46 mmol) in a mixture of DCM/MeOH (3:1, 10 mL) at room temperature. The reaction mixture was heated to reflux and a solution of potassium peroxymonosulfate:tetrabutyl ammonium salt (2.3% active oxygen, 11 g in 15 mL of DCM, 7.9 mmol) in DCM was added into the reaction suspension dropwise over a period of 10 hours. After refluxing for about 14 hours, the reaction mixture was cooled to room temperature and diluted with MeOH (50 mL). The resulting mixture was cooled to −40° C. Concentrated sulfuric acid was added to neutralize the reaction medium to acidic pH (1.2 mL was used). The reaction mixture was warmed up to room temperature and stirred at room temperature for 3 hours. The reaction mixture was quenched with water/brine (1:1; 40 mL) and extracted with hexane/ethyl acetate (2:1, 2×200 mL). The combined organic layer was washed with saturated sodium bicarbonate solution (100 mL) and brine (100 mL), dried (sodium sulfate) and concentrated in vacuo to afford crude intermediate (1.88 g, >100% material balance) which was used in the next step without any further purification.

To a round bottomed flask equipped with an argon inlet and a magnetic stirrer was dissolved the above obtained intermediate (2.95 g, 8.1 mmol) in dry MeOH (10 mL). A sodium methoxide solution in MeOH solution (25 wt. %, 0.34 g, 1.6 mmol) was added at room temperature. The reaction mixture was stirred at room temperature for 2 hours. After completion, the reaction mixture was neutralized with HCl (10 mL) at 0° C., and extracted with ethyl acetate/hexane (1:1; 2×100 mL). The combined organic layer was washed with brine, dried (sodium sulfate), and concentrated in vacuo to afford a solid. Recrystallization with hexane/tert-butyl methyl ether (10:1) at −20 to −30° C. gave 1.83 g of the title compound in 64% yield as a light yellow solid.

EXAMPLE 6

Process for the Preparation of [1S-(1α,3α, 4β)]-2-Amino-1,9-dihydro-9-[4-hydroxy-3-(hydroxymethyl)-2-methylenecyclopentyl]-6H-purin-6-one (21)

Preparation of (−)-(1α,2β,3α)-2-[(Phenylmethoxy) methyl]-4-cyclopentene-1,3-diol monoacetate ester (13) (without immobilization of the enzyme)

Enantioselective acetylation of the diol 1 was carried out using immobilized Lipase PS-30 from *Pseudomonas cepacia*. The reaction mixture contained heptane/t-butyl methyl ether (10/1 v/v, 1 L), diol 1 (5 g), immobilized Lipase PS-30 (25 g), and isopropenyl acetate (2 eq) as the acylating agent. The reaction was carried out at 33° C. The progress of the reaction was monitored by high pressure liquid chromatography. The reaction was terminated when the concentration of the remaining substrate 1 dropped below 0.1 mg/mL. After 4 h, a reaction yield of 80% and an ee of 98% was obtained for the (−)-monoacetate 13.

Preparation of [1R-(1α,4α,5β)]-Carbonic acid, methyl 4-(acetoxy)-5-[(phenylmethoxy)methyl]-2-cyclopenten-1-yl ester (10)

To a round bottomed flask equipped with magnetic stirrer and N$_2$ inlet-outlet were mixed 13 (2.62 g, 10 mmol), pyridine (1.18 g, 12 mmol) with CH$_2$Cl$_2$ (5 mL). The mixture was cooled to −5° C. and methyl chloroformate (1.134 g, 12 mmol) was added into the reaction suspension at a rate so that the reaction temperature did not exceed 0° C. The reaction mixture was stirred at 0° C. for 1 h and warmed up to room temperature for 1 h. The resulting mixture was quenched with saturated ammonium chloride solution at 0° C. The quenched solution was extracted with 1:2 EtOAc/hexane (30 mL×2). The combined organic layer was washed with brine (30 mL); dried (Na$_2$SO$_4$); concentrated in vacuo, and dried under high vacuum to afford crude 14 (3.32 g, 100%) as light brown oil. It was used in the next reaction without further purification.

Preparation of [1R-(1α,4α,5β)]-[[Nitro[4-(acetoxy)-5-[(phenylmethoxy)methyl]-2-cyclopenten-1-yl]methyl]sulfonyl]benzene (15)

To a round-bottomed flask equipped with magnetic stirrer was dissolved phenylsufonylnitromethane (2.41 g, 12 mmol) in dry THF (25 mL). At 0° C., sodium hydride (0.46 g, 60% mineral oil dispersion, 12 mmol) was added over 5 min. After warming up to room temperature and stirred at room temperature for 1 h, crude 14 (3.3 g, 10 mmol in 5 mL of THF) was added over 10 min. The reaction was stirred at room temperature for 30 min and at 50° C. for 1 h. The reaction mixture was worked up by the addition of saturated ammonium chloride solution (30 mL) followed by extraction with ethyl acetate (2×40 mL). The combined organic phase was washed with brine (30 mL); dried (Na$_2$SO$_4$) and concentrated in vacuo to afford 15 as a crude brown oil (5.12 g, >100%) which was used in the next step without purification.

Preparation of [1R-(1α,4α,5β)]-[[Nitro[4-(hydroxy)-5-[(phenylmethoxy)methyl]-2-cyclopenten-1-yl]methyl]sulfonyl]benzene (4)

To a round bottomed flask equipped with magnetic stirrer was dissolved crude 15 (5.12 g, 10 mmol) in 25 mL MeOH. Potassium carbonate (140 mg, 1 mmol) was added into the flask at room temperature and the resulting mixture was stirred overnight. The reaction mixture was concentrated in vacuo to remove MeOH. The concentrate was extracted with ethyl acetate (2×30 mL) and saturated ammonium chloride solution (30 mL). The combined organic layer was washed with brine (20 mL); dried (Na$_2$SO$_4$) and concentrated in vacuo to afford a light brown oil. Flash column chromatography (1:2 to 1:1 EtOAc/hexane) afford 2.92 g of 4 (73%) as a colorless oil.

EXAMPLE 7

Process for the Preparation of [1S-(1α,3α,4β)]-2-Amino-1,9-dihydro-9-[4-hydroxy-3-(hydroxymethyl)-2-methylenecyclopentyl]-6H-purin-6-one (21)

Preparation of [1R-(1α,4α,5β)]-4-(Phenylmethoxy)-5-[(phenylmethoxy)methyl]-2-cyclopenten-1-ol (9) (R'=Bn)

To a round bottomed flask equipped with an argon inlet, a magnetic stirrer, a cooling condenser, and an oil bath was charged [1S-(1α,2α,3β,5β)]1-3-(Phenylmethoxy)-2-[(phenylmethoxy)methyl]-6-oxabicyclo[3.1.0]hexane 8 (20.19 g, 65 mmol, as prepared in U.S. Pat. No. 5,206,244, herein incorporated by reference) in THF (150 mL). Lithium hexamethyldisilazide (1 M in hexane, 190 mL, 190 mmol) was added into the solution at room temperature. The reaction mixture was heated at 60° C. for 1.5 hours. The resulting solution was cooled to room temperature and diluted with MeOH (200 mL). After stirring for 20 minutes at room temperature, the reaction mixture was quenched with HCl (1 N, 300 mL), and extracted with ethyl acetate (3×300 mL). The combined organic layer was washed with brine (2×200 mL), dried (sodium sulfate), and concentrated in vacuo to afford 22.7 g of the title compound (>100% material balance) which was used in the next step without any further purification.

Preparation of [1R-(1α,4α,5β)]-Carbonic acid, methyl 4-(phenylmethoxy)-5-[(phenylmethoxy)methyl]-2-cyclopenten-1-yl ester (10)

To a round bottomed flask equipped with an argon inlet, a magnetic stirrer and a cooling bath was charged crude 9 (12.3 g, 39.6 mmol) and pyridine (9.7 mL, 120 mmol) in DCM (100 mL). The solution was cooled to −20 to −15° C. and methyl chloroformate (4.2 g, 3.41 mL, 44 mmol) was added into the solution over the course of 20 minutes. The reaction mixture was stirred at −15° C. for 0.5 hour and then slowly warmed to room temperature to complete the reaction. The resulting mixture was quenched with HCl (2 N, 120 mL) at 0° C. and extracted with ethyl acetate (2×300 mL). The combined organic layer was washed with brine (200 mL), dried (sodium sulfate), concentrated in vacuo, and dried under high vacuum to afford the crude title compound as a brown oil which was used in the next step without any further purification.

Preparation of [1R-(1α,4α,5β)]-[[Nitro[4-(phenylmethoxy)-5-[(phenylmethoxy)methyl]-2-cyclopenten-1-yl]methyl]sulfonyl]benzene (5)

To a round bottomed flask equipped with an argon inlet, a magnetic stirrer and a cooling bath was dissolved crude 10 (9.8 g, 26.5 mmol), phenylsulfonylnitromethane (5.4 g, 26.8 mmol) and tetrakis(triphenylphosphine)palladium (0.6 g, 0.52 mmol) in THF (80 mL) at 0° C. The reaction mixture was degassed using argon for a few minutes. Triethylamine (8.4 g, 11.1 mL, 79.5 mmol) was added to the reaction mixture over the course of 10 minutes at 0° C. The reaction mixture was stirred at 0° C. for 1 hour and allowed to warm to room temperature. The reaction mixture was stirred at room temperature for 3 hours. The reaction mixture was then quenched with 2 N HCl at 0° C. (100 mL) and extracted with hexane/ethyl acetate (1:1; 2×30 mL). The combined organic layer was washed with brine (100 mL), dried (sodium sulfate), and concentrated in vacuo to afford a red-colored oily residue. Silica pad filtration was conducted using ethyl acetate to remove the baseline materials and give the title compound (14.2 g crude, >100%) as a light brown oil which was used in the next step without any further purification.

The conversion of compound of formula 5 to the ester of formula 7 is described in Example 5.

EXAMPLE 8

Process for the Preparation of [1S-(1α,3α,4β)]-2-Amino-1,9-dihydro-9-[4-hydroxy-3-(hydroxymethyl)-2-methylenecyclopentyl]-6H-purin-6-one (21)

Preparation of (4S,5R)-4-(Phenylmethoxy)-5-[(phenylmethoxy)methyl]-2-cyclopenten-1-one (80)

To a round bottomed flask equipped with an argon inlet, magnetic stirrer were mixed with molecular sieves (4 g); pyridinium dichromate (4.16 g, 20 mmol) and HOAc (0.60 g, 10 mmol) with $CH_2Cl_2$ (25 mL) at 0° C. and stirred for 1 h. Allylic alcohol 9 (3.11 g, 10 mmol, prepared according to Example 7) in $CH_2Cl_2$ (5 mL) was added into the flask over ~5 min. After stirring for 2.5 h at 0° C., the reaction mixture was filtered through a pad of silica gel and the cake was rinsed with 1:3 $CH_2Cl_2$/EtOAc. The resulting filtrate was extracted with HCl (1 N, 40 mL)/EtOAc (50 mL). The organic layer was dried ($Na_2SO_4$) and concentrated in vacuo to afford a brown oil. This brown oil was chromatographed with 1:2 EtOAc/Hexane to afford 80 (2.85 g, 92%) of light yellow oil Preparation of (4S,5R)-Trifluoromethanesulfonic acid 4-(phenylmethoxy)-5-[(phenylmethoxy)methyl]-1-cyclopenten-1-yl ester (81)

To a round bottomed flask equipped with an argon inlet, magnetic stirrer were mixed with 80 (1.7 g, 5.5 mmol) with THF (15 mL) and cooled to −78° C. Lithium tri-sec-butylborohydride (L-Selectride®) (1 M in THF, 5.5 mL, 5.5 mmol) was added over ~20 min. at −78° C. The reaction mixture was stirred at −78° C. for 1.5 h and N-phenyltrifluoromethanesulfonimide (1.98 g, 5.5 mmol) was added at −78° C. After stirring at −78° C. for 1 h, the reaction mixture was allowed to slowly warm up to room temperature and stirred at room temperature overnight. The resulting mixture was worked up with saturated $NH_4Cl$ solution (30 mL) and extracted with EtOAc (52 mL). The emulsion was filtered through a pad of diatomaceous earth and washed with EtOAc (20 mL) the combined organic layer was dried ($Na_2SO_4$) and concentrated in vacuo to afford a brown oil (3.2 g, 100%). This brown oil was used in the next reaction without further purification.

Preparation of (4S,5R)-4-(Phenylmethoxy)-5-[(phenylmethoxy)methyl]-1-cyclopentene-1-carboxylic acid methyl ester (7)

To a round bottomed flask equipped with an argon inlet, magnetic stirrer were mixed crude 81 (3.2 g, 5.5 mmol) DMF (25 mL); MeOH (10 mL) and triethylamine (1.54 mL, 11 mmol). $Pd(Ph_3)_4$ (635 mg, 0.55 mmol) was added into the solution and the resulting mixture degassed 3 times with CO gas. The reaction was stirred at 1 atmosphere of CO gas at room temperature for 2 h. TLC showed no the absence of starting material. The reaction was worked up with NaOH (0.5 N, 100 mL) at room temperature and extracted with EtOAc (2×50 mL). The combined EtOAc layer was washed with brine (50 mL); dried ($Na_2SO_4$) and concentrated in vacuo to afford a light yellow oil. Flash column chromatography (1:2 hexane/EtOAc) gave 7 (1.36 g, 70% over 4 steps).

EXAMPLE 9

Process for the Preparation of [1S-(1α,3α,4β)]-2-Amino-1,9-dihydro-9-[4-hydroxy-3-(hydroxymethyl)-2-methylenecyclopentyl]-6H-purin-6-one (21)

Preparation of [1R-(1α,4α,5β)]-4-[[(1,1-Dimethylethyl)dimethylsilyl]oxy]-5-[(phenylmethoxy)methyl]-2-cyclopenten-1-ol acetate ester (22)

To a round bottomed flask equipped with a nitrogen inlet was dissolved compound 3 (1.85 g, 7.05 mmol) in $CH_2Cl_2$ (10 mL), and the resulting solution was cooled to 0° C. To the reaction mixture was added triethylamine (1.43 g, 2 mL, 14.1 mmol), 4-N,N-dimethylaminopyridine (DMAP, ~100 mg) and tert-butyldimethyl chlorosilane (1.17 g, 7.75 mmol) at 0° C. The resulting mixture was warmed to room temperature and stirred overnight. The resulting mixture was worked up by addition of NaOH solution (0.5 N, 20 mL) at 10° C. and extracted with a solution of ethyl acetate/hexanes (1:2 v/v, 2×30 mL). The combined organic layer was washed with brine (30 mL), dried ($Na_2SO_4$), and concentrated in vacuo to compound 22 as a crude light oil.

Preparation of [1R-(1α,4α,5β)]-4-[[(1,1-Dimethylethyl)dimethylsilyl]oxy]-5-[(phenylmethoxy)methyl]-2-cyclopenten-1-ol (9)

The above obtained compound 22 was dissolved in MeOH (30 mL), and potassium carbonate (150 mg) was added at room temperature. After stirring at room temperature for 5 h, the MeOH was removed by concentrating the reaction mixture in vacuo. The resulting mixture was extracted with ethyl acetate/hexanes (1:2 v/v, 2×30 mL) and saturated $NH_4Cl$ solution (20 mL). The combined organic layer was washed with brine (30 mL), dried ($Na_2SO_4$), and concentrated in vacuo to afford a light yellow oil. The oil was further purified by flash column chromatography (hexanes/ethyl acetate 8:1 to 3:1) to afford compound 9 (2.28 g, 97% overall from compound 3).

Preparation of (4S,5R)-4-[[(1,1-Dimethylethyl)dimethylsilyl]oxy]-5-[(phenylmethoxy)methyl]-2-cyclopenten-1-one (80)

To a 250-mL 3-necked flask, oven dried and equipped with a mechanical stirrer was charged with pyridinium dichromate (20.24 g, 53.80 mmol), molecular sieves (oven dried) and DCM (40 mL). The resulting slurry was cooled to 0° C. and to this slurry, acetic acid (which had been dried over molecular sieves, 1.61 g, 26.90 mmol) was charged. The resulting mixture was stirred for 30 minutes at 0° C. 9 (10 g, 29.89 mmol) in DCM (10 mL) was added to the reaction mixture over a period of 10 minutes. The resulting reddish colored reaction mixture was stirred for 2 hours at 0° C. After the reaction was completed, ethyl acetate (100 mL), acetonitrile (5 mL), and diatomaceous earth (Celite®, 5 g) were added sequentially, and the resulting mixture was stirred for 10 minutes. The slurry was filtered on a bed of diatomaceous earth (Celite®) to give a dark colored filtrate. The filtrate was washed with 5% aqueous $NaHSO_3$ (2×250 mL) followed by water (100 mL). The organic layer was dried over magnesium sulfate and the solvent was concentrated in vacuo to give 9.5 g of the title compound as a dark transparent, brown oil.

Preparation of (4S,5R)-Trifluoromethanesulfonic acid 4-[[(1,1-dimethylethyl)dimethylsilyl]oxy]-5-[(phenylmethoxy)methyl]-1-cyclopenten-1-yl ester (81)

An oven dried 250-mL 3-necked round bottomed flask, equipped with a mechanical stirrer and an argon inlet, was charged with 80 (9.5 g, 29.89 mmol) and THF (10 mL). The resulting mixture was cooled to −78° C. Lithium tri-sec-butylborohydride (L-Selectride®) (1 M, 6.25 g, 32.88 mmol) in THF (20 mL) was added over a 20 minute period. To this reaction mixture, N-phenyltriflimide (10.46 g, 29.29 mmol) in THF (20 mL) was added over a period of 5 minutes, keeping the reaction temperature below −78° C. The reaction mixture was stirred overnight while allowing it to warm to room temperature. Tert-butyl methyl ether (100 mL) was added to the reaction mixture and the resulting organic layer was washed with saturated aqueous sodium bicarbonate solution (2×75 mL) followed by brine (5 mL). The organic layer was dried over magnesium sulfate and concentrated in vacuo to give the title compound (27 g) as yellow oil.

Preparation of (4S,5R)-4-[[(1,1-Dimethylethyl)dimethylsilyl]oxy]-5-[(phenylmethoxy)methyl]-1-cyclopentene-1-carboxylic acid methyl ester (7)

A 250-mL 3-necked round bottomed flask equipped with a mechanical stirrer was charged with 81 (27.0 g, 29.89 mmol), dimethylformamide (20 mL), MeOH (20 mL) and triethylamine (20.74 mL, 149.45 mmol). The reaction mixture was flushed three times with argon. To this mixture was added tetrakis(triphenylphosphine) (1.762 g, 1.49 mmol). The reaction mixture was flushed three times with carbon monoxide. The reaction mixture was stirred at room temperature for 18 hours under an atmosphere of carbon monoxide. The reaction mixture was extracted with tert-butyl methyl ether (200 mL) and the reddish mixture was filtered on a bed of diatomaceous earth (Celite®). The filtrate was concentrated in vacuo to give 30 g of a blackish colored oil which upon column chromatography purification gave the title compound as an oil (4.5 g, 40% yield overall yield from 23).

EXAMPLE 10

Process for the Preparation of [1S-(1α,3α,4β)]-2-Amino-1,9-dihydro-2-[4-hydroxy-3-(hydroxymethyl)-2-methylenecyclopentyl]-6H-purin-6-one (21)

Preparation of Compound (4S,5R)-4-[[(1,1-Dimethylethyl)dimethylsilyl]oxy]-5-[(phenylmethoxy)methyl]-1-cyclopentene-1-methanol (16)

A 500-mL 3-necked round bottomed flask, equipped with an argon inlet, a temperature probe, and a mechanical stirrer, was charged with (4S,R)-4-[[(1,1-Dimethylethyl)dimethylsilyl]oxy]-5-[(phenylmethoxy)methyl]-1-cyclopentene-1-carboxylic acid methyl ester (7) (10 g, 26.55 mmol, as prepared in Example 9) in DCM (200 mL). The solution was cooled to −78° C. and to this solution diisobutylaluminum hydride (1 M, 66.39 mL, 66.375 mmol in toluene) was added slowly. The reaction mixture was stirred at −78° C. for 2 hours to complete the reaction. The reaction mixture was poured into saturated solution of potassium sodium tartrate (400 mL). The mixture was stirred for 2 hours. The organic layer was separated and the aqueous layer was extracted with n-hexane (200 mL). The combined organic layer was washed with water (50 mL), dried over magnesium sulfate, and concentrated in vacuo to give the title compound (9.3 g) as a yellowish oil.

Preparation of [1R-(1α,2α,3β,5α)]-3-[[(1,1-Dimethylethyl)dimethylsilyl]oxy]-2-[(phenylmethoxy)methyl]-6-oxabicyclo[3.1.0]hexane-1-methanol (17)

A 250-mL oven dried three necked round bottomed flask was equipped with a magnetic stir bar, argon inlet, and temperature probe charged with oven dried powdered molecular sieves 4A° (9.0 g). DCM (30 mL) was added to the flask and the resulting suspension was stirred room temperature for 5 minutes. Diethyl D-tartrate (2.13 g, 10.32 mmol) in DCM (18 mL) was added at room temperature and the mixture was cooled to −30° C. Keeping the temperature at ∼−30° C., titanium (IV) isopropoxide (2.665 mL, 9.03 mmol) was added. The reaction mixture was stirred at −30° C. for 30 minutes followed by 15 minutes at −15° C. The mixture was cooled to −30° C. To this mixture, a solution of compound 16 (4.5 g, 12.9 mmol) in DCM (18 mL) was added. The mixture was stirred for 30 minutes at −30° C. followed by addition of a solution of tert-butyl hydroperoxide (5.0-6.0 M; 9.40 mL, 5.176 mmol). The reaction mixture was stirred between −30° C. to −20° C. for 3 hours to complete the reaction. The reaction was quenched by addition of water (45 mL). The reaction mixture was stirred with vigorous mixing and allowed to warm up to room temperature (15 to 20° C.). When the temperature reached ∼15° C., 30% sodium hydroxide solution (10 mL) was added slowly to give a milky white slurry. This slurry was added into a 3.0-L Erlenmeyer flask containing tert-butyl methyl ether (1100 mL). The mixture was stirred for 30 minutes and then filtered on a bed of diatomaceous earth (Celite®). The aqueous layer was separated from the filtrate and discarded. The organic layer was washed with 10% aqueous sodium thiosulfate (100 mL) and water (2×160 mL). The combined organic layer was washed with water (100 mL), brine (50 mL), and dried over magnesium sulfate. The organic layer was concentrated in vacuo to give the title compound in quantitative yield (5.47 g) as an oil.

Preparation of Compound [1S-(1α,2α,4β,5α)]-5-[2-Amino-6-(phenylmethoxy)-9H-purin-9-yl]-3-[[(1,1-dimethylethyl)dimethylsilyl]oxy]-1-hydroxy-2-[(phenylmethoxy)methyl]cyclopentanemethanol (18)

To a round bottomed flask equipped with an argon inlet, magnetic stirrer and refluxing condenser were charged O-benzyloxy guanine (1.66 g, 6.87 mmol) with DMF (20 mL). LiH (32.7 mg, 4.13 mmol)) was added into the suspension and stirred for 1 h. A solution of 17 (2.13 g in 2 mL DMF, 6.25 mmol) was added into the solution and heated to 120-130° C. for 1 h. The resulting solution was worked up by quenching with NaOH (1 N, 20 mL) and extracted with EtOAc (2×150 mL). The combined organic layer was washed with saturated NH$_4$Cl (200 mL), brine (100 mL), dried (Na$_2$SO$_4$) and concentrated in vacuum to afford a light brown solid. This solid was dissolved in EtOAc/CH$_2$Cl$_2$ and passed through a pad of flash silica gel (eluted with EtOAc) to afford 3.102 g of 18 (85%) as light yellow solid. Recrystallization (EtOAc/Hex.) gave 2.6 g (1st crop, 72%) and 0.21 g (2nd crop, 5.8%) of 18 as an off white solid.

Preparation of [1S-(1α,2α,4β)]-4-[2-Amino-6-(phenylmethoxy)-9H-purin-9-yl]-3-methylene-2-[(phenylmethoxy)methyl]cyclopentanol (19)

A round bottomed flask equipped with an argon inlet, magnetic stirrer was charged 18 (2.6 g, 4.4 mmol), trimethylorthoformate (2.38 mL, 21.8 mmol), pyridinium p-toluenesulfonate (0.56 g, 2.22 mmol) and CH$_2$Cl$_2$ (20 mL). The reaction mixture was stirred for about 16 h at room temperature. After the completion of the reaction, the reaction mixture was quenched with NaHCO$_3$ (50 mL). The resulting mixture was extracted with EtOAc (2×50 mL) and the combined organic layer was washed with brine (50 mL), dried (Na$_2$SO$_4$) and concentrated in vacuo to afford the orthoformate. The crude product was dissolved with HOAc/Ac$_2$O (1.5 mL/30 mL) in a round bottomed flask and heated to reflux for about 5 h. The mixture was then cooled to room temperature. The HOAc/Ac$_2$O was removed by vacuum distillation to afford a light brown oil. The crude product was purified by a silica pad filtration to afford 2.34 g of a mixture.

Preparation of [1S-(1α,3α,4β)]-2-Amino-1,9-dihydro-9-[4-hydroxy-2-methylene-3-[(phenylmethoxy)methyl]cyclopentyl]-6H-purin-6-one (20)

The above mixture (2.2 g, 3.7 mmol) was dissolved in CH$_3$CN (60 mL) and 2 N HCl (30 mL) and the resulting solution was heated to reflux. The reaction mixture was monitored by HPLC. After the completion of the reaction, the mixture was cooled to room temperature and neutralized by addition of triethylamine. The mixture was directly concentrated in vacuo to remove most of CH$_3$CN. Ethanol was added to the resulting solid residue, and the suspension was stirred for 1 h. The resulting solid was collected by filtration. The solid was rinsed with EtOH and dried under high vacuum to afford 1.57 g of 20.

The compound of formula 20 was then converted to the compound of formula 21 according to the procedure described in Example 4.

EXAMPLE 11

Process for the Preparation of [1S-(1α,3α,4β)]-2-Amino-1,9-dihydro-9-[4-hydroxy-3-(hydroxymethyl)-2-methylenecyclopentyl]-6H-purin-6-one (21)

Preparation of (4S)-4-[[(1,1-Dimethylethyl)dimethylsilyl]oxy]-2-cyclopenten-1-one (33)

To a 1-L round bottomed flask was charged (4S)-4-Hydroxy-2-cyclopenten-1-one (32) (20 g, 204 mmol, prepared described in Khanapure, S.; Najafi, N.; Manna, S.; Yang, J.; Rokash. J. *J. Org. Chem.*, 1995, 60, 7448) in DCM (200 mL) followed by N,N-dimethylethylamine (47.7 g, 653 mmol), tert-butyldimethylsilyl chloride (46.1 g, 306 mmol) and a catalytic amount of 4-N,N-dimethylaminopyridine (1 g). The mixture was stirred at room temperature for 24 hours. The reaction mixture was poured into ethyl acetate (200 mL) and the organic layer washed with water (200 mL), aqueous HCl (1 N, 2×100 mL), brine (100 mL) and saturated sodium bicarbonate solution (100 mL). The organic layer was dried over magnesium sulfate and concentrated in vacuo to afford the title compound as a crude product (42 g, ~98% yield).

Preparation of (3S,4S)-4-[[(1,1-Dimethylethyl)dimethylsilyl]oxy]-3-[(dimethylphenylsilyl)methyl]-1-[(trimethylsilyl)oxy]cyclopentane (34)

To a suspension of magnesium (1.18 g, 48.5 mmol) in THF (15 mL) at room temperature in 100 mL round bottomed flask was added (chloromethyl)-dimethylphenylsilane (8.86 g, 48.5 mmol). The resulting mixture was stirred for ~1 hour to form the Grignard reagent. To this solution, copper (I) bromide-dimethylsulfide complex (2.13 g, 10.4 mmol) was added, and the mixture was stirred at room temperature for 30 minutes. The resulting solution was cooled to −78° C., and to it was added slowly chlorotrimethylsilane (1.2 g, 11.3 mmol), followed by a solution of 33 (2 g, 9.4 mmol) in THF (2 mL). The reaction mixture was stirred at −78° C. for 1 hour and at 0° C. for 3 hours to complete the reaction. The reaction mixture was poured into a flask containing hexanes (200 mL) and stirred for 10 minutes. The mixture was filtered through a bed of diatomaceous earth (Celite®) and the resulting filtrate was concentrated in vacuo to dryness to afford the crude title compound.

Preparation of [3S-(3α,4β)]-4-[[(1,1-Dimethylethyl)dimethylsilyl]oxy]-3-[(dimethylphenylsilyl)methyl]-2-(hydroxymethyl)cyclopentanone (35)

The residue containing 34 was dissolved in THF (80 mL) and transferred to a 500-mL round bottomed flask. To this solution was added yttrium trifluoromethanesulfonate (5.84 g) and aqueous formaldehyde (18.5 mL, 37 wt. % solution). The resulting mixture was stirred at room temperature for 12 hours to complete the reaction. The reaction was quenched by slow addition of water (30 mL) and extracted with ethyl acetate (2×50 mL). The combined organic layer was washed with brine (200 mL), dried over magnesium sulfate, and concentrated in vacuo to dryness to give the crude title compound (2.12 g, 57% yield).

Preparation of (3S,4S)-4-[[(1,1-Dimethylethyl)dimethylsilyl]oxy]-3-[(dimethylphenylsilyl)methyl]-2-methylenecyclopentanone (36)

To a solution of 35 (1.2 g, 3.06 mmol) in DCM (20 mL) was added triethylamine (0.554 mL, 3.97 mmol) at −0° C. slowly followed by methanesulfonyl chloride (0.284 mL, 3.67 mmol). The resulting mixture was stirred for 2 hours at room temperature to complete the reaction and form the mesylate. 1,8-diazabicyclo[5.4.0]undec-7-ene (0.685 mL, 4.58 mmol) was added to the reaction mixture and the reaction mixture was stirred for 3 hours at room temperature to complete the reaction. The reaction mixture was poured into a stirring mixture containing aqueous ammonium chloride solution (10%, 25 mL) and DCM (25 mL). The organic layer was separated and washed with water, brine, and dried over magnesium sulfate. Concentration of the organic layer in vacuo gave the crude title compound, 1.1 g in 96% yield.

Preparation of [1R-(1α,3β,4α)]-4-[[(1,1-Dimethylethyl)dimethylsilyl]oxy]-3-[(dimethylphenylsilyl)methyl]-2-methylenecyclopentanol (37)

To a cooled (−78° C.), stirred solution of 36 (4.8 g, 12.81 mmol) in THF (25 mL) in a 100-mL round bottomed flask equipped with an argon inlet was added lithium triethylborohydride (super hydride®, 24.4 mL, 24.4 mmol, 1.0 M THF solution) over a period of 15 minutes. The reaction mixture was stirred at the same temperature for 1 hour and slowly warmed to room temperature to complete the reaction. The reaction mixture was quenched with sodium hydroxide solution (10%, 25 mL) and extracted with ethyl acetate (2×25 mL). The organic layer was separated, washed with brine (50 mL), and dried over magnesium sulfate. Concentration of the organic layer in vacuo gave the crude title compound, 4.58 g in 95% yield in a 8:1 diastereomeric ratio. The title compound was purified by using silica gel flash chromatography ethyl acetate/hexanes (1:4 v/v) to afford the desired diastereomer, 4 g in 83% yield.

Preparation of [1S-(1α,3α,4β)]-9-[4-[[(1,1-Dimethylethyl)dimethylsilyl]oxy]-3-[(dimethylphenylsilyl)methyl]-2-methylenecyclopentyl]-6-iodo-9H-purin-2-amine (38, X=I)

To a solution of 37 (1.6 g, 4.24 mmol) in THF (20 mL) in a 100-mL round bottomed flask was added sequentially triphenylphosphine (1.49 g, 5.7 mmol), iodo guanine (1.49 g, 5.7 mmol) and diethylazodicarboxylate (0.91 mL, 5.7 mmol) at −78° C. The reaction mixture was stirred at −78° C. for 2 hours, then warmed slowly to room temperature over a period of 1 hour, and stirred at room temperature for 12 hours to complete the reaction. The reaction was quenched by addition of saturated ammonium chloride solution (50 mL) and the resulting mixture extracted with a mixture of tert-butyl methyl ether and heptane (1:4; 2×25 mL). The organic layer was dried over magnesium sulfate and concentrated in vacuo to give crude product which was purified by silica gel chromatography to afford the title compound in 71% yield (1.87 g).

Preparation of [1R-(1α,3α,5β)]-3-(2-Amino-6-iodo-9H-purin-9-yl)-5-hydroxy-2-methylenecyclopentanemethanol (39)

To a solution of 38 (1.8 g, 2.9 mmol) in DCM (25 mL) was added tetrafluoroboric acid-dimethyl ether complex (3.53 mL, 29 mmol) at room temperature. The resulting mixture was stirred for 4 hours. MeOH (25 mL) was added to the reaction mixture to make it homogenous. Solid potassium bicarbonate (4.35 g, 43.5 mmol) was slowly added and the resulting mixture stirred at room temperature for 1.5 hours. Potassium fluoride (0.85 g, 14.6 mmol) was added, followed by aqueous hydrogen peroxide (30 wt. % solution, 3 mL). The reaction mixture was stirred at room temperature for 4 hours. The reaction mixture was concentrated in vacuo to dryness to give a residue. The residue was triturated with DCM (3×25 mL). The combined organic layer was concentrated in vacuo to give the title compound as a solid (0.96 g, 85% yield).

Preparation of [1S-(1α,3α,4β)]-1,9-Dihydro-9-[4-hydroxy-3-(hydroxymethyl)-2-methylenecyclopentyl]-6H-purin-6-one (21)

A mixture of 39 (0.5 g, 1.29 mmol) in sodium hydroxide (2 N, 10 mL) was heated at 70° C. under an atmosphere of argon for 1 hour to complete the reaction. The reaction mixture was cooled to 0° C. and neutralized slowly by addition of 3 N HCl. Decolorizing carbon (0.5 g) was added. This mixture was heated at ~90° C. for 1 hour. The hot mixture was filtered through a bed of diatomaceous earth (Celite®). The resulting clear filtrate was cooled and seeded with 21 to effect crystallization. The product was collected by filtration and dried under vacuum to afford the title compound as a white crystalline solid (0.21 g, 60% yield).

EXAMPLE 12

Process for the Preparation of [1S-(1α,3α,4β)]-2-Amino-1,9-dihydro-9-[4-hydroxy-3-(hydroxymethyl)-2-methylenecyclopentyl]-6H-purin-6-one (21)

Preparation of 1R,4S)-4-[[(1,1-Dimethylethyl)dimethylsilyl]oxy]-2-iodo-2-cyclopenten-1-ol (40)

To a solution of 33 (40 g, 188 mmol, as prepared in Example 1) in THF (100 mL) in 1-L round bottomed flask was added a solution of iodine (105 g, 414 mmol) in DCM (100 mL). The resulting solution was stirred at 0° C. To this solution, pyridine (36 mL) was slowly added through a dropping funnel over a period of 20 minutes. The mixture was then stirred at the same temperature for 3 hours to complete the reaction. The reaction mixture was diluted with tert-butyl methyl ether (300 mL) and washed with sodium bisulfite solution (600 mL), HCl (0.5 N, 500 mL), brine (200 mL) and dried over magnesium sulfate. The organic layer was concentrated in vacuo to dryness to give the intermediate iodo-ketone as a yellow oil (56 g) in 89% yield.

To a round bottomed flask equipped with an argon inlet, magnetic stirrer was charged cerium chloride heptahydrate (30.8 g, 82.75 mmol) and MeOH (150 mL) and stirred at room temperature for 30 minutes. To this stirred solution, the iodo-ketone (56 g, 165.5 mmol) in MeOH (60 mL) was added and cooled to −60° C. To this cooled solution, sodium borohydride (6.25 g, 165.5 mmol) was added in portion-wise. After stirring the reaction mixture at −50° C. for 20 minutes, the reaction was warmed to −30° C. and stirred for another 30 minutes to complete the reaction as judged by TLC. The reaction mixture was diluted with tert-butyl methyl ether (400 mL) and washed with saturated sodium bicarbonate and brine. The organic layer was dried over magnesium sulfate and filtered on a sintered funnel. The filtrate was concentrated on a rotary evaporator to afford the desired product 40 as yellow oil (51 g, 91% yield).

Preparation of (3S,5R)-3-[[(1,1-Dimethylethyl)dimethylsilyl]oxy]-5-hydroxy-1-cyclopentene-1-carboxylic acid methyl ester (41)

To a solution of 40 (18 g, 52.89 mmol) in MeOH (100 mL) in a sealed reactor (Parr reactor) was added triethylamine (36 mL, 264.5 mmol) and dichlorobis(triphenylphosphine)palladium II [PdCl$_2$(Ph$_3$P)$_2$] (2 mole %). The reactor was flushed with nitrogen for about 5 minutes. The reactor was heated to about 50° C. and pressurized to about 15 psi. The reaction was continued while stirring at the same pressure and temperature for 5 hours to complete the reaction. The reaction mixture was concentrated, diluted with ethyl acetate (50 mL) and filtered. The organic layer was washed with water, brine and dried over magnesium sulfate. The organic layer was concentrated in vacuo to dryness to give crude product which was purified by column chromatography to give the title compound (11.6 g) in ~81% yield.

Preparation of (3S,5R)-5-(Benzoyloxy)-4-[[(1,1-dimethylethyl) dimethylsilyl]oxy]-1-cyclopentene-1-carboxylic acid methyl ester (42)

To a solution of 41 (0.55 g, 2 mmol) in THF (2 mL) at −78° C. was added lithium hexamethyldisilazide (3 mL, 1 M, 3 mmol) and the resulting solution was stirred for 1 hour. To this solution, 1-adamantanecarbonyl chloride (596 mg, 3 mmol) was added and the resulting mixture was stirred for 15 min at −78° C. followed by 30 minutes at room temperature to complete the reaction. The reaction mixture was diluted with ethyl acetate (25 mL) and washed with sodium bicarbonate solution, water, and brine. The organic layer was concentrated in vacuo to dryness to give the crude product. The crude product was crystallized from MeOH-water to give the title compound (0.57 g) in ~75% yield.

Preparation of (4S,5S)-4-[[(1,1-Dimethylethyl)dimethylsilyl]oxy]-5-[(dimethylphenylsilyl)methyl]-1-cyclopentene-1-carboxylic acid methyl ester (43)

To a suspension of magnesium (1.18 g, 48.5 mmol) in THF (15 mL) at room temperature was added phenyldimethylchlorosilane (8.86 g, 48.5 mmol). The resulting mixture was stirred for 1 hour to form the Grignard reagent. To this solution, copper (I) iodide (0.3 g, 5%) was added and the resulting solution stirred at room temperature for 30 minutes. The resulting solution was cooled to −78° C. and to it was added slowly a solution of 42 (14 g, 32.33 mmol) in THF (20 mL). The reaction mixture was stirred at −78° C. for 7 hours to complete the reaction. The reaction was quenched by slow addition of MeOH (10 mL) and warming to room temperature. The mixture was diluted with ethyl acetate (300 mL) and washed with saturated ammonium chloride (200 mL), sodium hydroxide (1 N, 2×150 mL), water (100 mL) and brine (100 mL). The organic layer was dried over magnesium sulfate and concentrated in vacuo to give the crude title compound, 13 g in 100% yield.

Preparation of (4S,5S)-4-[[(1,1-Dimethylethyl)dimethylsilyl]oxy]-5-[(dimethylphenylsilyl)methyl]-1-cyclopentene-1-methanol (44)

To a solution of 43 (15 g, 37.13 mmol) in hexanes (100 mL) was added diisobutylaluminum hydride (113 mL, 113.4 mmol, 1 N in hexanes) at −78° C. slowly over a period of 30 minutes keeping the temperature below −60° C. The resulting mixture was stirred for 2 hours at the same temperature to complete the reaction. The reaction mixture was quenched by addition of sodium hydroxide (2 N, 200 mL). The organic layer was separated and washed with water, brine, and dried over magnesium sulfate. The organic layer was concentrated in vacuo to dryness to give the crude title compound (13 g, 100% yield).

Preparation of (1R,2R,3S,5R)-3-[[(1,1-Dimethylethyl)dimethylsilyl]oxy]-2-[(dimethylphenylsilyl)methyl]-6-oxabicyclo[3.1.0]hexane-1-methanol (45)

To a cooled (0° C.), stirred solution of 44 (14 g, 37.23 mmol) in MeOH (50 mL) was added magnesium monoperoxyphthalate (MPPA, 80% pure, 27.62 g, 44.68 mmol) in six portions over a period of 1 hour, keeping the temperature <0° C. The reaction mixture was stirred at the same temperature for 4 hours to complete the reaction. The reaction mixture was diluted with ethyl acetate (300 mL) and washed with saturated sodium bisulfite (200 mL), sodium hydroxide (0.5 N, 2×150 mL), brine (150 mL) and dried over magnesium sulfate. The organic layer was concentrated in vacuo to dryness to give the crude title compound (13.5 g, 92%)

Preparation of [1S-(1α,2β,3α,5β)]-5-[2-Amino-6-(benzoyloxy)-9H-purin-9-yl]-3-[[(1,1-Dimethylethyl)dimethylsilyl]oxy]-2-[(dimethylphenylsilyl)methyl]-1-hydroxycyclopentanemethanol (46, X=BnO)

To a solution of 2-amino-6-O-benzyloxypurine (20 g, 84 mmol) in dimethylformamide (50 mL) at room temperature was added lithium hydride (0.4 g, 50.4 mmol) as a solid in one portion. The suspension was stirred at room temperature for 4 hours at which point a clear solution was observed. To this solution was added a solution of 45 (13.2 g, 33.6 mmol) in dimethylformamide (20 mL). The reaction mixture was heated at 80° C. for 4 hours to complete the reaction. The reaction mixture was diluted with ethyl acetate (200 mL) and washed with sodium hydroxide (1 N, 200 mL), water (100 mL) and brine (100 mL). The organic layer was stirred with charcoal (20 g) for 1 hour and filtered. The filtrate was concentrated in vacuo to dryness to give crude product (20.4 g). The crude product was crystallized from MeOH to give the title compound as white solid (8.8 g, 41% yield).

Preparation of [1S-(1α,3α,4β)]-2-amino-9-[4-[[(1,1-dimethylethyl) dimethylsilyl]oxy]-3-[(dimethylphenylsilyl)methyl]-2-methylenecyclopentyl]-9H-purin-6-one (47)

To a round bottomed flask equipped with a magnetic stirrer and nitrogen inlet/outlet was charged compound 46 (1.27 g, 2 mmol), trimethylorthoformate (2.12 g, 20 mmol) and $CH_2Cl_2$ at room temperature. The reaction mixture was cooled to 0° C. and pyridinium p-toluenesulfonate (5 mg) was added to the solution. The reaction mixture was warmed to room temperature and stirred overnight. The reaction mixture was concentrated in vacuo to dryness, and the resulting concentrate extracted with ethyl acetate (100 mL) and saturated $NaHCO_3$ solution (50 mL). The organic layer was separated, dried ($Na_2SO_4$), and concentrated in vacuo to afford thick light yellow oil. The oil was mixed with excess acetic anhydride (25 mL) and a catalytic amount of acetic acid (2 drops), and the resulting mixture was heated to reflux for 10 h. After cooling to room temperature, the excess acetic anhydride was removed by vacuum distillation, and the resulting brown oil was mixed with MeOH (30 mL) and 4 N HCl solution (10 mL). The solution was heated to reflux under a nitrogen atmosphere overnight. The MeOH was removed by distillation and the solution was neutralized to a pH of ~7.2 with NaOH (10 N, ~4.5 mL). The resulting suspension was extracted with $CH_2Cl_2$ (2×100 mL). The combined organic layer was dried ($Na_2SO_4$) and concentrated in vacuo to afford a thick semi-solid oil (compound 47). The crude compound 47 could be used in the next reaction without further purification.

Preparation of [1S-(1α,3α,4β)1-2-Amino-1,9-dihydro-9-[4-hydroxy-3-(hydroxymethyl)-2-methylenecyclopentyl]-6H-purin-6-one (21)

To a solution of compound 47 (1 g, 1.67 mmol) in DCM (10 mL) was added tetrafluoroboric acid-dimethyl ether complex (0.45 g, 3.34 mmol) at 0° C. The solution was stirred for 2 hours at 0° C. followed by 14 hours at room temperature. To this solution was added sequentially, potassium bicarbonate (10 g, 10 mmol), potassium fluoride (0.58 g, 10 mmol), and aqueous hydrogen peroxide (30 wt. % solution, 1.2 mL, 10.6 mmol). The reaction mixture was stirred at room temperature for 14 hours. The reaction mixture was concentrated in vacuo. The residue was recrystallized from water to afford the title compound (180 mg, 39% yield).

EXAMPLE 13

Process for the Preparation of [1S-(1α,3α,4β)]-2-Amino-1,9-dihydro-9-[4-hydroxy-3-(hydroxymethyl)-2-methylenecyclopentyl]-6H-purin-6-one (21)

Preparation of [3aS-(3aα,4α,5β,6aα)]-5-(Acetyloxy)-4-[(acetyloxy)methyl]hexahydro-2H-cyclopenta[b]furan-2-one (50)

To a 100 mL round bottomed flask was charged (3aS,6aR)-3,3a,6,6a-tetrahydro-2H-cyclopenta[b]furan-2-one 49 (3.85 g, 31 mmol, prepared as described in Corey et al. *J. Med*

*Chem.* 1993, 36, 243), paraformaldehyde (3.0 g), glacial acetic acid (30 mL), and concentrated sulfuric acid (1 mL). The mixture was heated to 74° C. for 24 hours. To the solution was added sodium acetate (4 g). The solution was concentrated in vacuo and the residue was dissolved in ethyl acetate (200 mL). The solution was washed with saturated sodium bicarbonate solution until no gas evolution was observed. The organic phase was dried over sodium sulfate and concentrated in vacuo to give the crude product (4.1 g). The crude product was purified by silica gel column chromatography to provide the title compound (3.1 g, 39%).

Preparation of [3aS-(3aα,4α,5β,6aα)]-Hexahydro-5-hydroxy-4-(hydroxymethyl)-2H-cyclopenta[b]furan-2-one (51)

To a solution of 50 (10.0 g, 39 mmol) in MeOH (100 mL) was added potassium carbonate (15 g). The suspension was stirred at room temperature for 3 hours. To the suspension was added ethyl acetate (60 mL). The resulting suspension was filtered through a pad of diatomaceous earth (Celite®). The filtrate was concentrated in vacuo to give crude product. The crude product was dissolved in MeOH (15 mL) and to it was added diethyl ether (100 mL). The resulting suspension was stirred for 2 hours at room temperature. The solid was filtered to give the title compound (3.62 g, 54%).

Preparation of (3aS-(3aα,4α,5β,6aα)]-5-[((1,1-Dimethylethyl) dimethylsilyl]oxy]-4-[[[(1,1-dimethylethyl)dimethylsilyl]oxy]methyl]hexahydro-2H-cyclopenta[b]furan-2-one (52)

To a suspension of 51 (4.1 g, 23.8 mmol) in DCM (40 mL) was added N,N-diisopropylethylamine (9.44 g, 71.4 mmol), 4-N,N-dimethylaminopyridine (0.41 g), and tert-butyldimethylsilyl chloride (10.8 g, 71.4 mmol). The reaction mixture was stirred at room temperature for 14 hours. The reaction was worked up by washing with 1.0 N HCl, 1.0 N sodium hydroxide, and brine. The organic solution was concentrated in vacuo to give the crude product. Column chromatography on silica gel using ethyl acetate/hexanes (½v/v) to give the title compound (7.8 g, 82%).

Preparation of [1R-(1α,2β,3α,5α)]-3-[[(1,1-Dimethylethyl) dimethylsilyl]oxy]-2-[[[(1,1-dimethylethyl) dimethylsilyl]oxy]methyl]-5-hydroxycyclopentanemethanol (54)

To a suspension of 52 (1.0 g, 2.5 mmol) and (1S)-(+)-(10-camphorsulfonyl) oxaziridine (0.86 g, 7.75 mmol) in THF (10 mL) was added sodium hexamethyldisilazide (5 mL of 1 M solution in THF) at −78° C. The reaction mixture was stirred for 1.5 hours. It was then quenched with MeOH (15 mL) at −78° C. and to the mixture was added sodium borohydride, (0.34 g, 9.0 mmol). The reaction mixture was warmed to room temperature and stirred for 1 hour. It was poured into ethyl acetate (100 mL), washed with 1.0 N sodium hydroxide (3×50 mL), dried over sodium sulfate, and concentrated in vacuo to give the crude triol intermediate 53A (1.1 g). The intermediate 53A was dissolved in MeOH (10 mL) and water (5 mL). To the resulting solution was added sodium periodate (2.14 g, 10.0 mmol) and the resulting mixture was stirred for 1 hour at room temperature. The mixture was poured into ethyl acetate (100 mL), washed with water (50 mL), dried over sodium sulfate, and concentrated in vacuo to give the crude aldehyde intermediate 53B. The residue was dissolved in MeOH (10 mL), and to it was added sodium borohydride (0.227 g, 6.0 mmol) at 0° C. The reaction mixture was stirred for 1 hour. Column purification of the crude product on silica gel using ethyl acetate/hexanes (½v/v) gave the title compound (0.68 g, 70%).

Preparation of [1R-(1α,2α,3β,4α)]-4-[[(1,1-Dimethylethyl) dimethylsilyl]oxy]-3-[[[(1,1-dimethylethyl) dimethylsilyl]oxy]methyl]-2-[[[(4-methylphenyl) sulfonyl]oxy]methyl]-cyclopentanol acetate ester (55)

To a solution of 54 (0.7 g, 1.79 mmol) in DCM (3 mL) was added pyridine (1 mL), and p-toluenesulfonyl chloride (0.34 g, 1.79 mmol) at 0° C. The reaction mixture was warmed to room temperature and stirred for 20 hours. To the reaction mixture was added pyridine (1 mL), and acetic anhydride (1 mL) at room temperature. The reaction mixture was stirred for 18 hours. It was poured into ethyl acetate (50 mL), washed with 1.0 N sodium hydroxide (2×20 mL), brine (20 mL), dried over sodium sulfate, and concentrated in vacuo to afford the title compound (0.86 g, 77%).

Preparation of [1R-(1α,3β,4α)]-4-[[(1,1-Dimethylethyl)dimethylsilyl]oxy]-3-[[[(1,1-dimethylethyl) dimethylsilyl]oxy]methyl]-2-methylenecyclopentanol (56)

To a solution of 55 (0.585 g, 0.88 mmol) in dimethylformamide (4 mL) was added lithium iodide (0.236 g, 1.76 mmol), and 1,8-diazabicyclo[5.4.0]undec-7-ene (10 eq). The resulting mixture was heated to 100° C. for 2 hours. The mixture was cooled to room temperature and to it was added MeOH (4 mL). The mixture was stirred for 14 hours at room temperature. It was poured into ethyl acetate (100 mL), washed with 1.0 N HCl (3×20 mL), brine (20 mL), dried over sodium sulfate, and concentrated in vacuo. Purification via silica gel chromatography using ethyl acetate/hexanes (1:2, v/v) gave the title compound (0.18 g, 52%).

Preparation of [1S-(1α,3α,4β)]-6-Chloro-9-[4-[[(1,1-dimethylethyl) dimethylsilyl]oxy]-3-[[[(1,1-dimethylethyl)dimethylsilyl]oxy]methyl]-2-methylenecyclopentyl]-9H-purin-2-amine (57)

To a suspension of 56 (120 mg, 0.32 mmol), triphenylphosphine (84.5 mg, 0.64 mmol), and 2-amino-6-chloropurine (108 mg, 0.64 mmol) in THF (10 mL) was added diethyl azodicarboxylate (111 mg, 0.64 mmol) at −20° C. The reaction mixture was stirred at −20° C. for 1 hour. It was poured into DCM (50 mL), washed with 0.5 N sodium hydroxide (3×10 mL), dried over sodium sulfate, and concentrated in vacuo. Purification via silica gel chromatography gave the title compound (0.11 g, 63%).

Preparation of [1S-(1α,3α,4β)]-6-Chloro-9-[4-hydroxy-3-(hydroxymethyl)-2-methylenecyclopentyl]-9H-purin-2-amine (39)

To a solution of 57 (180 mg, 0.344 mmol) in THF (2 mL) was added tetrabutylammonium fluoride (2 mL of 1 M solution in THF). The reaction mixture was stirred at room temperature for 1 hour. It was poured into DCM (50 mL), washed with water (3×10 mL), dried over sodium sulfate, and concentrated in vacuo to give the title compound (55 mg, 54%).

Preparation of [1S-(1α,3α,4β)]-2-Amino-1,9-dihydro-9-[4-hydroxy-3-(hydroxymethyl)-2-methylenecyclopentyl]-6H-purin-6-one (21)

39 was converted to 21 by the procedure described in Example 11.

EXAMPLE 14

Process for the Preparation of [1S-(1α,3α,4β)]-2-Amino-1,9-dihydro-9-[4-hydroxy-3-(hydroxymethyl)-2-methylenecyclopentyl]-6H-purin-6-one (21)

Preparation of (2-Benzyloxymethyl-6-oxa-bicyclo[3.1.0]hex-3-yloxy)-tert-butyl-dimethylsilane (83) ($R^c$=tert-butyl, $R^d$=$CH_3$)

A solution of t-butyldimethyl chlorosilane (3.58 g, 23.8 mmol) in DMF (10 mL) was slowly added to a solution of DMAP (0.25 g, 2.0 mmol), imidazole (3.24 g, 48 mmol), and 2-benyloxy-6-oxa-bicyclo[3.1.0]hexan-3-ol 82 (3.5 g, 15.9 mmol) in DMF (20 mL) at room temperature. The mixture was stirred at room temperature for 16 h. The reaction was quenched with water (50 mL) and extracted with ethyl acetate-hexane (1:1, 180 mL). The organic layer was separated, washed with water (80 mL) and half saturated brine (80 mL), and dried ($Na_2SO_4$). Concentration followed by purification with silica gel chromatography gave 4.85 g (91%) of desired product 83 as an oil.

Preparation of [3-(tert-Butyl-dimethyl-silanyloxy)-6-oxa-bicyclo[3.1.0]hex-2-yl]-methanol (84) ($R^c$=tert-butyl, $R^d$=$CH_3$)

A mixture of ether 83 (2.0 g), and 10% Pd/C (0.5 g) in MeOH (45 mL) was stirred at room temperature under hydrogen (1 atm) for 3.5 h. The mixture was treated with ethyl acetate (60 mL) for 10 min. The catalyst was removed by filtration on diatomaceous earth (Celite®) and washed with ethyl acetate (40 mL). Concentration of the filtrate under vacuum followed by purification of the product on a silica gel pad provided 1.39 g (95%) of alcohol 84 as an oil.

Preparation of Toluene-4-sulfonic acid 3-(tert-butyl-dimethyl-silanyloxy)-6-oxa-bicyclo[3.1.0]hex-2-ylmethyl ester (85) ($R^c$=tert-butyl, $R^d$=$CH_3$, $R^3$=p-methylphenyl)

A solution of p-toluenesulfonyl chloride (1.12 g, 5.9 mmol) in DCM (10 mL) was slowly added to a solution of alcohol 84, triethylamine (2.1 g, 21 mmol), and DMAP (0.12 g, 1.0 mmol) in DCM (25 mL) at room temperature. The mixture was stirred at room temperature for 16 h, treated with hexane (60 mL), washed with water (25 mL×3) and brine (20 mL), and dried ($Na_2SO_4$). Concentration of the solution followed by purification with silica gel chromatography gave 1.91 g (96%) of tosylate 85 as a white solid.

Preparation of tert-Butyl-dimethyl-(2-methylen-6-oxa-bicyclo[3.1.0]hex-3-yloxy)-silane (86) ($R^c$=tert-butyl, $R^d$=$CH_3$)

Potassium t-butoxide (1.9 g, 15.6 mmol) was added to a solution of tosylate 85 (5.2 g, 13.0 mmol) in THF (100 mL) at 0° C. After stirring at 0° C. for 1.5 h, the mixture was treated with hexane (200 mL), washed with water (100 mL×2) and brine (80 mL×2), dried ($Na_2SO_4$). Concentration of the solution gave 2.75 g (93%) of alkene 86 as an oil.

Preparation of 4-(tert-Butyl-dimethyl-silanyloxy)-2-[1,3]dithian-2-yl-3-methylene-cyclopentanol (87) ($R^c$=tert-butyl, $R^d$=$CH_3$)

A butyllithium solution (2.5 M in hexane, 4.8 mL, 12 mmol) was added to a solution of 1,3-dithiane (1.5 g, 12 mmol) in THF (22 mL) at 0° C. under nitrogen. The mixture was stirred at room temperature for 1 h and then cooled to 0° C. The above solution was slowly added to a solution of vinylepoxide 86 (2.3 g, 10 mmol) in THF (40 mL) at −30° C. The mixture was stirred at −30° C. for 3 h and then warmed up to room temperature. The reaction was quenched by addition of hexane (80 mL) and 5% aqueous $KH_2PO_4$ solution (70 mL). The organic layer was separated, washed with brine (60 mL×2), and dried ($Na_2SO_4$). Concentration of the solution followed by purification with silica gel chromatography gave 3.06 g (88%) of dithiane 87 as a white solid.

Preparation of 4-(tert-Butyl-dimethyl-silanyloxy)-2-hydroxymethyl-3-methylene-cyclopentanol (88) ($R^c$=tert-butyl, $R^d$=$CH_3$)

A mixture of dithiane 87 (0.60 g, 1.7 mmol), calcium carbonate (1.3 g, 13 mmol), and iodomethane (2.4 g, 16.4 mmol) in acetonitrile-water (94:6, 8 mL) was stirred at room temperature for 16 h. Ethyl acetate (10 mL) and hexane (10 mL) were added to the reaction mixture which was then dried over sodium sulfate. The solid was removed by filtration. Concentration of the filtrate provided a crude aldehyde which was then dissolved in ethanol and cooled to 0° C. Sodium borohydride (120 mg, 3.2 mmol) was added at 0 0° C. The mixture was stirred at 0° C. for 1 h. The reaction was quenched with a saturated aqueous $KH_2PO_4$ solution (5 mL) and water (5 mL). Ethanol was removed by evaporation under vacuum. The aqueous layer was extracted with ethyl acetate (15 mL×2). The combined organic layers were dried ($Na_2SO_4$). Concentration of the solution followed by purification with silica gel chromatography gave 301 mg (67%) of the diol 88.

Preparation of Acetic acid 2-acetoxymethyl-4-hydroxy-3-methylene-cyclopentyl ester (89) ($R^2$=$CH_3$)

Acetic anhydride (250 mg, 2.5 mmol) was added to a mixture of diol 88, DMAP (10 mg, 0.08 mmol), and triethylamine (360 mg, 3.6 mmol) in DCM (5 mL) under nitrogen at room temperature. After 3 h at room temperature, the reaction mixture was treated with hexane (10 mL), ethyl acetate (5 mL), and half saturated brine (10 mL). The organic layer was separated, washed with half saturated brine (10 mL), and dried ($Na_2SO_4$). Concentration of the solution gave a crude bis-acetate which was dissolved in THF (10 mL). Tetrabutylammonium fluoride (TBAF.3$H_2O$, 400 mg, 1.3 mmol) was added to the solution at room temperature. After 1 h, the reaction mixture was treated with ethyl acetate (20 mL) and then washed with brine (15 mL×2). The aqueous layers were back-extracted with ethyl acetate (15 mL). The combined organic layers were dried ($Na_2SO_4$). Concentration of the solution followed by purification with silica gel chromatography gave 255 mg (96%) of the desired alcohol 89 as an oil.

Preparation of Acetic acid 2-acetoxymethyl-4-(2-amino-6-iodopurin-9-yl)-3-methylene-cyclopentyl ester (90) ($R^2$=$CH_3$, X=I)

A mixture of alcohol 89 (100 mg, 0.44 mmol), triphenylphosphine (137 mg, 0.52 mmol), and 6-iodo-2-aminopurine (115 mg, 0.44 mmol) in THF was cooled to 0° C. DEAD (87 mg, 0.50 mmol) was slowly added to the mixture which was stirred at 0° C. for 3 h and then warmed up to room temperature for 16 h. The mixture was treated with ethyl acetate (9 mL) and filtered on diatomaceous earth (Celite®). Concentration of the filtrate provided a residue which was treated with ethyl acetate (3 mL), 2 N HCl (4 mL), and hexane (6 mL). The aqueous layer was separated. The organic layer was extracted with 2 N HCl (4 mL×3). The combined aqueous layers was neutralized with $K_2HPO_4$ to pH ~7 and extracted with ethyl acetate (25 mL, 10 mL). The combined organic layers were dried ($Na_2SO_4$) and concentrated to give a crude product which was purified by silica gel chromatography to provide 175 mg (85%) of 90 containing some triphenylphosphine oxide. Crystallization of the crude product from ethanol gave 132 mg (64%) of desired 90.

The compound of formula 90 can be converted to the compound of formula 21 by hydrolysis of the ester group using, for example, by treatment with an alkali metal alkoxide. The 6-iodo group can be hydrolyzed to provide the compound of formula 21, according to the procedure described for the preparation of compound of formula 21 in Example 11.

Where noted above, publications and references, including but not limited to patents and patent applications, cited in this specification are herein incorporated by reference in their entirety in the entire portion cited as if each individual publication or reference were specifically and individually indicated to be incorporated by reference herein as being fully set forth.

While this invention has been described with an emphasis upon preferred embodiments, it will be obvious to those of ordinary skill in the art that variations in the preferred devices and methods may be used and that it is intended that the invention may be practiced otherwise than as specifically described herein. Accordingly, this invention includes all modifications encompassed within the spirit and scope of the invention as defined by the claims that follow. For example, it should be understood that the reaction steps set forth in the appended claims need not necessarily be performed in the order in which they appear, and one skilled in the field may be able to vary the order of reaction steps. Additionally, certain reaction sequences may be performed simultaneously, such as, for example, protodesilylation and debenzylation, or these reactions can be performed in separate steps, without departing from the spirit and scope of the invention. It is intended that all such modifications are encompassed within the scope of the appended claims.

The invention claimed is:

1. A method for isolating entecavir or an entecavir intermediate from a diluted mixture, the diluted mixture comprising entecavir and water or a mixture comprising an entecavir intermediate and other process reagents comprising:
   (a) adsorbing the diluted mixture onto a hydrophobic resin bed;
   (b) washing the resin bed with water to remove salt; and
   (c) eluting the entecavir or entecavir intermediate from the resin bed with an organic solvent.

2. The method of claim 1 wherein the hydrophobic resin is a brominated styrene based resin.

* * * * *

UNITED STATES PATENT AND TRADEMARK OFFICE
CERTIFICATE OF CORRECTION

| | | |
|---|---|---|
| PATENT NO. | : 7,541,460 B2 | Page 1 of 1 |
| APPLICATION NO. | : 11/311194 | |
| DATED | : June 2, 2009 | |
| INVENTOR(S) | : Yeung Yu Chan et al. | |

It is certified that error appears in the above-identified patent and that said Letters Patent is hereby corrected as shown below:

On the Title Page:

Item (54), change "3-METHYLENECYCLOPENTYL]-" to -- 2-METHYLENECYCLOPENTYL]- --.

Item (56), References Cited, under OTHER PUBLICATIONS:

Column 2:

Carceller et al. reference, change "bicyco" to -- bicyclo --.

The reference should read:

-- Carceller et al., "Synthesis of cis-bicyclo [13.3.0]oct-3-ene-2,7-dione, a highly functionalized cyclopentanoid intermediate," Tetrahedron Letters, vol. 25, Issue 19, 1984, pp. 2031-2034. --.

Pearson, A.J. et al. reference, change "2547" to -- 2457 --.

The reference should read:

-- Pearson, A.J. et al., "Conjugate Additions of Carbon Nucleophiles to Cyclopentadienones," Organic Letters, vol. 5, No. 14, 2003, pp. 2457-2459. --.

In the Specification:

Column 1, line 5, change "3-METHYLENECYCLOPENTYL]-" to -- 2-METHYLENECYCLOPENTYL]- --.

Signed and Sealed this
Twenty-fifth Day of October, 2011

David J. Kappos
*Director of the United States Patent and Trademark Office*